US011897928B2

(12) United States Patent
Kahl et al.

(10) Patent No.: US 11,897,928 B2
(45) Date of Patent: Feb. 13, 2024

(54) CONJUGATES FOR DELIVERING AN ANTI-CANCER AGENT TO NERVE CELLS, METHODS OF USE AND METHODS OF MAKING THEREOF

(71) Applicant: Manzanita Pharmaceuticals, Inc., Woodside, CA (US)

(72) Inventors: Stephen B. Kahl, Woodside, CA (US); Constance A. McKee, Woodside, CA (US)

(73) Assignee: Manzanita Pharmaceuticals, Inc., Woodside, CA (US)

( * ) Notice: Subject to any disclaimer, the term of this patent is extended or adjusted under 35 U.S.C. 154(b) by 0 days.

(21) Appl. No.: 17/259,127

(22) PCT Filed: Jul. 17, 2019

(86) PCT No.: PCT/US2019/042253
§ 371 (c)(1),
(2) Date: Jan. 8, 2021

(87) PCT Pub. No.: WO2020/018700
PCT Pub. Date: Jan. 23, 2020

(65) Prior Publication Data
US 2021/0147499 A1 May 20, 2021

Related U.S. Application Data

(60) Provisional application No. 62/700,131, filed on Jul. 18, 2018.

(51) Int. Cl.
*C07K 14/48* (2006.01)
*A61K 45/06* (2006.01)
*C07D 211/60* (2006.01)
*C07D 225/04* (2006.01)
*C07D 235/04* (2006.01)
*C07D 249/08* (2006.01)
*C07D 265/30* (2006.01)

(52) U.S. Cl.
CPC ............. *C07K 14/48* (2013.01); *A61K 45/06* (2013.01); *C07D 211/60* (2013.01); *C07D 225/04* (2013.01); *C07D 235/04* (2013.01); *C07D 249/08* (2013.01); *C07D 265/30* (2013.01)

(58) Field of Classification Search
CPC .................. C07K 14/48; A61K 45/06
See application file for complete search history.

(56) References Cited

U.S. PATENT DOCUMENTS

| 4,469,774 | A | 9/1984 | Lee |
|---|---|---|---|
| 5,094,848 | A | 3/1992 | Brixner |
| 5,149,794 | A | 9/1992 | Yatvin et al. |
| 5,200,534 | A | 4/1993 | Rao |
| 5,202,448 | A | 4/1993 | Carver et al. |
| 5,229,500 | A | 7/1993 | Barde et al. |
| 5,229,529 | A | 7/1993 | Ueno et al. |
| 5,232,695 | A | 8/1993 | Wilcox et al. |
| 5,274,137 | A | 12/1993 | Nicolaou et al. |
| 5,279,949 | A | 1/1994 | Nair |
| 5,283,253 | A | 2/1994 | Holton et al. |
| 5,294,637 | A | 3/1994 | Chen et al. |
| 5,349,056 | A | 9/1994 | Panayotatos |
| 5,389,623 | A | 2/1995 | Bodor |
| 5,415,869 | A | 5/1995 | Straubinger et al. |
| 5,438,121 | A | 8/1995 | Barde et al. |
| 5,470,997 | A | 11/1995 | Buechler et al. |
| 5,486,599 | A | 1/1996 | Saunders et al. |
| 5,502,037 | A | 3/1996 | Kondratyev |
| 5,505,931 | A | 4/1996 | Pribish |
| 5,512,661 | A | 4/1996 | Shooter et al. |
| 5,554,498 | A | 9/1996 | Filler et al. |
| 5,556,837 | A | 9/1996 | Nestler et al. |
| 5,563,250 | A | 10/1996 | Hylarides et al. |
| 5,599,506 | A | 2/1997 | Sluclak |
| 5,599,560 | A | 2/1997 | Siuciak |
| 5,614,487 | A | 3/1997 | Battersby et al. |

(Continued)

FOREIGN PATENT DOCUMENTS

| EP | 0590267 | 4/1994 |
|---|---|---|
| WO | WO 199108770 | 6/1991 |

(Continued)

OTHER PUBLICATIONS

Vanhecke et al. Clin Cancer Res (2011) 17 (7): 1741-1752.*
Pacey, S. et al. (2011) "A phase I study of the heat shock protein 90 inhibitor alvespimycin (17-DMAG) given intravenously to patients with advanced solid tumors"; *Clinical cancer research*, vol. 17, No. 6; pp. 1561-1570.
Pardoll, Drew M. (2012) "The blockade of immune checkpoints in cancer immunotherapy"; *Nat Rev Cancer* 12(4); pp. 252-264.
Touat, M. et al., "Glioblastoma targeted therapy: updated approaches from recent biological insights", *Annals of Oncology*, vol. 28; pp. 1457-1472.
Zhang, Y. et al., (2001) "Neuroprotect ion in transient focal brain ischemia after delayed intravenous administration of brain-derived neurotrophic factor conjugated to a blood-brain barrier drug targeting system"; *Stroke*, vol. 32(6); pp. 1378-1384.

(Continued)

*Primary Examiner* — Jeanette M Lieb
(74) *Attorney, Agent, or Firm* — Khin K. Chin; Bozicevic, Field & Francis LLP

(57) ABSTRACT

Conjugates for delivering an anti-cancer agent to nerve cells are provided. Conjugate compounds of the present disclosure according to certain embodiments include a compound having a protein, peptide or pepetidomimetic that binds selectively to a neurotrophin receptor, an anti-cancer agent and a linker that covalently bonds the anti-cancer agent to the protein, peptide or pepetidomimetic binds selectively to the neurotrophin receptor. Compositions and methods for delivering an anti-cancer agent selectively into nerve cells (e.g., in the treatment of optic pathway glioma) as well as indications such as perineural invasion and skin cancers are also described. Also provided are methods of making the anti-cancer conjugate compounds.

10 Claims, No Drawings

(56) References Cited

U.S. PATENT DOCUMENTS

| | | | |
|---|---|---|---|
| 5,614,652 A | 3/1997 | Filler et al. | |
| 5,622,862 A | 4/1997 | Squinto et al. | |
| 5,648,334 A | 7/1997 | Davis et al. | |
| 5,683,894 A | 11/1997 | Edwards et al. | |
| 5,728,803 A | 3/1998 | Urfer et al. | |
| 5,767,288 A | 6/1998 | Rock et al. | |
| 5,824,701 A | 10/1998 | Greenwald et al. | |
| 5,827,823 A | 10/1998 | Siuciak et al. | |
| 5,833,988 A | 11/1998 | Friden | |
| 5,846,935 A | 12/1998 | Panayotatos | |
| 5,869,680 A | 2/1999 | Mas et al. | |
| 5,882,941 A | 3/1999 | Essigmann et al. | |
| 5,948,384 A | 9/1999 | Filler | |
| 5,977,307 A | 11/1999 | Friden et al. | |
| 5,981,480 A | 11/1999 | Urfer et al. | |
| 6,077,829 A | 6/2000 | Tanaka et al. | |
| 6,197,743 B1 | 3/2001 | Faller | |
| 6,406,710 B1 | 6/2002 | Panayotatos | |
| 6,410,510 B1 | 6/2002 | Panayotatos et al. | |
| 6,472,178 B1 | 10/2002 | Fandl et al. | |
| 6,472,179 B2 | 10/2002 | Stahl et al. | |
| 6,486,303 B1 | 11/2002 | Moyie | |
| 6,503,728 B1 | 1/2003 | Urfer et al. | |
| 6,576,636 B2 | 6/2003 | Webb et al. | |
| 6,887,861 B1 | 5/2005 | Hill et al. | |
| 7,144,983 B1 | 12/2006 | Urfer et al. | |
| 7,528,233 B2 | 5/2009 | Urfer et al. | |
| 2004/0120891 A1 | 6/2004 | Hill et al. | |
| 2010/0028370 A1 | 2/2010 | Zankel et al. | |
| 2010/0266492 A1* | 10/2010 | Webb | A61K 47/6807 514/8.4 |
| 2013/0123175 A1 | 5/2013 | Hill et al. | |
| 2017/0121367 A1 | 5/2017 | Villoslada et al. | |
| 2018/0042921 A1 | 2/2018 | Huang | |
| 2022/0378949 A1 | 12/2022 | McKee et al. | |

FOREIGN PATENT DOCUMENTS

| | | |
|---|---|---|
| WO | WO 1993/10234 | 5/1993 |
| WO | WO 1993010076 | 5/1993 |
| WO | WO 1993023555 | 11/1993 |
| WO | WO 1994007876 | 4/1994 |
| WO | WO 1994007880 | 4/1994 |
| WO | WO 1994007881 | 4/1994 |
| WO | WO 1994007882 | 4/1994 |
| WO | WO 1995007092 | 3/1995 |
| WO | WO 199532738 | 7/1995 |
| WO | WO 199641166 | 12/1996 |
| WO | WO 199721732 | 6/1997 |
| WO | WO 199723608 | 7/1997 |
| WO | WO 199726275 | 7/1997 |
| WO | WO 199737966 | 10/1997 |
| WO | WO 199744063 | 11/1997 |
| WO | WO 1998013059 | 4/1998 |
| WO | WO 1998022451 | 5/1998 |
| WO | WO 1998028288 | 7/1998 |
| WO | WO 199841220 | 9/1998 |
| WO | WO 1998058927 | 12/1998 |
| WO | WO 1999009021 | 2/1999 |
| WO | WO 1999014209 | 3/1999 |
| WO | WO 1999018113 | 4/1999 |
| WO | WO 199921552 | 5/1999 |
| WO | WO 2000037103 | 6/2000 |
| WO | WO 2000053236 | 9/2000 |
| WO | WO 2001091798 | 12/2001 |

OTHER PUBLICATIONS

Agarwal, et al., "Effects of dexamethasone (DEX) on growth factor and neurotrophin mRNA expression by cultured human trabecular meshwork cells"; IOVS (Mar. 15, 1999) vol. 40, No. 4, pp. S667 (Ann Mtg. of the Assoc for Research in Vision and Ophthalmology Fort Lauderdale, Florida, USA (May 9-14, 1999).

Barbany, (1996), "Modulation of neurotrophins and their receptors by adrenal steroids", CNS Neurotransmitters and Neuromodulators: Neuroactive Steroids; pp. 113-125.

Barbany, et al. (1992) "Regulation ofNeurotrophin mRNA Expression in the rat brain by glucocorticoids"; Eur J Neurosci, 4 (5): 396-403.

Barbany, et al. (1993) "Adrenalectomy attenuates kainic acid-elicited increases of messenger RNAs for neurotrophins and their receptors in the rat brain"; Neuroscience, vol. 54, No. 4; pp. 909-922.

Binkley et al. (1995)"RNA Ligands to Human Nerve Growth Factor"; Nucleic Acids Research vol. 23 No. 16; pp. 3198-3205.

Brandoli, et al. (1998) "Dexamethasone decreases P75NTR expression in injured spinal cord", Society for Neuroscience, vol. 24, No. 1-2; Abstracts; pp. 290 (28th Ann Mtg. of the Society for Neuroscience, Part 1).

Cosi, et al. (1993) "Giucocorticoids depress activity-dependent expression of BDNF mRHA in hippocampal neurons"; Neuroreport, vol. 4, No. 5; pp. 527-530.

Fink Jr., et al. (1997) "Effect of glucocorticoid on NGF-stimulated TRKA signaling in PC 12 cells"; Society for Neuroscience Abstracts, vol. 23, No. 1-2, pp. 1702 (27th Ann Mtg. of the Society for Neuroscience, New Orleans, Louisiana, USA Oct. 25-30, 1997).

Fiume et al. (1986). "Drug Targeting in Antiviral Chemotherapy: A Chemically Stable Conjugate of 9-β-DArabinofuranosyl-Adenine 5'-Monophosphate with Lactosaminated Albumin Accomplishes a Selective Delivery of the Drug to Liver Cells"; Biochemical Pharmacology vol. 35 No. 6: pp. 967-972.

Fiume et al., "Galactosylated poly(L-lysine) as a hepatotropic carrier of 9-β-D-arabinofuranosyladenine 5'-monophosphate"; FEBS 3810 vol. 203 No. 2: pp. 203-206 (Jul. 1986).

Gonzalez, et al., "Glucocorticoid regulation of motoneuronal parameters in rats with spinal cord injury", Cellular and Molecular Neurobiology, (Oct. 1999) vol. 19, No. 5, pp. 597-611.

Harlow (1988) Antibodies: A Laboratory Manual, pp. 327-333.

Haschke et al., "Preparation and Retrograde Axonal Transport of an Antiviral Drug/Horseradish Peroxidase Conjugate"; Journal of Neurochemistry vol. 35 No. 6: pp. 1431-1435 (Dec. 1980).

Haubensak, et al. (1998) "BDNF-GFP containing secretory granules are localized in the vicinity of synaptic junctions of cultured cortical neurons";. Journal of Cell Science 111:(Pt 11): 1483-1493.

Higaki, et al., "Neurotropin $^R$ inhibits lipopolysaccharide-induced nitric oxide production in cultured human endothelial cells", Cell structure and function, (1994) vol. 19, No. 6, pp. 555 (47th Ann Mtg. of the Japan Society for Cell Biology, Nagasaki, Japan, Sep. 28-30, 1994).

Jelsma, et al. (1993) "Different forms of the neurotrophin receptor TrkB mRNA predominate in rat retina and optic nerve", Journal of Neurobiology, vol. 24, No. 9, pp. 1207-1214.

Kandel, et al (1991) *Principles of Neural Science, 3rd Edition*, pp. 131-133.

Kawata et al. (1998) "Steroid Hormones and their Receptors in the Brain"; J. Steroid Biochem Mol Bioi, vol. 65, No. 1-6; pp. 273-280.

Khotskaya, et al (2017) "Targeting TRK family proteins in cancer"; Pharmacology & Therapeutics, vol. 173; pp. 58-66.

Ko, et al (2012) "Small Molecule Ligands for Active Targeting of TrkC-Expressing Tumor Cells"; *ACS Med Chem Letters*. 3(12); pp. 1008-1012.

Kononen, et al., "Neurotrophins and their receptors in the rat pituitary gland: regulation of BDNF and trk B mRNA levels by adrenal hormones", Molecular Brain Research, (1994) vol. 27, No. 2, pp. 347-354.

Kramer et al., "Monoclonal antibody to human trk-A: diagnostic and therapeutic potential in neuroblastoma"; European Journal of Cancer vol. 33 No. 12: pp. 2090-2091 (Oct. 1997).

Li et al. "β-Endorphin Omission Analogs: Dissociation of Immunoreactivity from Other Biological Activities,"Proc. Natl. Acad. Sci. USA 77( 6): 3211-3214 (1980).

Lindholm, et al., "Glucocorticoids and neurotrophin gene regulation in the nervous system", Annals of the New York Academy of Sciences, (Nov. 30, 1994) 746, 195-202.

(56) References Cited

OTHER PUBLICATIONS

Maliartchouk et al., "Optimal Nerve Growth Factor Trophic Signals Mediated by Synergy of TrkA and p75 Receptor-Specific Ligands", Journal of Neuroscience vol. 17 No. 16: pp. 6031-6037 (1997).
Martin et al. (1981) "Immunospecific targeting of liposomes to cells: a novel and efficient method for covalent attachment of Fab' fragments via disulfide bonds"; Biochemistry, 20(14):4229-4238.
Nemoto, et al., "A possible mechanism of TPA-mediated downregulation of neurotrophin-3 gene expression in rat cultured vascular smooth muscle cells", Molecular Brain Research, (May 7, 1999) vol. 68, No. 1-2, pp. 186-189.
Panchuk-Voloshina, et al (1999) "Alexa Dyes, a Series of New Fluorescent Dyes that Yield Exceptionally Bright, Photostable Conjugates"; Journal of Histochemistry & Cytochemistry 47:1179-1188.
Pardridge et al., "Transport of Human Recombinant Brain-Derived Neurotrophic Factor (BDNF) Through the Rat Blood-Brain Barrier in Vivo Using Vector-Mediated Peptide Drug Delivery" Pharmaceutical Research vol. 11 No. 5: pp. 746 (1994).
Pluckthun (1994) "Antibodies from *Escherichia coli*"; The Pharmacology of Monoclonal Antibodies, vol. 113; pp. 269-315.
Ponzetto et al., "Adenine arabinoside monophosphate and acyclovir monophosphate coupled to lactosaminated albumin reduce woodchuck hepatitis virus viremia at doses lower than do the unconjugated drugs"; Hepatology vol. 14: pp. 16-24 (1991).
Prodanov, et al., "Pharmacology of apoptosis in the central nervous system", Farmatsiya, (Sofia) (1998), 45(2), 31-38.
Robinson et al. (1995) "Structure of the brain-derived neurotrophic factor/neurotrophin 3 heterodimer": Biochem, 34(13):4139-4146.
Rudinger, J. (1976) "Peptide Hormones" (ed., J.A. Parsons) University Park Press, Baltimore, pp. 1-7.
Schwab et al., "Labeled Wheat Germ Agglutinin (WGA) as a New, Highly Sensitive Retrograde Tracer in the Rat Brain Hippocampal System," Brain Research vol. 152 No. 1: pp. 145-150 (Aug. 18, 1978).
Schwab et al., "Selective retrograde transsynaptic transfer of a protein, tetanus toxin, subsequent to its retrograde axonal transport"; Journal of Cell Biology vol. 82 No. 3: pp. 798-810 (Sep. 1979).
Schwab, M.E., "Ultrastructural localization of a nerve growth factor-horseradish peroxidase (NGF-HRP) coupling product after retrograde axonal transport in adrenergic neurons": Brain Research vol. 130 No. 1: pp. 190-196 (Jul. 8, 1977).
Scully, et al, "Neurotrophin expression modulated by glucocorticoids and oestrogen in immortalized hippocampal neurons", Molecular Brain Research, (1995) vol. 31, No. 1-2, pp. 158-164.
Scully, et al., "Glucocorticoid modulation of neurotrophin expression in immortalized mouse hippocampal neurons"; Neuroscience Letters, (1993) vol. 155, No. 1, pp. 11-14.
Scully, et al., "Modulation of neurotrophin expression by glucocorticoids in immortalized hippocampal neurons", Society for Neuroscience Abstract, (1993) vol. 19, No. 1-3, pp. 256 (23rd Ann Mtg. of the Society for Neuroscience, Washington D.C., USA, Nov. 7-12, 1993).
Seidl, et al., "Expression of nerve growth factor and neurotrophin receptors in testicular cells suggest novel roles for neurotrophins outside the nervous system", Reproduction Fertility and Development, (1996) vol. 8, No. 7, pp. I 075-1087.
Sharma, et al. (2011) "Novel cancer immunotherapy agents with survival benefit: recent successes and next steps"; *Nat Rev Cancer* 11(11); pp. 805-812.
Shi, et al., "Dexamethasone Induces Hypertrophy of Developing Medial Septum Cholinergic Neurons: Potential Role of Nerve Growth Factor"; Journal of Neuroscience, (Nov. IS, 1998) vol. 18, No. 22, pp. 9326-9334.
Skolnick et al., "From genes to protein structure and function: novel applications of computational approaches in the genomic era," Trends in Biotechnology vol. 18 No. 1: pp. 34-39 (2000).
Smith, et al, "Regulation of NGFI-A (Egr-1) gene expression by the POU domain transcription factor Brn-3a"; Brain Research, Molecular Brain Research, (Dec. 10, 1999) 74 (1-2) 117-25.
Toran-Allerand, et al. (1996) "Cross-Coupling of Estrogen and Neurotrophin Receptor Systems in Developing Cerebral Cortex"; Internat. J. Develop. Neurosci., vol. 14, Suppl. 1; p. 99.
Verity, et al., "Regulation of Glial Cell Line-Derived Neurotrophic Factor Release from Rat C6 Glioblastoma Cells", Journal of Neurochemistry, (Feb. 1998) vol. 70, No. 2, pp. 531-539.
Wiesmann et al. (2001) "Nerve growth factor: structure and function"; Cell Mol. Life Sci., 58:748-759.
Wilcox et al., "Characterization of Nerve Growth Factor-Dependent Herpes Simplex Virus Latency in Neurons In Vitro"; Journal of Virology vol. 62 No. 2: pp. 393-399 (Feb. 1988).
Woo et al. (1998) "Characterization of the recombinant extracellular domain of the neurotrophin receptor TrkA and its interaction with nerve growth factor (NGF)"; Protein Sci., 7:1006-1016.
Yang, et al., "Dexamethasone inhibits ischemia-induced transient reduction of neurotrophin-3 mRNA in rat hippocampal neurons"; Neuroreport, (Oct. 26, 1998) vol. 9, No. 15, pp. 3477-3480.
Zapata, et al (1995) "Engineering linear $F(ab')_2$ fragments for efficient production in *Escherichia coli* and enhanced antiproliferative activity"; Protein Eng. 8(10); pp. 1057-1062.

\* cited by examiner

CONJUGATES FOR DELIVERING AN ANTI-CANCER AGENT TO NERVE CELLS, METHODS OF USE AND METHODS OF MAKING THEREOF

CROSS REFERENCE TO RELATED APPLICATION

Pursuant to 35 U.S.C. § 119(e), this application claims priority to the filing date of U.S. Provisional Patent Application No. 62/700,131, filed Jul. 18, 2018; the disclosure of which application is herein incorporated by reference.

INTRODUCTION

Central nervous system (CNS) tumors occur in up to 20% of children who have the genetic disease neurofibromatosis. Of the CNS tumors, most (~90%) optic pathway gliomas are low-grade gliomas that are indolent and slow-growing with a good prognosis. By contrast, high-grade gliomas emerge quickly, advance rapidly, and are almost always lethal. Children exhibited loss of vision in 50% of cases, where about 85% of these optic pathway gliomas are unresectable, sited in the optic nerves and/or chiasm. To treat gliomas, drug therapy typically includes systemic chemotherapy, such as administering carboplatin or vinblastine. However, an estimated 40% of children stop carboplatin treatment due to dose toxicities.

SUMMARY

Aspects of the present disclosure include conjugate compounds for delivering an anti-cancer agent to nerve cells. Conjugate compounds according to certain embodiments include a compound having a protein, peptide or pepetidomimetic that binds selectively to a neurotrophin receptor, an anti-cancer agent and a linker that covalently bonds the anti-cancer agent to the protein, peptide or pepetidomimetic binds. Compositions and methods for delivering an anti-cancer agent selectively into nerve cells (e.g., in the treatment of indications such as cancers of the central nervous system including adult and pediatric gliomas, optic pathway glioma, spinal tumors, neurofibromatomas, schwannomas, malignant peripheral nerve sheath tumors, malignant schwannoma, neurofibrosarcoma, neurosarcoma) as well as indications such as perineural invasion and skin cancers are also described. Also provided are methods of making the anti-cancer conjugate compounds.

In embodiments, conjugate compounds for delivering an anti-cancer agent to a nerve cell include a compound of Formula I:

$$B-L-X \qquad (I)$$

where B is a protein, peptide or pepetidomimetic that binds selectively to a neurotrophin receptor; L is a linker; and X is an anti-cancer agent. In embodiments, the anti-cancer agent is configured to selectively bind to a neurotrophin receptor. In some embodiments, the anti-cancer agent (in some instances, the entire conjugate) is configured to be internalized into a cancer cell. In some embodiments, the cancer is a cancer of the central nervous system, such as a cancer selected from the group consisting of adult and pediatric gliomas, optic pathway glioma, spinal tumors, neurofibromatomas, schwannomas, malignant peripheral nerve sheath tumors, malignant schwannoma, neurofibrosarcoma, neurosarcoma. In certain instances, the cancer is optic pathway glioma. In other instances, the cancer comprises perineural invasion. In yet other instances, the cancer is skin cancer.

In some embodiments, the anti-cancer agent is a mammalian target of rapamycin (mTOR) inhibitor or mitogen-activated protein kinase (MEK) inhibitor. In one example, the anti-cancer agent is an mTOR inhibitor such as sirolimus, temsiorolimus, everolimus, and ridaforolimus. In some instances, the anti-cancer agent is everolimus. In some instances, the compound is of Formula IA1 or Formula IA2:

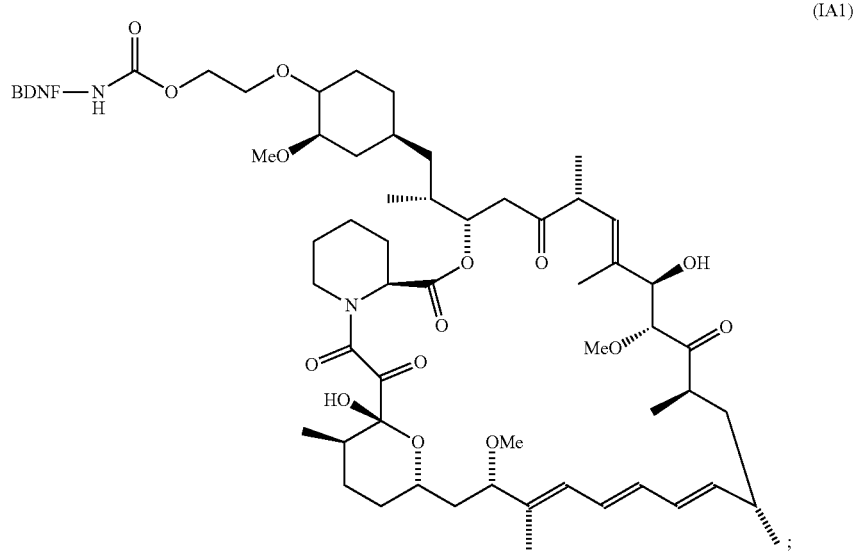

(IA1)

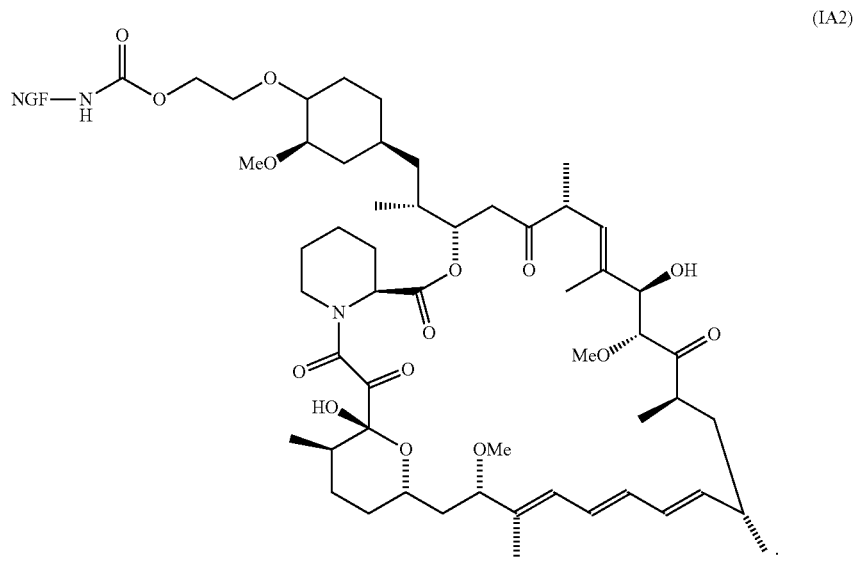

(IA2)

In another example, the anti-cancer agent is an MEK inhibitor such as trametinib, dabrafenib, cobimetinib, vemurafenib, binimetinib, and selumetinib. In some instances, the anti-cancer agent is selumetinib. In certain instances, the compound is of Formula IB1 or Formula IB32:

(IB1)

(IB2)

In certain embodiments, the cancer comprises perineural invasion. In some embodiments, the anti-cancer agent is a heat shock protein 90 (hsp90) inhibitor. In some examples, the hsp90 inhibitor is a compound selected from the group consisting of:

a) alvespinomycin:

b) 17-N-Allylamino-17-demethoxygeldanamycin (17AAG):

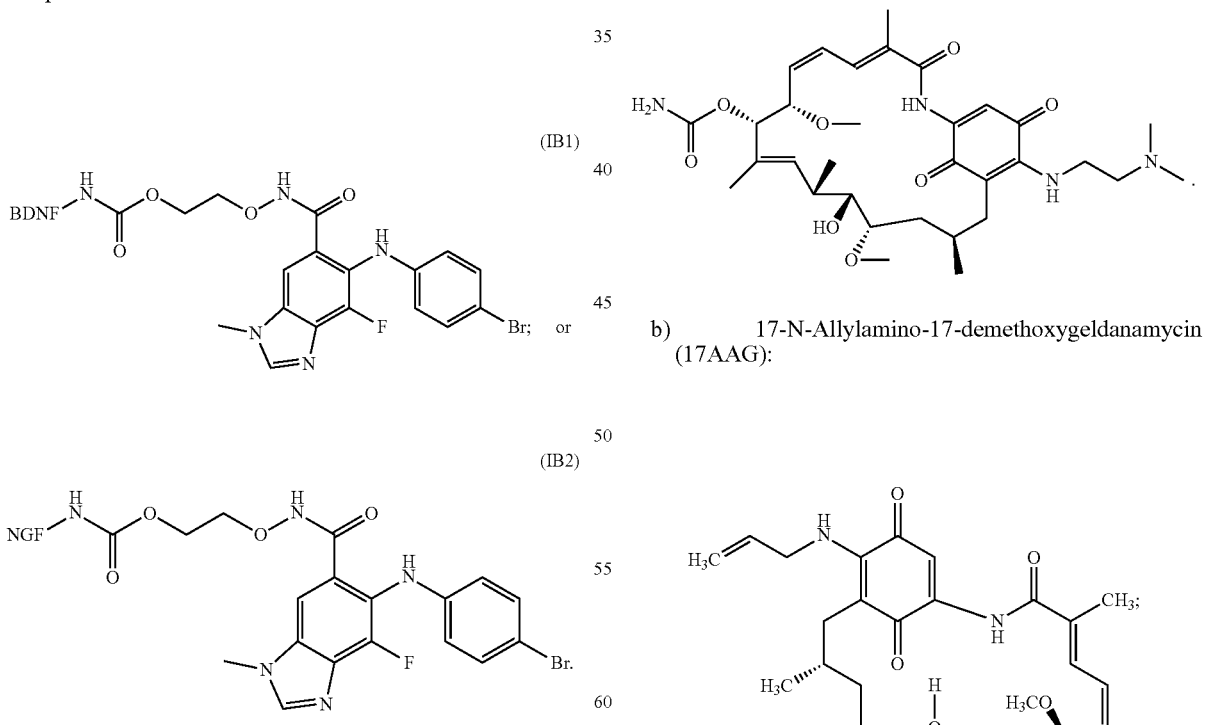

c) luminespib (AUY-922, NVP-AUY922):
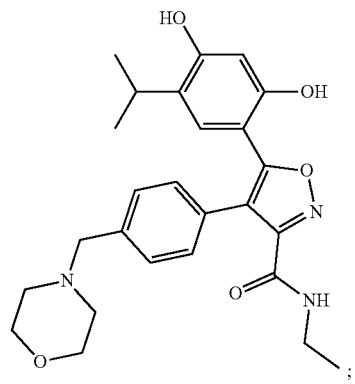 [SMILES: CCNC(=O)c1noc(-c2cc(C(C)C)c(O)cc2O)c1-c1ccc(CN2CCOCC2)cc1]
d) ganetespib (STA-9090):
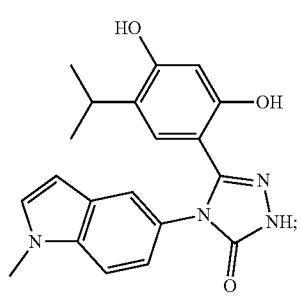 [SMILES: CC(C)c1cc(-c2n[nH]c(=O)n2-c2ccc3c(ccn3C)c2)c(O)cc1O]
e) onalespib (AT13387):
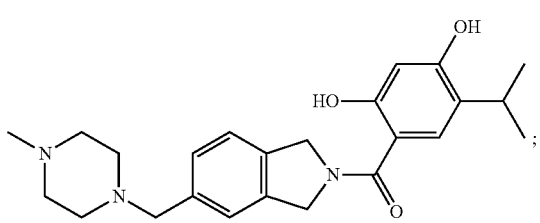 [SMILES: CC(C)c1cc(C(=O)N2Cc3ccc(CN4CCN(C)CC4)cc3C2)c(O)cc1O]
f) NVP-BEP800:
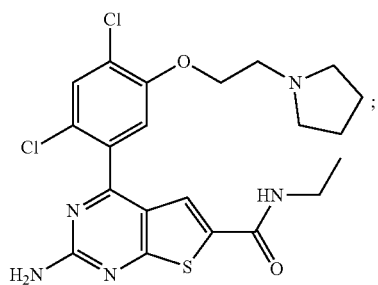 [SMILES: CCNC(=O)c1cc2c(-c3cc(OCCN4CCCC4)c(Cl)cc3Cl)nc(N)nc2s1]
g) BIIB021:
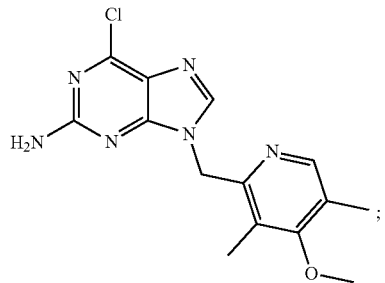 [SMILES: COc1c(C)cnc(Cn2cnc3c(Cl)nc(N)nc32)c1C]
h) PF-04929113 (SNX-5422):
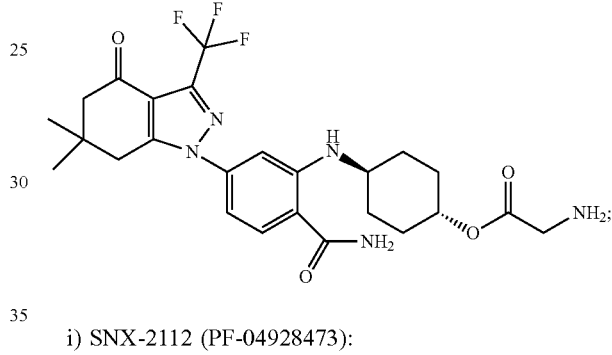
i) SNX-2112 (PF-04928473):
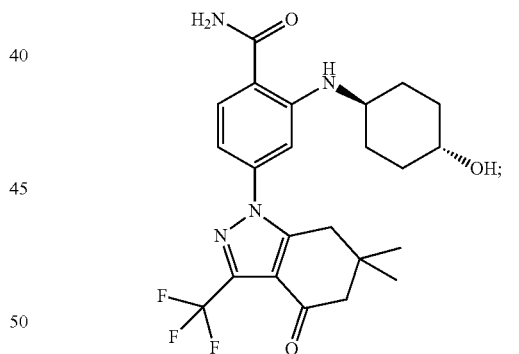
j) KW-2478:
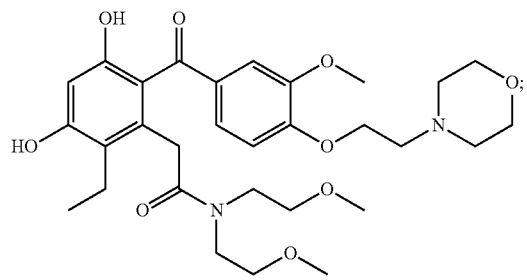 [SMILES: CCc1c(O)cc(O)c(C(=O)c2ccc(OCCN3CCOCC3)c(OC)c2)c1CC(=O)N(CCOC)CCOC]

k) XL888:
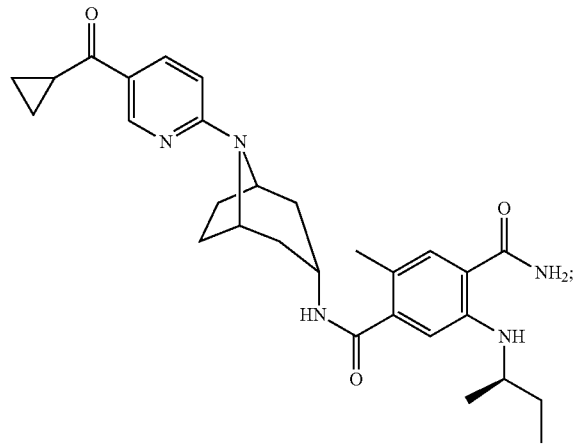 [SMILES: CC[C@@H](C)Nc1cc(C(=O)NC2CC3CCC(C2)N3c2ccc(C(=O)C3CC3)cn2)c(C)cc1C(N)=O]
n) PE-490:
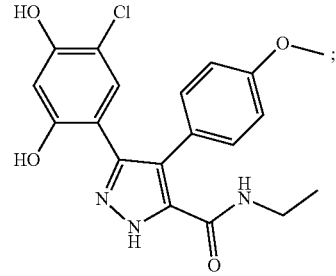 [SMILES: CCNC(=O)c1[nH]nc(-c2cc(Cl)c(O)cc2O)c1-c1ccc(OC)cc1]
o) CH5138303:
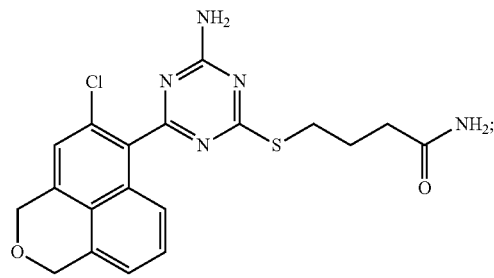 [SMILES: NC(=O)CCCSc1nc(N)nc(-c2c(Cl)cc3c4c(cccc24)COC3)n1]
l) NMS-E973:
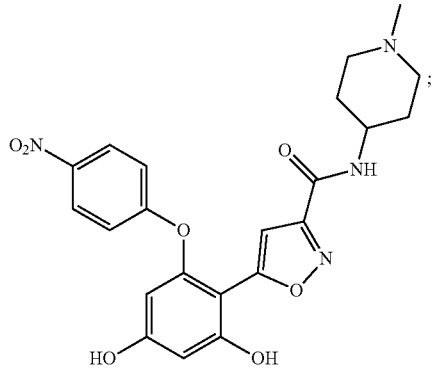
p) VER-50589:
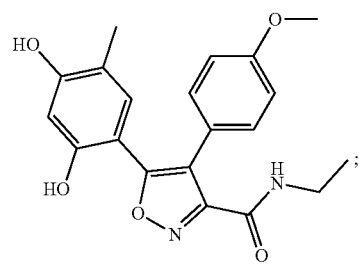 [SMILES: CCNC(=O)c1noc(-c2cc(C)c(O)cc2O)c1-c1ccc(OC)cc1]
m) PU-H71:
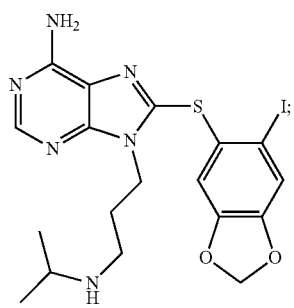
q) VER155008:
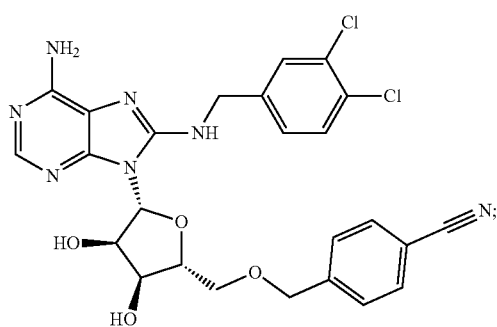 [SMILES: N#Cc1ccc(COC[C@H]2O[C@@H](n3c(NCc4ccc(Cl)c(Cl)c4)nc4c(N)ncnc43)[C@H](O)[C@@H]2O)cc1]

and
r) geldanamycin:

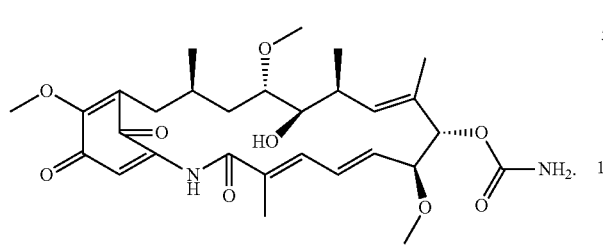

In certain instances, the compound is of Formula HSP-IA1:

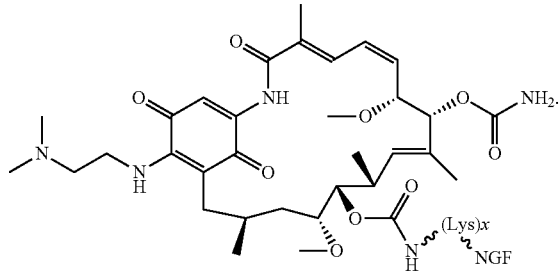

In other instances, the compound is of Formula HSP-IA2:

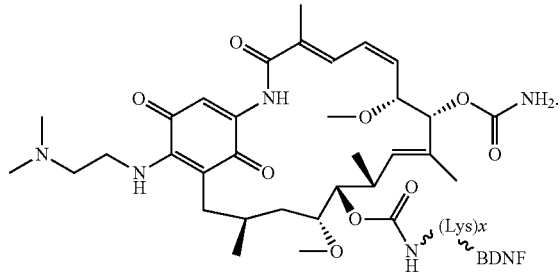

In some embodiments, the anti-cancer agent is a checkpoint inhibitor. In some examples, the checkpoint inhibitor is an inhibitory compound that targets one or more of PD-1, PD-L1, CTLA4, TIM3, LAG3, VISTA, BTLA, TIGIT, LAIR1, CD160, 2B4 and TGFRβ. In some instances, the checkpoint inhibitor is an inhibitory compound that targets PD-1. In some examples, the checkpoint inhibitor is a compound selected from the group consisting of:

a) S7911:

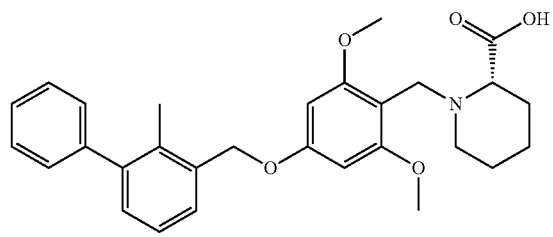 [SMILES: COc1cc(OCc2cccc(-c3ccccc3)c2C)cc(OC)c1CN1CCCC[C@H]1C(=O)O]

b) BMS202:

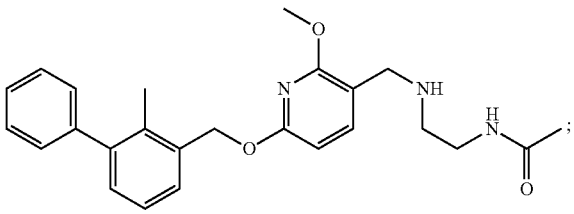

and c) S8158:

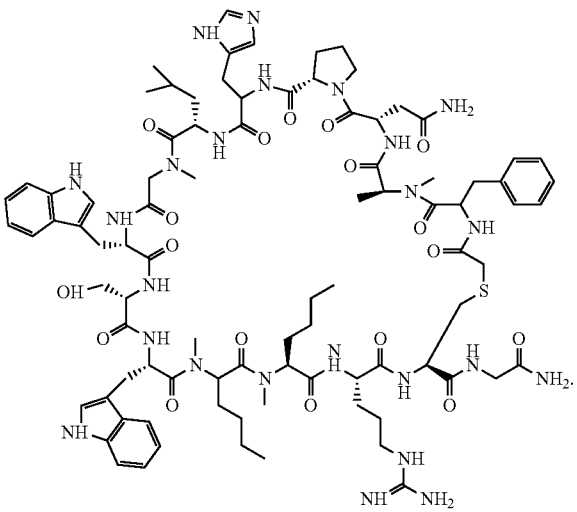 [SMILES: CCCCC1C(=O)N(C)[C@@H](CCCC)C(=O)N[C@@H](CCCNC(=N)N)C(=O)N[C@H](C(=O)NCC(N)=O)CSCC(=O)NC(Cc2ccccc2)C(=O)N(C)[C@@H](C)C(=O)N[C@@H](CC(N)=O)C(=O)N2CCC[C@H]2C(=O)NC(Cc2cnc[nH]2)C(=O)N[C@@H](CC(C)C)C(=O)N(C)CC(=O)N[C@@H](Cc2c[nH]c3ccccc23)C(=O)N[C@@H](CO)C(=O)N[C@@H](Cc2c[nH]c3ccccc23)C(=O)N1C]

In certain instances, the compound is of Formula CP-IA1:

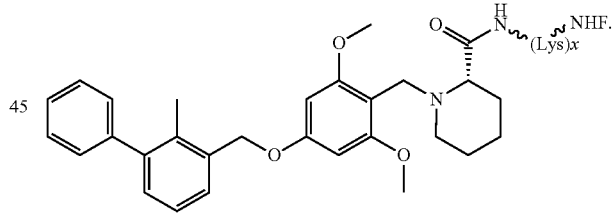

In other instances, the compound is of Formula CP-IA2:

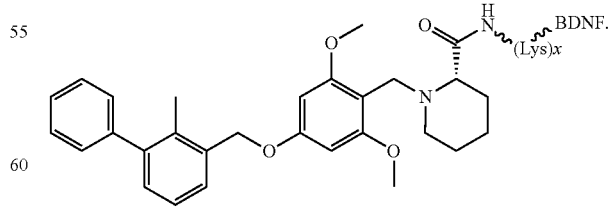

In some embodiments, the anti-cancer agent is a chemokine 4/chemokine ligand 12 CX4/CXCL12) inhibitor. In some examples, the CX4/CXCL12 inhibitor is a compound selected from the group consisting of:

a) burixafor:
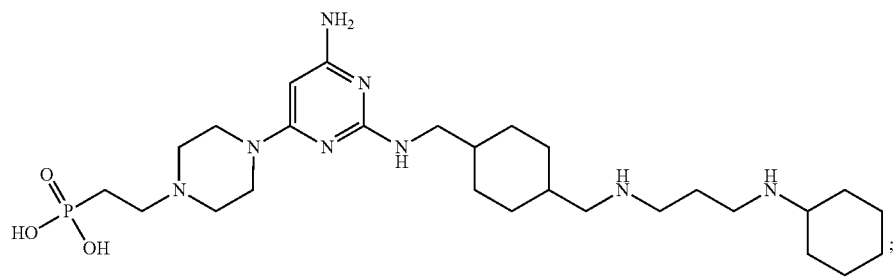 [SMILES: Nc1cc(N2CCN(CCP(=O)(O)O)CC2)nc(NCC2CCC(CNCCCNC3CCCCC3)CC2)n1]
b) LY2510924:
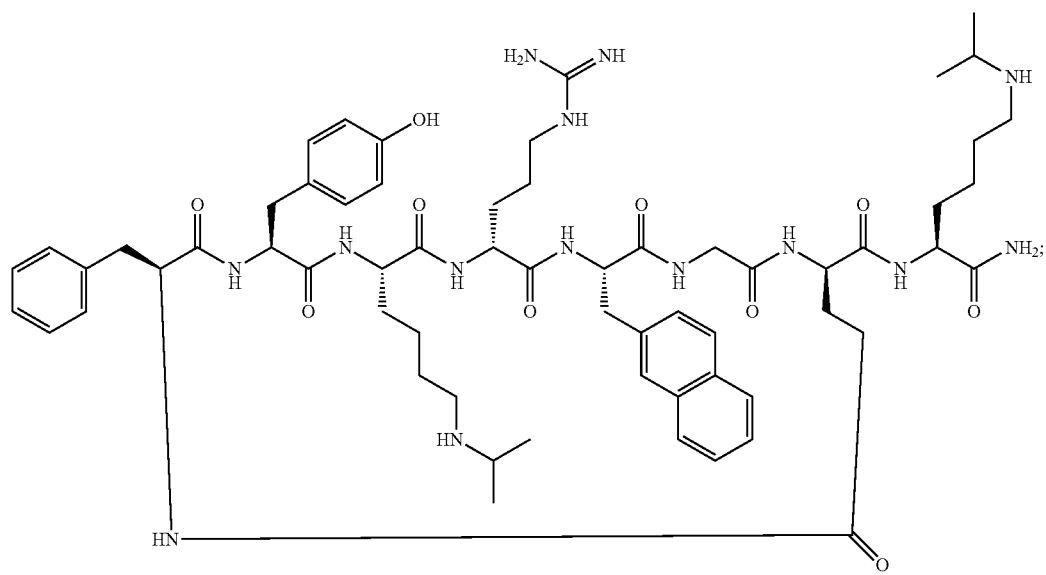 [SMILES: CC(C)NCCCC[C@H](NC(=O)[C@H]1CCC(=O)N[C@@H](Cc2ccccc2)C(=O)N[C@@H](Cc2ccc(O)cc2)C(=O)N[C@@H](CCCCNC(C)C)C(=O)N[C@H](CCCNC(=N)N)C(=O)N[C@@H](Cc2ccc3ccccc3c2)C(=O)NCC(=O)N1)C(N)=O]
c) AMD3100: and
d) AMD3465:
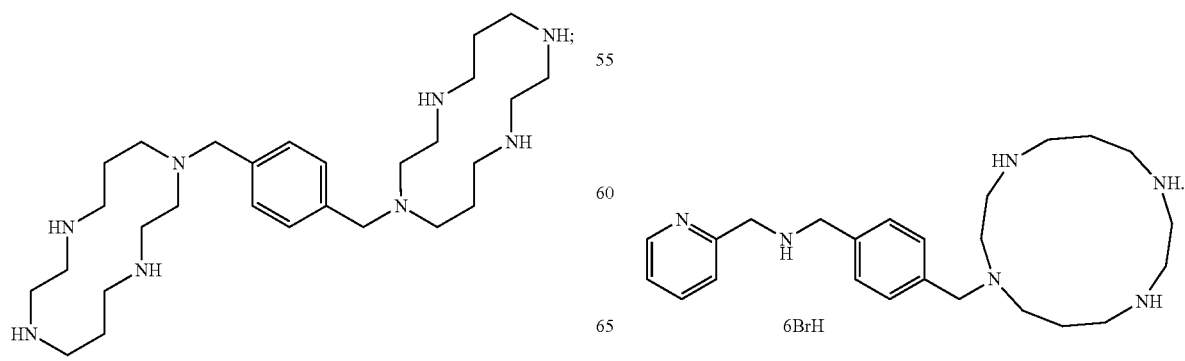
6BrH In certain instances, the compound is of Formula CX-IA1:

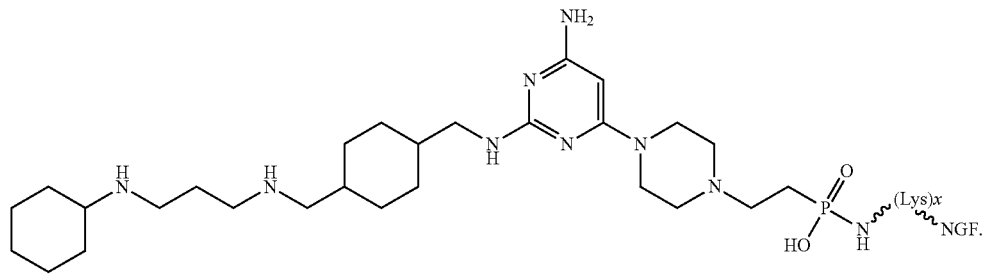

In other instances, the compound is of Formula CX-IA2:

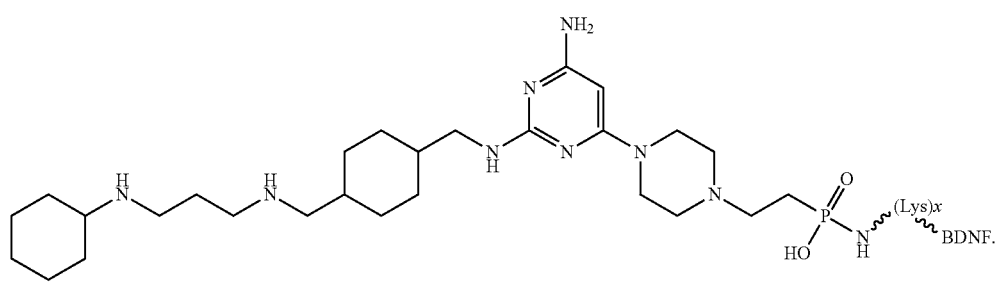

In some embodiments, the compound is an imidazoquinolone amine. In certain instances, the compound is imiquimod:

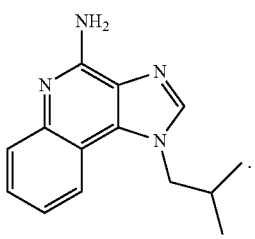 [SMILES: CC(C)Cn1cnc2c(N)nc3ccccc3c21]

In certain embodiments, the cancer is skin cancer. In some instances, the anti-cancer agent is an imidazoquinolone amine. In certain instances, the compound is imiquimod:

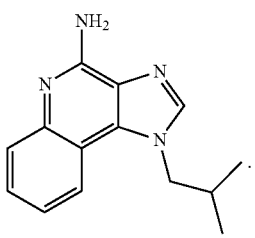 [SMILES: CC(C)Cn1cnc2c(N)nc3ccccc3c21]

In embodiments, the linker may be a cleavable linker or a non-cleavable linker. In some embodiments, the linker is a cleavable linker, such as an acid-cleavable linker, a base-cleavable linker, a photo-cleavable linker or an enzyme-cleavable (e.g., peptidase, esterase) linker. In certain embodiments, the linker includes a carbonate or carbmate moiety. In other embodiments, the linker is a non-cleavable linker. The linker may be a zero-length crosslinker, homo-bifunctional linker, heterobifunctional linker, or a trifunctional crosslinker.

In embodiments, the anti-cancer agent is covalently bonded to a protein, peptide or pepetidomimetic that binds selectively to a neurotrophin receptor. In some embodiments, the protein, peptide or pepetidomimetic is a brain-derived neurotrophic factor (BDNF) or fragment thereof. In some instances, the BDNF or fragment thereof binds to tropomyosin receptor kinase B (trkB), whereafter in certain embodiments it is endocytosed and moved via retrograde axonal transport within the neuron (intraneuronally). In other embodiments, the protein, peptide or pepetidomimetic is a nerve growth factor (NGF) or fragment thereof. In some instances, the NGF or fragment thereof binds to tropomyosin receptor kinase A (trkA). In other instances, the NGF or fragment thereof binds to p75 neurotrophin receptor. In these instances, binding of the NGF or fragment thereof to the receptor triggers internalization of the anti-cancer agent into a cancer cell, such as a glioma cell. In some embodiments, the protein, peptide or peptidomimetic is a ciliary neurotrophic factor (CTNF) or fragment thereof. In other embodiments, the protein, peptide or peptidomimetic is a neurotrophic factor 3 (NT-3) or fragment thereof. In other embodiments, the protein, peptide or peptidomimetic is a glial-cell derived neurotrophic factor (GDNF) or fragment thereof.

Aspects of the present disclosure also include methods for selectively delivering one or more of the subject compounds to a nerve cell. In some embodiments, methods include administering one or more of the subject anti-cancer conjugates to a subject, such as a subject diagnosed as having cancer in need of treatment thereof. In some instances, the subject is diagnosed as having a cancer of the central nervous system, such as a cancer selected from the group consisting of adult and pediatric gliomas, optic pathway glioma, spinal tumors, neurofibromatomas, schwannomas, malignant peripheral nerve sheath tumors, malignant schwannoma, neurofibrosarcoma, and neurosarcoma. In some instances, the subject is diagnosed as having a glioma (low grade, high grade, etc.). In certain instances, the subject is diagnosed as having optic pathway glioma. In certain embodiments, the subject is diagnosed as having perineural invasion. In other embodiments, the subject is diagnosed as having skin cancer. In practicing method according to certain embodiments, one or more of the subject compounds (or a composition having a pharmaceutically acceptable carrier) is administered to the subject to selectively deliver the anti-cancer agent to nerve cells. In some embodiments, the compound is injected. In some instances, the compound is administered intracisternally. In other instances, the compound is administered intrathecally. In still other instances, the compound may be given topically to the eye, as eye drops, or to the skin.

Aspects of the present disclosure also include methods for preparing the subject conjugate compounds. Methods according to certain embodiments include contacting an anti-cancer agent with a bifunctional linker precursor to produce an activated anti-cancer agent; and contacting the activated anti-cancer agent with a protein, peptide or pepetidomimetic that binds selectively to a neurotrophin receptor. In some embodiments, the bifunctional linker precursor is a homobifunctional linker or heterobifunctional linker. In some instances, the bifunctional linker precursor includes succinimide, such as where the bifunctional linker precursor is N,N'-disuccinimidyl carbonate. In some embodiments, to couple the anti-cancer agent to the protein, peptide or pepetidomimetic that binds selectively to the neurotrophin receptor, the anti-cancer agent includes a hydroxyl group and contacting the bifunctional linker precursor includes reacting the bifunctional linker precursor with the hydroxyl group of the anti-cancer agent. In certain instances, methods further include functionalizing the anti-cancer agent with a hydroxyl group. In embodiments, the activated anti-cancer agent reacts with a hydroxyl group, amine group or sulfhydryl group of the protein, peptide or pepetidomimetic. In some embodiments, the activated anti-cancer agent reacts with an amine containing side chain of protein, peptide or pepetidomimetic. In yet other embodiments, the activated anti-cancer agent reacts with a hydroxyl containing side chain of protein, peptide or pepetidomimetic. In still other embodiments, the activated anti-cancer agent reacts with a sulfhydryl containing side chain of protein, peptide or pepetidomimetic.

Select Definitions

The following terms have the following meaning unless otherwise indicated. Any undefined terms have their art recognized meanings.

"Pharmaceutical composition" refers to at least one compound and can further comprise a pharmaceutically acceptable carrier, with which the compound is administered to a patient.

"Pharmaceutically acceptable salt" refers to a salt of a compound, which possesses the desired pharmacological activity of the compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

The term "solvate" as used herein refers to a complex or aggregate formed by one or more molecules of a solute, e.g. a conjugate compound or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

"Pharmaceutically acceptable carrier" refers to a diluent, adjuvant, excipient or vehicle with, or in which a compound is administered.

"Preventing" or "prevention" or "prophylaxis" refers to a reduction in risk of occurrence of a condition, such as pain.

"Treating" or "treatment" of any condition, such as cancer, refers, in certain embodiments, to ameliorating the condition (i.e., arresting or reducing the development of the condition). In certain embodiments "treating" or "treatment" refers to ameliorating at least one physical parameter, which may not be discernible by the patient. In certain embodiments, "treating" or "treatment" refers to inhibiting the condition, either physically, (e.g., stabilization of a discernible symptom), physiologically, (e.g., stabilization of a physical parameter), or both. In certain embodiments, "treating" or "treatment" refers to delaying the onset of the condition.

"Therapeutically effective amount" means the amount of a compound (e.g., conjugate) that, when administered to a patient, is sufficient to effect such treatment. The "therapeutically effective amount" will vary depending on the compound, the condition and its severity and the age, weight, etc., of the patient.

DETAILED DESCRIPTION

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It should be understood that as used herein, the term "a" entity or "an" entity refers to one or more of that entity. For example, a compound refers to one or more compounds. As such, the terms "a", "an", "one or more", and "at least one" can be used interchangeably. Similarly the terms "comprising", "including" and "having" can be used interchangeably.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. When possible, this nomenclature has generally been derived using the commercially-available AutoNom software (MDL, San Leandro, Calif.).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as high performance liquid chromatography (HPLC), preparative thin layer chromatography, flash column chromatography, and ion exchange chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the compounds of the present disclosure, it may be necessary and/or desirable to protect sensitive or reactive groups on any of the molecules concerned. This can be achieved by means of conventional protecting groups as described in standard works, such as T. W. Greene and P. G. M. Wuts, "Protective Groups in Organic Synthesis", Fourth edition, Wiley, New York 2006. The protecting groups can be removed at a convenient subsequent stage using methods known from the art.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^{2}H$, $^{3}H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

Representative Embodiments

Reference will now be made in detail to various embodiments. It will be understood that the invention is not limited to these embodiments. To the contrary, it is intended to cover alternatives, modifications, and equivalents as may be included within the spirit and scope of the allowed claims.

The present disclosure provides conjugate compounds, pharmaceutical compositions, and their methods of use and methods for making, where the conjugate compounds include a protein, peptide or pepetidomimetic that binds selectively to a neurotrophin receptor, an anti-cancer agent and a linker which covalently bonds the anti-cancer agent to the protein, peptide or peptidomimetic. The disclosure provides pharmaceutical compositions which include one or more of the subject conjugate compounds and a pharmaceutically acceptable carrier. Methods for using the conjugate compounds to selectively bind and deliver an anticancer agent to a nerve cell are also provided. Methods for making the conjugate compounds are also described below.

Conjugates for Delivering an Anti-Cancer Agent to Nerve Cells

As summarized above, aspects of the present disclosure include conjugate compounds for delivering an anti-cancer agent to nerve cells. Conjugate compounds according to certain embodiments include a compound having a protein, peptide or pepetidomimetic that binds selectively to a neurotrophin receptor, an anti-cancer agent and a linker that covalently bonds the anti-cancer agent to the protein, peptide or pepetidomimetic binds selectively to the neurotrophin receptor. In certain embodiments, compounds of interest include conjugates of formula I:

B-L-X (I)

wherein:
B is a protein, peptide or pepetidomimetic that binds selectively to a neurotrophin receptor;
L is a linker; and
X is an anti-cancer agent.

In some embodiments, conjugate compounds of interest include an anti-cancer agent. In some instances, the cancer agent is configured to impart a therapeutic effect by internalization into a cancer cell. In some instances, the cancer is a cancer of the central nervous system, such as a cancer selected from the group consisting of adult and pediatric gliomas (low grade glioma or a high grade glioma), optic pathway glioma, spinal tumors, neurofibromatomas, schwannomas, malignant peripheral nerve sheath tumors, malignant schwannoma, neurofibrosarcoma, and neurosarcoma. In certain instances, the cancer is optic pathway glioma.

The anti-cancer agent may vary depending on the desired therapeutic effect and target indication and may be a mammalian target of rapamycin (mTOR) inhibitor or mitogen-activated protein kinase (MEK) inhibitor. In some embodiments, the anti-cancer agent is an mTOR inhibitor. For example, the anti-cancer agent may be sirolimus, temsiorolimus, everolimus and ridaforolimus or a combination thereof. In some instances, the anti-cancer agent is everolimus. In some instances, the compound is of Formula IA1 or Formula IA2:

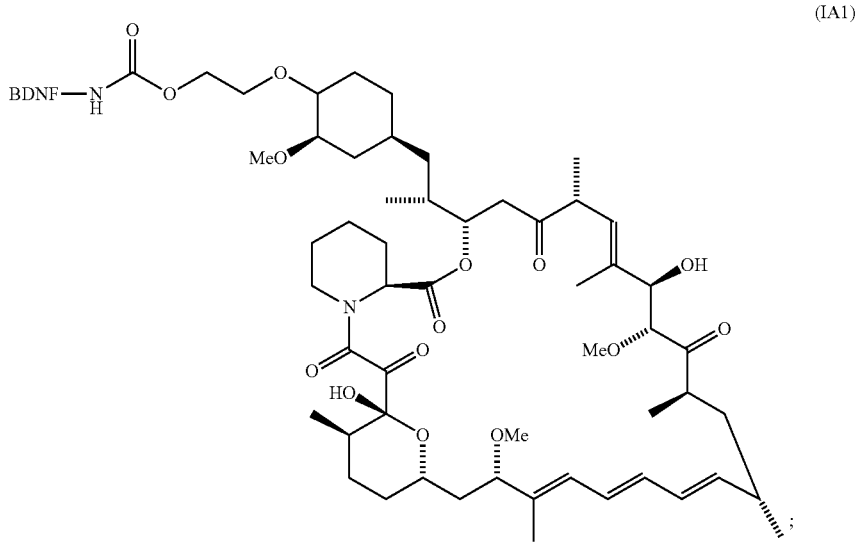

(IA1)

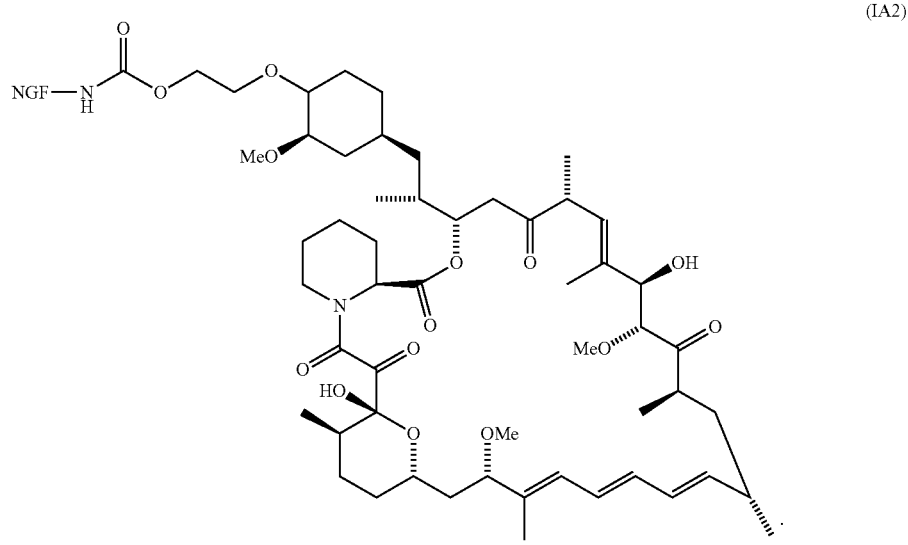

(IA2)

In other embodiments, the anti-cancer agent is an MEK inhibitor. For example, the anti-cancer agent may be trametinib, dabrafenib, cobimetinib, vemurafenib, binimetinib, selumetinib, or a combination thereof. In some instances, the anti-cancer agent is selumetinib. In certain instances, the compound is of Formula IB1 or Formula IB2:

(IB1)

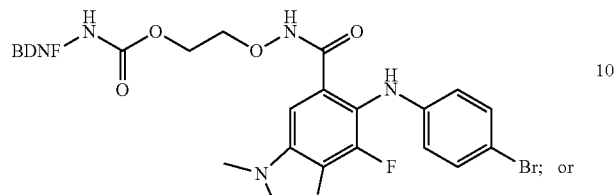

or (IB2)

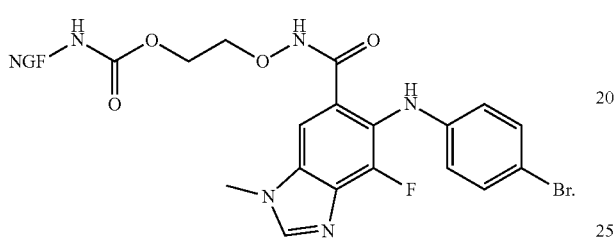

In certain embodiments, the cancer comprises perineural invasion. In some embodiments, the anti-cancer agent is a heat shock protein 90 (hsp90) inhibitor. In some examples, the hsp90 inhibitor is a compound selected from the group consisting of:

a) alvespinomycin:

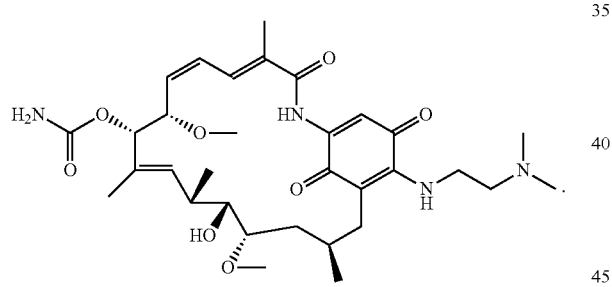

b) 17-N-Allylamino-17-demethoxygeldanamycin (17AAG):

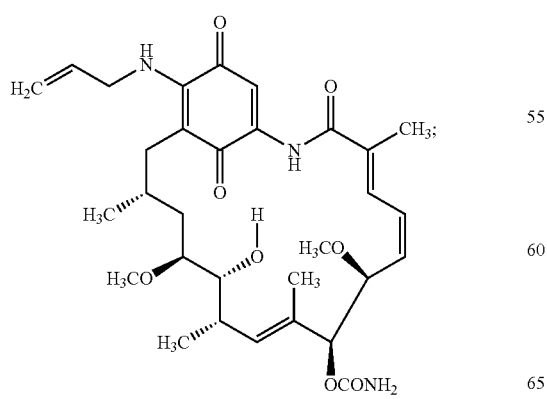

c) luminespib (AUY-922, NVP-AUY922):

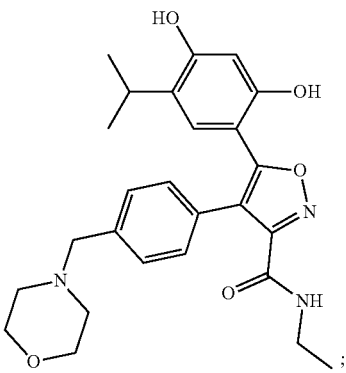 [SMILES: CCNC(=O)c1noc(-c2cc(C(C)C)c(O)cc2O)c1-c1ccc(CN2CCOCC2)cc1]

d) ganetespib (STA-9090):

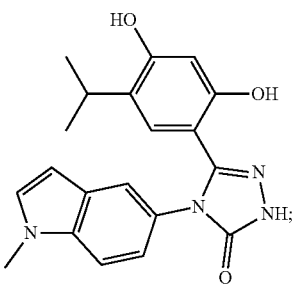 [SMILES: CC(C)c1cc(-c2n[nH]c(=O)n2-c2ccc3c(ccn3C)c2)c(O)cc1O]

e) onalespib (AT13387):

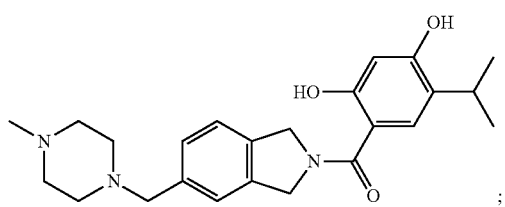 [SMILES: CC(C)c1cc(C(=O)N2Cc3ccc(CN4CCN(C)CC4)cc3C2)c(O)cc1O]

f) NVP-BEP800:

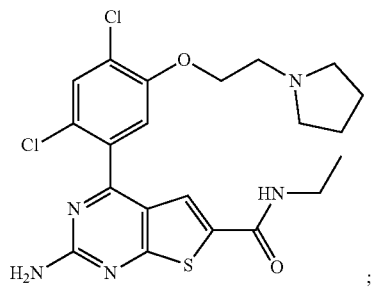 [SMILES: CCNC(=O)c1cc2c(-c3cc(OCCN4CCCC4)c(Cl)cc3Cl)nc(N)nc2s1]

g) BIIB021:
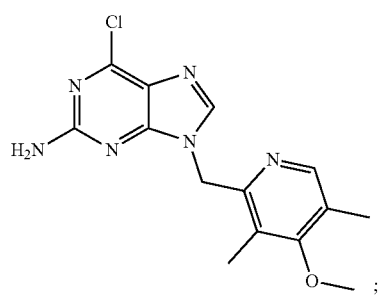 [SMILES: COc1c(C)cnc(Cn2cnc3c(Cl)nc(N)nc32)c1C]
h) PF-04929113 (SNX-5422):
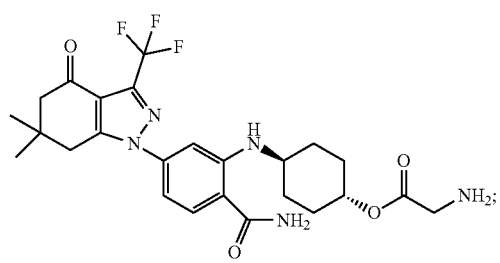 [SMILES: CC1(C)CC(=O)c2c(C(F)(F)F)nn(-c3ccc(C(N)=O)c(N[C@H]4CC[C@H](OC(=O)CN)CC4)c3)c2C1]
i) SNX-2112 (PF-04928473):
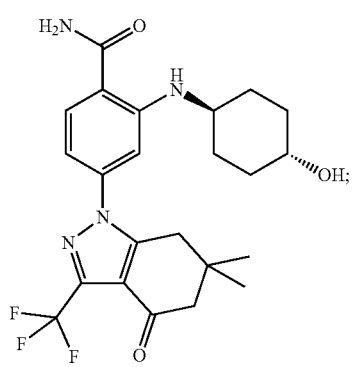
j) KW-2478:
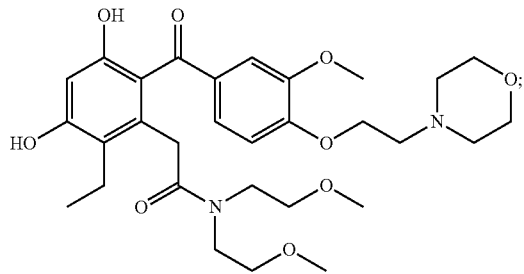 [SMILES: CCc1c(O)cc(O)c(C(=O)c2ccc(OCCN3CCOCC3)c(OC)c2)c1CC(=O)N(CCOC)CCOC]
k) XL888:
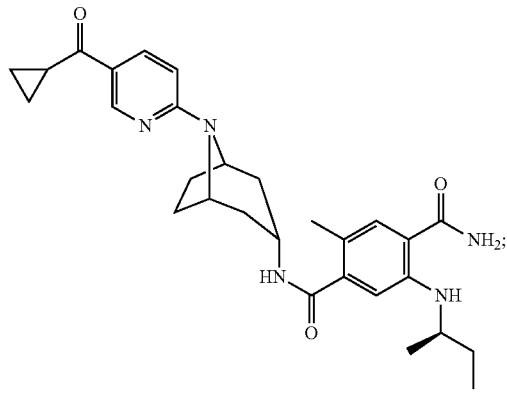 [SMILES: CC[C@@H](C)Nc1cc(C(=O)NC2CC3CCC(C2)N3c2ccc(C(=O)C3CC3)cn2)c(C)cc1C(N)=O]
l) NMS-E973:
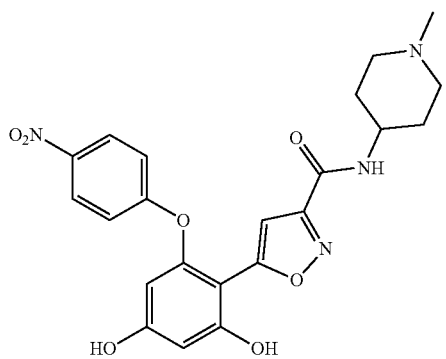
m) PU-H71:
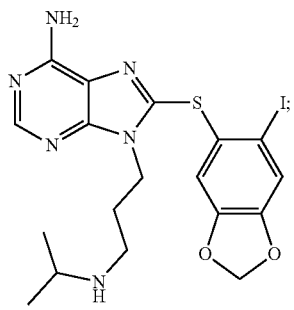
n) VER-49009:
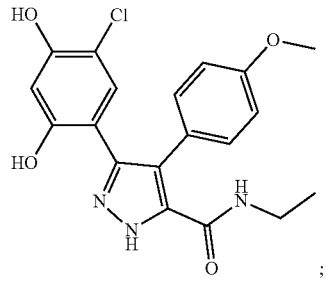 [SMILES: CCNC(=O)c1[nH]nc(-c2cc(Cl)c(O)cc2O)c1-c1ccc(OC)cc1]

o) CH5138303:

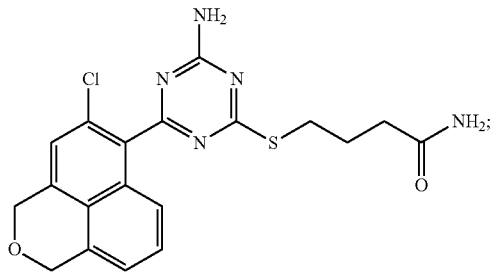 [SMILES: NC(=O)CCCSc1nc(N)nc(-c2c(Cl)cc3c4c(cccc24)COC3)n1]

p) VER-50589:

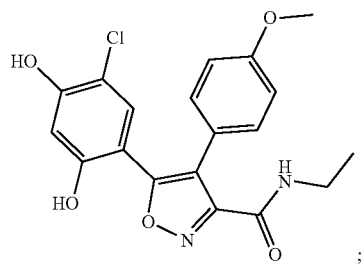 [SMILES: CCNC(=O)c1noc(-c2cc(Cl)c(O)cc2O)c1-c1ccc(OC)cc1]

q) VER155008:

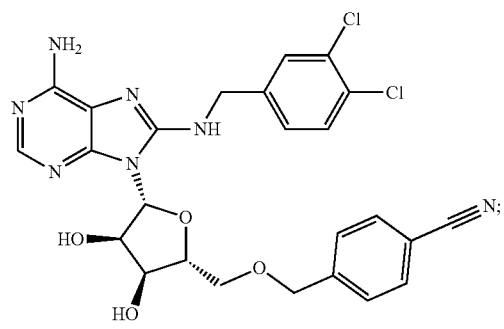 [SMILES: N#Cc1ccc(COC[C@H]2O[C@@H](n3c(NCc4ccc(Cl)c(Cl)c4)nc4c(N)ncnc43)[C@H](O)[C@@H]2O)cc1]

and
r) geldanamycin:

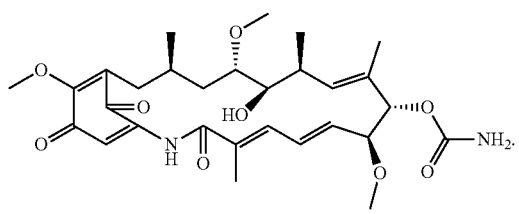 [SMILES: COC1=C2C[C@@H](C)C[C@H](OC)[C@H](O)[C@@H](C)/C=C(\C)[C@H](OC(N)=O)[C@@H](OC)/C=C/C=C(\C)C(=O)NC(=CC1=O)C2=O]

In certain instances, the compound is of Formula HSP-IA1:

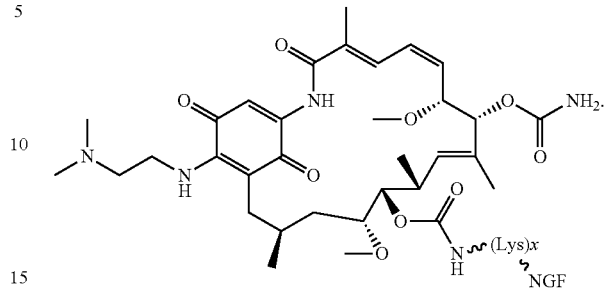

In other instances, the compound is of Formula HSP-IA2:

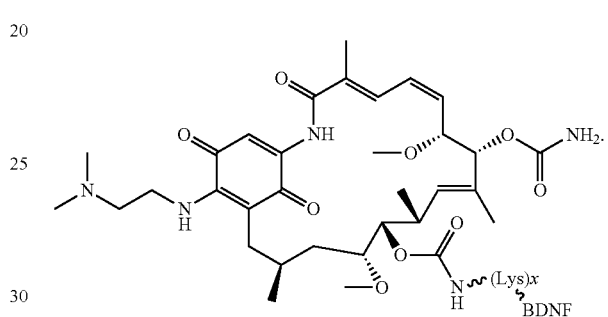

In some embodiments, the anti-cancer agent is a checkpoint inhibitor. In some examples, the is an inhibitory compound that targets one or more of PD-1, PD-L1, CTLA4, TIM3, LAG3, VISTA, BTLA, TIGIT, LAIR1, CD160, 2B4 and TGFRβ. In some instances, the checkpoint inhibitor is an inhibitory compound that targets PD-1. In some examples, the checkpoint inhibitor is a compound selected from the group consisting of:

a) S7911:

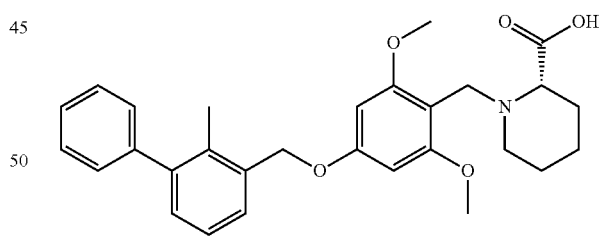

b) BMS202:

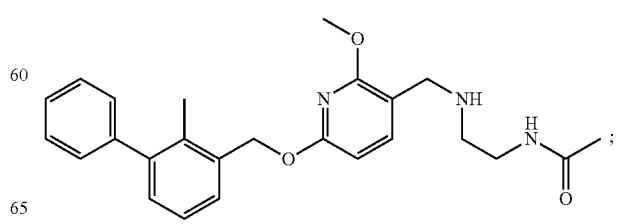

and
c) S8158:
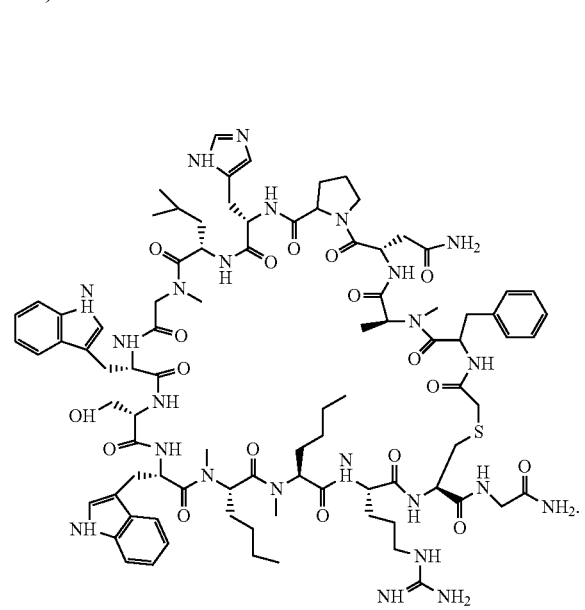
In certain instances, the compound is of Formula CP-IA1:
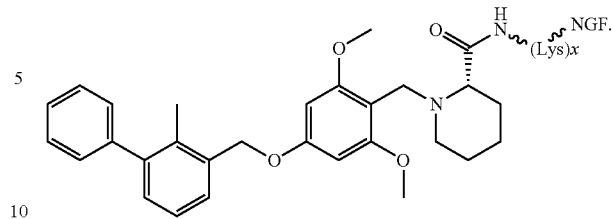
In other instances, the compound is of Formula CP-IA2:
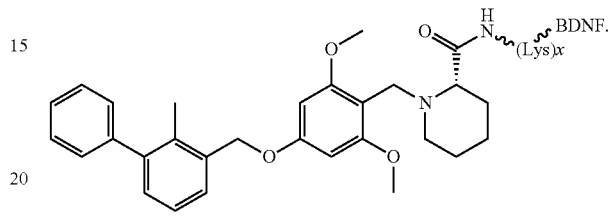
In some embodiment, the anti-cancer agent is a chemokine 4/chemokine ligand 12 (CX4/CXCL12) inhibitor. In some examples, the CX4/CXCK12 inhibitor is a compound selected from the group consisting of:
a) burixafor:
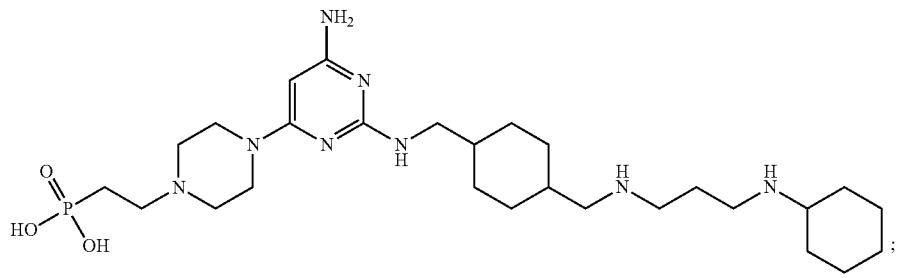 [SMILES: Nc1cc(N2CCN(CCP(=O)(O)O)CC2)nc(NCC2CCC(CNCCCNC3CCCCC3)CC2)n1]
b) LY2510924:
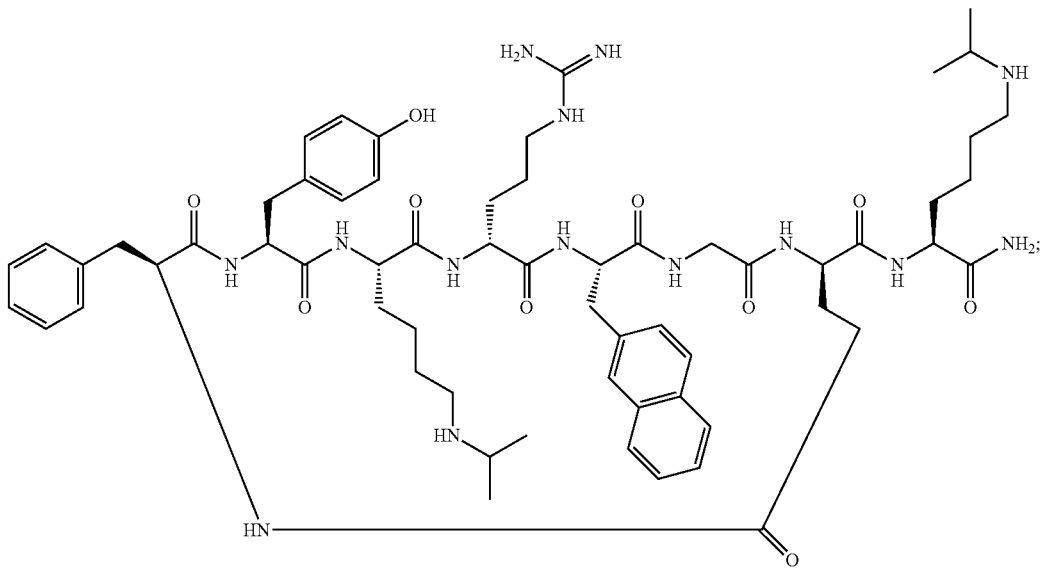 [SMILES: CC(C)NCCCC[C@H](NC(=O)[C@H]1CCC(=O)N[C@@H](Cc2ccccc2)C(=O)N[C@@H](Cc2ccc(O)cc2)C(=O)N[C@@H](CCCCNC(C)C)C(=O)N[C@H](CCCNC(=N)N)C(=O)N[C@@H](Cc2ccc3ccccc3c2)C(=O)NCC(=O)N1)C(N)=O]

c) AMD3100:
and
d) AMD3465:
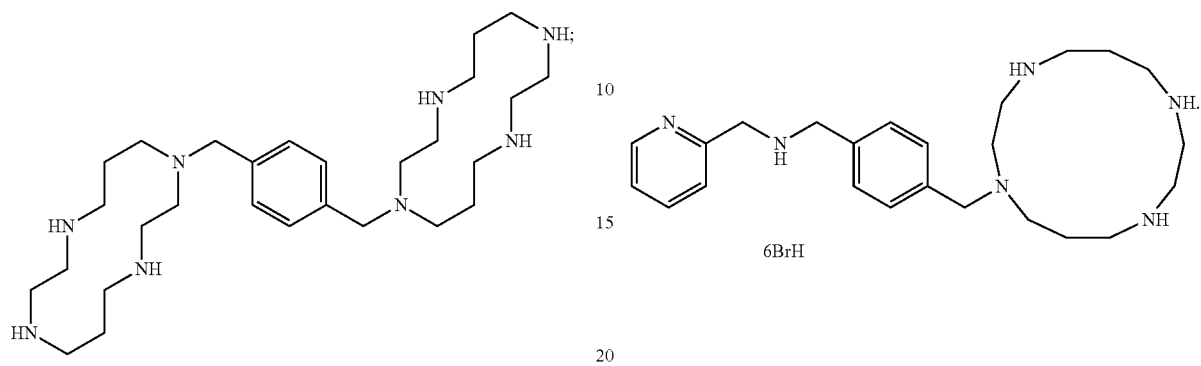
In certain instances, the compound is of Formula CX-IA1:
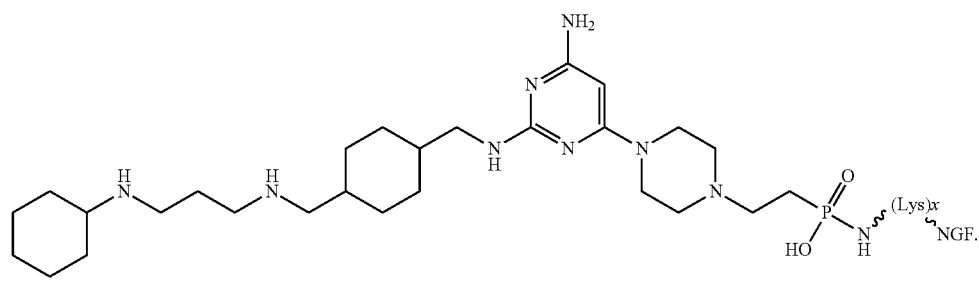
In other instances, the compound is of Formula CX-IA2:
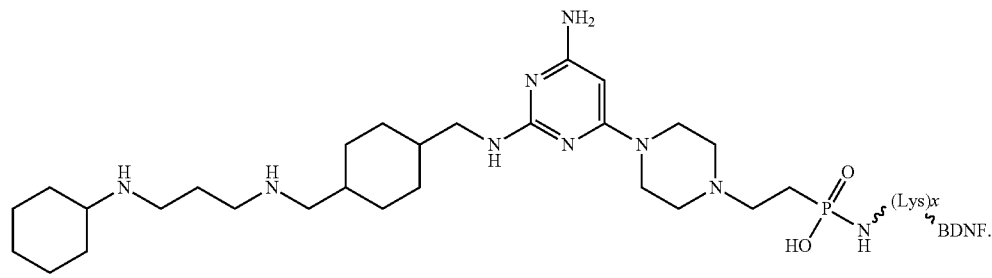

In some embodiments, the compound is an imidazoquinolone amine. In certain instances, the compound is imiquimod:

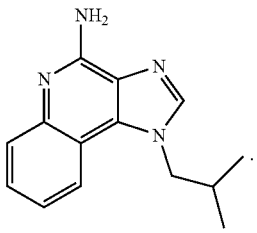 [SMILES: CC(C)Cn1cnc2c(N)nc3ccccc3c21]

In certain embodiments, the cancer is skin cancer. In some instances, the anti-cancer agent is an imidazoquinolone amine. In certain instances, the compound is imiquimod:

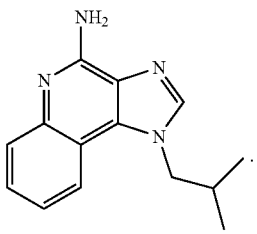 [SMILES: CC(C)Cn1cnc2c(N)nc3ccccc3c21]

In embodiments, conjugate compounds of interest also include a binding moiety which selectively binds to receptors on nerve cells. The binding moiety may include, but are not limited to, nucleic acid sequences, proteins, peptides, peptidomimetics, antibodies, and antibody fragments. In certain embodiments, the binding moiety is a protein, peptides or a peptidomimetic. In some embodiments, the protein, peptide or pepetidomimetic is a brain-derived neurotrophic factor (BDNF) or fragment thereof. In some instances, the BDNF or fragment thereof binds to tropomyosin receptor kinase B (trkB). In other embodiments, the protein, peptide or pepetidomimetic is a nerve growth factor (NGF) or fragment thereof. In some instances, the NGF or fragment thereof binds to tropomyosin receptor kinase A (trkA). In other instances, the NGF or fragment thereof binds to p75 neurotrophin receptor. In these instances, binding of the NGF or fragment thereof to the receptor triggers internalization of the anti-cancer agent into a cancer cell, such as a glioma cell. In some embodiments, the protein, peptide or peptidomimetic is a ciliary neurotrophic factor (CTNF) or fragment thereof. In other embodiments, the protein, peptide or peptidomimetic is a neurotrophic factor 3 (NT-3) or fragment thereof. In other embodiments, the protein, peptide or peptidomimetic is a glial-cell derived neurotrophic factor (GDNF) or fragment thereof. In some instances, the inhibitors of glial cell-derived neurotrophic factor (GDNF) and its high affinity receptor GDNFR-α. The glial cell-derived neurotrophin factor (GDNF) family includes neurturin (NTN), artemin (ART), and persephin (PSP) "have seven conserved cysteine residues with similar spacing, making them distant members of the transforming growth factor-beta (TGF-beta) superfamily". Like TrkA for NGF, the high affinity receptor GDNFR-α binds selectively to GDNF. It mediates activation of the co-receptor Ret protein-tyrosine kinase (PTK), which activates signaling of GDNF and neurturin. GDNF shares binding to the low-affinity receptor p75 with other neurotrophins, including NGF.

In some instances, peptides of interest include, but are not limited to, neurotrophins such as NGF, BDNF, NT-3, NT-4, NT-6; derivatives, analogs, and fragments of neurotrophins such as recombinant molecules of NGF and BDNF as well as synthetic peptides that bind to nerve cell surface receptors and have agonist or antagonist activities of nerve growth factors. In other embodiments, the binding moiety of the subject conjugate compounds include an antibody or antibody fragment, such as an anti-human trkA monoclonal antibody 5C3 or anti-human p75 monoclonal antibody MC192.

The anti-cancer agent is conjugated to the binding moiety that selectively binds to the nerve cell (e.g., neurotrophin receptor) through a linker. The linker may be any convenient covalent linking protocol, such as a zero-length crosslinker, homobifunctional linker, heterobifunctional linker or a trifunctional crosslinker. The linker may include one or more functional groups, such as an amide, alkylamine, carbamate, carbonate, thioether, alkyl, cycloalkyl or aryl moiety, as desired. In some embodiments, the linker includes a carbamate moiety.

In some embodiments, the linker is cleavable. The term "cleavable" is used herein in its conventional sense to refer to linkers that can be cleaved under predetermined conditions so as to break the bond between the anti-cancer agent and the binding moiety. For example, the linker may be an acid-cleavable linker, a base-cleavable linker, a photo-cleavable linker or an enzyme-cleavable (e.g., peptidase, esterase) linker. Acid-cleavable linkers are cleaved by subjecting the conjugate compound to a pH of 7 or below, such as a pH of 6.5 or below, such as a pH of 6.0 or below, such as a pH of 5.5 or below, such as a pH of 5.0 or below, such as a pH of 4.5 of below, such as a pH of 4.0 or below, such as a pH of 3.5 or below, such as a pH of 3.0 or below, such as a pH of 2.5 or below, such a pH of 2.0 or below, such as a pH of 1.5 or below and including a pH of 1.0 or below. Base-cleavable linkers are cleaved by subjecting the conjugate compound to a pH of 7 or above, such as a pH of 7.5 or above, such as a pH of 8.0 or above, such as a pH of 8.5 or above, such as a pH of 9.0 or above, such as a pH of 9.5 or above, such as a pH of 10.0 or above, such as a pH of 10.5 or above, such as a pH of 11.0 or above, such as a pH of 11.5 or above, such as a pH of 12.0 or above, such as a pH of 12.5 or above and including a pH of 13.0 or above.

In certain embodiments, the subject conjugate compounds include an enzyme-cleavable linker. In some instances, the enzyme cleavable linker is cleaved by contacting the compound with a peptidase, such as trypsin or chymotrypsin. In other instances, the enzyme cleavable linker is cleaved by contacting the compound with an esterase. In some embodiments, linkers of interest include those described in U.S. Pat. Nos. 5,767,288; 5,563,250; 5,505,931 and 4,469,774, the disclosures of which are herein incorporated by reference.

In other embodiments, the subject conjugate compounds include a non-cleavable linker. The term "non-cleavable" is used herein in its conventional sense to refer to a covalently bonded moiety that is stable under physiological conditions and does not release the anti-cancer agent from the binding moiety (e.g., the anti-cancer agent remains covalently bonded to the protein, peptide or peptidomimetic that selective binds the nerve cells). In other words, conjugate compounds having non-cleavable linkers are not susceptible to cleavage by acid, base, light or treatment with an enzyme. In these embodiments, 90% or more of conjugate compounds in a composition subjected to treatment by acid, base, light or with an enzyme does not result in release of the anti-cancer agent from the binding moiety (e.g., protein, peptide or peptidomimetic that selective binds the nerve cells), such as 95% or more, such as 97% or more, such as 98% or more, such as 99% or more and including 99.9% or more of the conjugate compounds in a composition subjected to treatment by acid, base, light or with an enzyme does not result in release of the anti-cancer agent from the binding moiety. Examples of suitable non-cleavable linkers may include, but are not limited to, maleimido-containing crosslinkers, such as: N-succinimidyl 4-(maleimidomethyl)cyclohexanecarboxylate (SMCC), N-succinimidyl-4-(N-maleimidomethyl)-cyclohexane-1-carboxy-(6-amidocaproate), κ-maleimidoundecanoic acid N-succinimidyl ester (KMUA), γ-maleimidobutyric acid N-succinimidyl ester (GMBS), F-maleimidocaproic acid N-hydroxysuccinimide ester (EMCS), m-maleimidobenzoyl-N-hydroxysuccinimide ester (MBS), N-(α-maleimidoacetoxy)-succinimide ester [AMAS], succinimidyl-6-(β-maleimidopropionamido) hexanoate (SMPH), N-succinimidyl 4-(p-maleimidophenyl)-butyrate (SMPB), and N-(p-maleimidophenyl)isocyanate (PMPI) or haloacetyl-containing crosslinkers, such as: N-succinimidyl-4-(iodoacetyl)-aminobenzoate (SIAB), N-succinimidyl iodoacetate (SIA), N-succinimidyl bromoacetate (SBA) and N-succinimidyl 3-(bromoacetamido)propionate (SBAP).

Aspects of the present disclosure also include compositions having a pharmaceutically acceptable carrier and one or more of the conjugate compounds described above. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc. For example, the one or more excipients may include sucrose, starch, mannitol, sorbitol, lactose, glucose, cellulose, talc, calcium phosphate or calcium carbonate, a binder (e.g., cellulose, methylcellulose, hydroxymethylcellulose, polypropylpyrrolidone, polyvinylpyrrolidone, gelatin, gum arabic, poly(ethylene glycol), sucrose or starch), a disintegrator (e.g., starch, carboxymethylcellulose, hydroxypropyl starch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol).

The conjugate compounds may be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. In certain embodiments, the conjugate compounds are formulated for injection. For example, compositions of interest may be formulated for intracisternal or intrathecal administration.

In pharmaceutical dosage forms, the conjugate compounds may be administered in the form of its pharmaceutically acceptable salts, or it may also be used alone or in appropriate association, as well as in combination, with other pharmaceutically active compounds. The following methods and excipients are merely exemplary and are in no way limiting.

In some embodiments, compositions of interest include an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. In some instances, compositions of interest further include a preservative. Suitable preservatives include, but are not limited to, a benzyl alcohol, phenol, chlorobutanol, benzalkonium chloride, and the like. In many cases, the composition is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures.

In some embodiments, compositions include other additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Where the composition is formulated for injection, the conjugate compounds may be formulated by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Although the dosage used (as described in greater detail below) in treating a subject will vary depending on the clinical goals to be achieved, a suitable dosage range of the conjugate compound is one which provides up to about 0.0001 mg to about 5000 mg, e.g., from about 1 mg to about 25 mg, from about 25 mg to about 50 mg, from about 50 mg to about 100 mg, from about 100 mg to about 200 mg, from about 200 mg to about 250 mg, from about 250 mg to about 500 mg, from about 500 mg to about 1000 mg, or from about 1000 mg to about 5000 mg of an active agent, which can be administered in a single dose. Those of skill will readily appreciate that dose levels can vary as a function of the specific compound, the severity of the symptoms and the susceptibility of the subject to side effects.

In some embodiments, a suitable dose of a the conjugate compound of Formula I is in the range of from about 1 mg/kg body weight to about 500 mg/kg body weight, e.g., from about 5 mg/kg body weight to about 500 mg/kg body weight, from about 10 mg/kg body weight to about 500 mg/kg body weight, from about 20 mg/kg body weight to about 500 mg/kg body weight, from about 30 mg/kg body weight to about 500 mg/kg body weight, from about 40 mg/kg body weight to about 500 mg/kg body weight, from about 50 mg/kg body weight to about 500 mg/kg body weight, from about 60 mg/kg body weight to about 500 mg/kg body weight, from about 70 mg/kg body weight to about 500 mg/kg body weight, from about 80 mg/kg body weight to about 500 mg/kg body weight, from about 90 mg/kg body weight to about 500 mg/kg body weight, from about 100 mg/kg body weight to about 500 mg/kg body weight, from about 200 mg/kg body weight to about 500 mg/kg body weight, from about 300 mg/kg body weight to about 500 mg/kg body weight, or from about 400 mg/kg body weight to about 500 mg/kg body weight.

In some embodiments, a suitable dose of a compound of Formula I, is in the range of from about 1 mg/kg body weight to about 5 mg/kg body weight, from about 5 mg/kg body weight to about 10 mg/kg body weight, from about 10 mg/kg body weight to about 20 mg/kg body weight, from about 20 mg/kg body weight to about 30 mg/kg body weight, from about 30 mg/kg body weight to about 40 mg/kg body weight, from about 40 mg/kg body weight to about 50 mg/kg body weight, from about 50 mg/kg body weight to about 100 mg/kg body weight, or from about 100 mg/kg body weight to about 500 mg/kg body weight.

In some embodiments, a single dose of the conjugate compound is administered. In other embodiments, multiple doses of the conjugate compound are administered. Where multiple doses are administered over a period of time, the conjugate compound is administered, e.g., twice daily (qid), daily (qd), every other day (qod), every third day, three times per week (tiw), or twice per week (biw) over a period of time. For example, the conjugate compound is administered qid, qd, qod, tiw, or biw over a period of from one day to about 2 years or more. For example, the conjugate compound is administered at any of the aforementioned frequencies for one week, two weeks, one month, two months, six months, one year, or two years, or more, depending on various factors.

Dose units of the present disclosure can be made using manufacturing methods available in the art and can be of a variety of forms suitable for injection (including topical, intracisternal, intrathecal, intravenous, intramuscular, subcutaneous and dermal) administration, for example as a solution, suspension, solution, lyophilate or emulsion. The dose unit can contain components conventional in pharmaceutical preparations, e.g. one or more carriers, binders, lubricants, excipients (e.g., to impart controlled release characteristics), pH modifiers, coloring agents or further active agents.

Dose units provided as liquid dose units can have a total weight of from about 1 microgram to about 1 gram, and can be from about 5 micrograms to 1.5 grams, from about 50 micrograms to 1 gram, from about 100 micrograms to 1 gram, from 50 micrograms to 750 milligrams, and may be from about 1 microgram to 2 grams.

Dose units can comprise components in any relative amounts. For example, dose units can be from about 0.1% to 99% by weight of active ingredients (i.e., conjugate compound) per total weight of dose unit. In some embodiments, dose units can be from 10% to 50%, from 20% to 40%, or about 30% by weight of active ingredients per total weight dose unit.

Dose units can be provided in a variety of different forms and optionally provided in a manner suitable for storage. For example, dose units can be disposed within a container suitable for containing a pharmaceutical composition. The container can be, for example, a bottle (e.g., with a closure device, such as a cap, a vial, an ampule (for single dose units), a dropper, thin film, a tube and the like.

Containers can include a cap (e.g., screw cap) that is removably connected to the container over an opening through which the dose units disposed within the container can be accessed.

Containers can include a seal which can serve as a tamper-evident and/or tamper-resistant element, which seal is disrupted upon access to a dose unit disposed within the container. Such seal elements can be, for example, a frangible element that is broken or otherwise modified upon access to a dose unit disposed within the container. Examples of such frangible seal elements include a seal positioned over a container opening such that access to a dose unit within the container requires disruption of the seal (e.g., by peeling and/or piercing the seal). Examples of frangible seal elements include a frangible ring disposed around a container opening and in connection with a cap such that the ring is broken upon opening of the cap to access the dose units in the container.

Liquid dose units can be placed in a container (e.g., bottle or ampule) of a size and configuration adapted to maintain stability of dose units over a period during which the dose units are dispensed into a prescription. For example, containers can be sized and configured to contain 10, 20, 30, 40, 50, 60, 70, 80, 90, 100 or more single liquid dose units. The containers can be sealed or resealable. The containers can packaged in a carton (e.g., for shipment from a manufacturer to a pharmacy or other dispensary). Such cartons can be boxes, tubes, or of other configuration, and may be made of any material (e.g., cardboard, plastic, and the like). The packaging system and/or containers disposed therein can have one or more affixed labels (e.g., to provide information such as lot number, dose unit type, manufacturer, and the like).

The container can include a moisture barrier and/or light barrier, e.g., to facilitate maintenance of stability of the active ingredients in the dose units contained therein. The container can be adapted to contain a single dose unit or multiples of a dose unit. The container can include a dispensing control mechanism, such as a lock out mechanism that facilitates maintenance of dosing regimen.

Dose units can be provided in a container in which they are disposed, and may be provided as part of a packaging system (optionally with instructions for use). For example, dose units containing different amounts of the conjugate compounds can be provided in separate containers, which containers can be disposed with in a larger container (e.g., to facilitate protection of dose units for shipment). For example, one or more dose units as described herein can be provided in separate containers, where dose units of different compositions are provided in separate containers, and the separate containers disposed within package for dispensing.

Methods for Delivering an Anti-Cancer Agent to Nerve Cells

As summarized above, aspects of the present disclosure include methods for delivering an anti-cancer agent to a nerve cell. In practicing the subject methods according to certain embodiments, methods include contacting a nerve cell with a compound having a protein, peptide or pepetidomimetic that binds selectively to a neurotrophin receptor of the nerve cell, an anti-cancer agent and a linker that covalently bonds the anti-cancer agent to the protein, peptide or pepetidomimetic. In some embodiments, methods include administering one or more of the subject conjugate compounds to a subject. In describing methods of the present disclosure, the term "subject" is meant the person or organism to which the conjugate compound is administered. As such, subjects of the present disclosure may include but are not limited to mammals, e.g., humans and other primates, such as chimpanzees and other apes and monkey species, dogs, rabbits, cats and other domesticated pets; and the like, where in certain embodiments the subject are humans. The term subject is also meant to include a person or organism of any age, weight or other physical characteristic, where the subjects may be an adult, a child, an infant or a newborn. In certain embodiments, the subject is a child and methods include administering one or more of the conjugate compounds in the treatment of glioma, such as optic pathway glioma.

In some embodiments, methods include diagnosing the subject as having cancer in need of treatment thereof. In some instances, the subject is diagnosed as having a cancer of the central nervous and/or peripheral nervous systems, such as a cancer selected from the group consisting of adult and pediatric gliomas, optic pathway glioma, spinal tumors, neurofibromatomas, schwannomas, malignant peripheral nerve sheath tumors, malignant schwannoma, neurofibrosarcoma, neurosarcoma. In some instances, the subject is diagnosed as having a glioma (low grade, high grade, etc.). In certain instances, the subject is diagnosed as having optic pathway glioma.

In some instances, methods include diagnosing the subject as having a cancer that comprises perineural invasion. The term "perineural invasion" is used herein in its conventional sense to refer to the invasion of malignancy to the area surrounding the nerve. In addition to direct invasion, lymphatic spread, and hematogenic spread, tumors can spread via nerves: perineural tumor growth occurs in pancreatic cancer, in head and neck squamous cell carcinomas (HN-SCCs), solid tumors, and blood cancers when neoplastic cells invade one or several peripheral nerve sheath layers, the epineurium, the perineurium, or endoneurium. Schwann cells, a sublayer of the outermost layer, the epineurium, play a key role in perineural cancer spread by adapting a distinct, de-differentiated phenotype in neoplasms, a phenotype that "crosstalks" with cancer cells. The normal endoneurium comprises mainly of Schwann cells and axons, where both myelinated and non-myelinated axons are associated with Schwann cells.

In some embodiments, perineural tumor growth is characterized as to centripetal (towards the CNS) perineural spread; it is typically observed in larger nerves, where the nerves mainly affected are the facial (CN, cranial nerve VII) and trigeminal, or CN, cranial nerve V, nerves.

In some embodiments, methods include diagnosing the subject as having skin cancer. In embodiments, the cancer may be malignancy of any part of the skin, including one or more of the subcutis, dermis and epidermis, including the stratum corneum, stratum germinativum, stratum spinosum and stratum basale. The skin cancer treated with the subject compounds and compositions described herein may be located at any part of the body, such as for example, the arms, legs, buttocks, abdomen, back, neck, scrotum, vagina, face, behind the ear as well as to the scalp and back of the head.

Compounds as described herein may be administered to a subject by any convenient protocol, including, but not limited, to topically, orally, sublingually, parenterally, intravenously, vaginally, rectally as well as by transdermal protocols. In certain embodiments, the subject conjugate compounds are administered by injection, such as by intracisternal injection or intrathecal injection.

In certain embodiments, protocols may include multiple dosage intervals. By "multiple dosage intervals" is meant that two or more dosages of the conjugate compound composition is administered to the subject in a sequential manner. In practicing methods of the present disclosure, treatment regimens may include two or more dosage intervals, such as three or more dosage intervals, such as four or more dosage intervals, such as five or more dosage intervals, including ten or more dosage intervals.

The duration between dosage intervals in a multiple dosage interval treatment protocol may vary, depending on the physiology of the subject or by the treatment protocol as determined by a health care professional. For example, the duration between dosage intervals in a multiple dosage treatment protocol may be predetermined and follow at regular intervals. As such, the time between dosage intervals may vary and may be 1 day or longer, such as 2 days or longer, such as 4 days or longer, such as 6 days or longer, such as 8 days or longer, such as 12 days or longer, such as 16 days or longer and including 24 days or longer. In certain embodiments, multiple dosage interval protocols provide for a time between dosage intervals of 1 week or longer, such as 2 weeks or longer, such as 3 weeks or longer, such as 4 weeks or longer, such as 5 weeks or longer, including 6 weeks or longer.

In certain embodiments, compositions of the invention can be administered prior to, concurrent with, or subsequent to other therapeutic agents for treating the same or an unrelated condition. If provided at the same time as another therapeutic agent, compositions having the subject conjugate compounds may be administered in the same or in a different composition. Thus, the anti-cancer-neurotrophin binding conjugate compositions of interest and other therapeutic agents can be administered to the subject by way of concurrent therapy. By "concurrent therapy" is intended administration to a subject such that the therapeutic effect of the combination of the substances is caused in the subject undergoing therapy. For example, concurrent therapy may be achieved by administering the anti-cancer—neurotrophin binding conjugate compositions of the invention with a pharmaceutical composition having at least one other agent, such as an anti-inflammatory agent, immunosuppressant, steroid, analgesic, anesthetic, antihypertensive, chemotherapeutic, among other types of therapeutics, which in combination make up a therapeutically effective dose, according to a particular dosing regimen. Administration of the separate pharmaceutical compositions can be performed simultaneously or at different times (i.e., sequentially, in either order, on the same day, or on different days), so long as the therapeutic effect of the combination of these substances is caused in the subject undergoing therapy.

Where the anti-cancer-neurotrophin binding conjugate is administered concurrently with a second therapeutic agent to treat the same condition (e.g., a second chemotherapeutic, the weight ratio of the anti-cancer—neurotrophin binding conjugate to second therapeutic agent may range from 1:2 and 1:2.5; 1:2.5 and 1:3; 1:3 and 1:3.5 1:3.5 and 1:4; 1:4 and 1:4.5; 1:4.5 and 1:5; 1:5 and 1:10; and 1:10 and 1:25 or a range thereof. For example, the weight ratio of the anti-cancer—neurotrophin binding conjugate to second therapeutic agent may range between 1:1 and 1:5; 1:5 and 1:10; 1:10 and 1:15; or 1:15 and 1:25. Alternatively, the weight ratio of the second therapeutic agent to the anti-cancer—neurotrophin binding conjugate ranges between 2:1 and 2.5:1; 2.5:1 and 3:1; 3:1 and 3.5:1; 3.5:1 and 4:1; 4:1 and 4.5:1; 4.5:1 and 5:1; 5:1 and 10:1; and 10:1 and 25:1 or a range thereof. For example, the ratio of the second therapeutic agent the anti-cancer—neurotrophin binding conjugate may range between 1:1 and 5:1; 5:1 and 10:1; 10:1 and 15:1; or 15:1 and 25:1.

Chemotherapeutic Agents and Combination Therapy

As will be readily understood, the methods of treating by administering a therapeutically effective amount of a compound conjugate (i.e., an anti-cancer conjugate of Formula I) to a subject described herein may, in some instances, be combined with one or more conventional treatments. For example, in the case of oncology, the methods described herein may, in some instances, be combined with a conventional cancer therapy including but not limited to e.g., conventional chemotherapy, conventional radiation therapy, conventional immunotherapy, surgery, etc.

In some instances, the methods described herein may be used before or after a conventional therapy. For example, the methods described herein may be used as an adjuvant or neoadjuvant therapy, e.g., after a subject has seen improvement from a conventional therapy, or may be used when a subject has not responded to a conventional therapy. In some instances, the methods described herein may be used prior to an additional therapy, e.g., to prepare a subject for an additional therapy, e.g., a conventional therapy as described herein.

Standard cancer therapies include surgery (e.g., surgical removal of cancerous tissue), radiation therapy, bone marrow transplantation, chemotherapeutic treatment, antibody treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Suitable antibodies for use in cancer treatment include, but are not limited to, naked antibodies, e.g., trastuzumab (Herceptin), bevacizumab (Avastin™), cetuximab (Erbitux™) panitumumab (Vectibix™), Ipilimumab (Yervoy™), rituximab (Rituxan), alemtuzumab (Lemtrada™), Ofatumumab (Arzerra™), Oregovomab (OvaRex™), Lambrolizumab (MK-3475), pertuzumab (Perjeta™), ranibizumab (Lucentis™) etc., andconjugated antibodies, e.g., gemtuzumab ozogamicin (Mylortarg™), Brentuximab vedotin (Adcetris™), 90Y-labelled ibritumomab tiuxetan (Zevalin™), 131I-labelled tositumoma (Bexxar™), etc. Suitable antibodies for use in cancer treatment include, but are not limited to, antibodies raised against tumor-associated antigens. Such antigens include, but are not limited to, CD20, CD30, CD33, CD52, EpCAM, CEA, gpA33, Mucins, TAG-72, CAIX, PSMA, Folate-binding protein, Gangliosides (e.g., GD2, GD3, GM2, etc.), Le y, VEGF, VEGFR, Integrin alpha-V-beta-3, Integrin alpha-5-beta-1, EGFR, ERBB2, ERBB3, MET, IGF1R, EPHA3, TRAILR1, TRAILR2, RANKL, FAP, Tenascin, etc.

Conventional cancer therapies also include targeted therapies for cancer including but not limited to e.g., Ado-trastuzumab emtansine (Kadcyla) targeting HER2 (ERBB2/neu) (approved for use in Breast cancer); Afatinib (Gilotrif) targeting EGFR (HER1/ERBB1), HER2 (ERBB2/neu) (approved for use in Non-small cell lung cancer); Aldesleukin (Proleukin) targeting (approved for use in Renal cell carcinoma, Melanoma); Alectinib (Alecensa) targeting ALK (approved for use in Non-small cell lung cancer); Alemtuzumab (Campath) targeting CD52 (approved for use in B-cell chronic lymphocytic leukemia); Atezolizumab (Tecentriq) targeting PD-L1 (approved for use in Urothelial carcinoma, Non-small cell lung cancer); Avelumab (Bavencio) targeting PD-L1 (approved for use in Merkel cell carcinoma); Axitinib (Inlyta) targeting KIT, PDGFRP, VEGFR1/2/3 (approved for use in Renal cell carcinoma); Belimumab (Benlysta) targeting BAFF (approved for use in Lupus erythematosus); Belinostat (Beleodaq) targeting HDAC (approved for use in Peripheral T-cell lymphoma); Bevacizumab (Avastin) targeting VEGF ligand (approved for use in Cervical cancer, Colorectal cancer, Fallopian tube cancer, Glioblastoma, Non-small cell lung cancer, Ovarian cancer, Peritoneal cancer, Renal cell carcinoma); Blinatumomab (Blincyto) targeting CD19/CD3 (approved for use in Acute lymphoblastic leukemia (precursor B-cell)); Bortezomib (Velcade) targeting Proteasome (approved for use in Multiple myeloma, Mantle cell lymphoma); Bosutinib (Bosulif) targeting ABL (approved for use in Chronic myelogenous leukemia); Brentuximab vedotin (Adcetris) targeting CD30 (approved for use in Hodgkin lymphoma, Anaplastic large cell lymphoma); Brigatinib (Alunbrig) targeting ALK (approved for use in Non-small cell lung cancer (ALK+)); Cabozantinib (Cabometyx, Cometriq) targeting FLT3, KIT, MET, RET, VEGFR2 (approved for use in Medullary thyroid cancer, Renal cell carcinoma); Carfilzomib (Kyprolis) targeting Proteasome (approved for use in Multiple myeloma); Ceritinib (Zykadia) targeting ALK (approved for use in Non-small cell lung cancer); Cetuximab (Erbitux) targeting EGFR (HER1/ERBB1) (approved for use in Colorectal cancer, Squamous cell cancer of the head and neck); Cobimetinib (Cotellic) targeting MEK (approved for use in Melanoma); Crizotinib (Xalkori) targeting ALK, MET, ROS1 (approved for use in Non-small cell lung cancer); Dabrafenib (Tafinlar) targeting BRAF (approved for use in Melanoma, Non-small cell lung cancer); Daratumumab (Darzalex) targeting CD38 (approved for use in Multiple myeloma); Dasatinib (Sprycel) targeting ABL (approved for use in Chronic myelogenous leukemia, Acute lymphoblastic leukemia); Denosumab (Xgeva) targeting RANKL (approved for use in Giant cell tumor of the bone); Dinutuximab (Unituxin) targeting B4GALNT1 (GD2) (approved for use in Pediatric neuroblastoma); Durvalumab (Imfinzi) targeting PD-L1 (approved for use in Urothelial carcinoma); Elotuzumab (Empliciti) targeting SLAMF7 (CS1/CD319/CRACC) (approved for use in Multiple myeloma); Enasidenib (Idhifa) targeting IDH2 (approved for use in Acute myeloid leukemia); Erlotinib (Tarceva) targeting EGFR (HER1/ERBB1) (approved for use in Non-small cell lung cancer, Pancreatic cancer); Everolimus (Afinitor) targeting mTOR (approved for use in Pancreatic, gastrointestinal, or lung origin neuroendocrine tumor, Renal cell carcinoma, Nonresectable subependymal giant cell astrocytoma, Breast cancer); Gefitinib (Iressa) targeting EGFR (HER1/ERBB1) (approved for use in Non-small cell lung cancer); Ibritumomab tiuxetan (Zevalin) targeting CD20 (approved for use in Non-Hodgkin's lymphoma); Ibrutinib (Imbruvica) targeting BTK (approved for use in Mantle cell lymphoma, Chronic lymphocytic leukemia, Waldenstrom's macroglobulinemia); Idelalisib (Zydelig) targeting PI3K6 (approved for use in Chronic lymphocytic leukemia, Follicular B-cell non-Hodgkin lymphoma, Small lymphocytic lymphoma); Imatinib (Gleevec) targeting KIT, PDGFR, ABL (approved for use in GI stromal tumor (KIT+), Dermatofibrosarcoma protuberans, Multiple hematologic malignancies); Ipilimumab (Yervoy) targeting CTLA-4 (approved for use in Melanoma); Ixazomib (Ninlaro) targeting Proteasome (approved for use in Multiple Myeloma); Lapatinib (Tykerb) targeting HER2 (ERBB2/neu), EGFR (HER1/ERBB1) (approved for use in Breast cancer (HER2+)); Lenvatinib (Lenvima) targeting VEGFR2 (approved for use in Renal cell carcinoma, Thyroid cancer); Midostaurin (Rydapt) targeting FLT3 (approved for use in acute myeloid leukemia (FLT3+)); Necitumumab (Portrazza) targeting EGFR (HER1/ERBB1) (approved for use in Squamous non-small cell lung cancer); Neratinib (Nerlynx) targeting HER2 (ERBB2/neu) (approved for use in Breast cancer); Nilotinib (Tasigna) targeting ABL (approved for use in Chronic myelogenous leukemia); Niraparib (Zejula) targeting PARP (approved for use in Ovarian cancer, Fallopian tube cancer, Peritoneal cancer); Nivolumab (Opdivo) targeting PD-1 (approved for use in Colorectal cancer, Head and neck squamous cell carcinoma, Hodgkin lymphoma, Melanoma, Non-small cell lung cancer, Renal cell carcinoma, Urothelial carcinoma); Obinutuzumab (Gazyva) targeting CD20 (approved for use in Chronic lymphocytic leukemia, Follicular lymphoma); Ofatumumab (Arzerra, HuMax-CD20) targeting CD20 (approved for use in Chronic lymphocytic leukemia); Olaparib (Lynparza) targeting PARP (approved for use in Ovarian cancer); Olaratumab (Lartruvo) targeting PDGFRa (approved for use in Soft tissue sarcoma); Osimertinib (Tagrisso) targeting EGFR (approved for use in Non-small cell lung cancer); Palbociclib (Ibrance) targeting CDK4, CDK6 (approved for use in Breast cancer); Panitumumab (Vectibix) targeting EGFR (HER1/ERBB1) (approved for use in Colorectal cancer); Panobinostat (Farydak) targeting HDAC (approved for use in Multiple myeloma); Pazopanib (Votrient) targeting VEGFR, PDGFR, KIT (approved for use in Renal cell carcinoma); Pembrolizumab (Keytruda) targeting PD-1 (approved for use in Classical Hodgkin lymphoma, Melanoma, Non-small cell lung cancer (PD-L1+), Head and neck squamous cell carcinoma, Solid tumors (MSI-H)); Pertuzumab (Perjeta) targeting HER2 (ERBB2/neu) (approved for use in Breast cancer (HER2+)); Ponatinib (Iclusig) targeting ABL, FGFR1-3, FLT3, VEGFR2 (approved for use in Chronic myelogenous leukemia, Acute lymphoblastic leukemia); Ramucirumab (Cyramza) targeting VEGFR2 (approved for use in Colorectal cancer, Gastric cancer or Gastroesophageal junction (GEJ) adenocarcinoma, Non-small cell lung cancer); Regorafenib (Stivarga) targeting KIT, PDGFRP, RAF, RET, VEGFR1/2/3 (approved for use in Colorectal cancer, Gastrointestinal stromal tumors, Hepatocellular carcinoma); Ribociclib (Kisqali) targeting CDK4, CDK6 (approved for use in Breast cancer (HR+, HER2-)); Rituximab (Rituxan, Mabthera) targeting CD20 (approved for use in Non-Hodgkin's lymphoma, Chronic lymphocytic leukemia, Rheumatoid arthritis, Granulomatosis with polyangiitis); Rituximab/hyaluronidase human (Rituxan Hycela) targeting CD20 (approved for use in Chronic lymphocytic leukemia, Diffuse large B-cell lymphoma, Follicular lymphoma); Romidepsin (Istodax) targeting HDAC (approved for use in Cutaneous T-cell lymphoma, Peripheral T-cell lymphoma); Rucaparib (Rubraca) targeting PARP (approved for use in Ovarian cancer); Ruxolitinib (Jakafi) targeting JAK1/2 (approved for use in Myelofibrosis); Siltuximab (Sylvant) targeting IL-6 (approved for use in Multicentric Castleman's disease); Sipuleucel-T (Provenge) targeting (approved for use in Prostate cancer); Sonidegib (Odomzo) targeting Smoothened (approved for use in Basal cell carcinoma); Sorafenib (Nexavar) targeting VEGFR, PDGFR, KIT, RAF (approved for use in Hepatocellular carcinoma, Renal cell carcinoma, Thyroid carcinoma); Temsirolimus (Torisel) targeting mTOR (approved for use in Renal cell carcinoma); Tositumomab (Bexxar) targeting CD20 (approved for use in Non-Hodgkin's lymphoma); Trametinib (Mekinist) targeting MEK (approved for use in Melanoma, Non-small cell lung cancer); Trastuzumab (Herceptin) targeting HER2 (ERBB2/neu) (approved for use in Breast cancer (HER2+), Gastric cancer (HER2+)); Vandetanib (Caprelsa) targeting EGFR (HER1/ERBB1), RET, VEGFR2 (approved for use in Medullary thyroid cancer); Vemurafenib (Zelboraf) targeting BRAF (approved for use in Melanoma); Venetoclax (Venclexta) targeting BCL2 (approved for use in Chronic lymphocytic leukemia); Vismodegib (Erivedge) targeting PTCH, Smoothened (approved for use in Basal cell carcinoma); Vorinostat (Zolinza) targeting HDAC (approved for use in Cutaneous T-cell lymphoma); Ziv-aflibercept (Zaltrap) targeting PIGF, VEGFA/B (approved for use in Colorectal cancer); and the like.

Biological response modifiers suitable for use in connection with the methods of the present disclosure include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-$\alpha$; (7) interferon-$\gamma$; (8) colony-stimulating factors; (9) inhibitors of angiogenesis; and (10) antagonists of tumor necrosis factor.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (*vinca*) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CY-TOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

In some instances, methods of treating a subject for cancer may further include administering an agent which enhances the activity of the treatment. Such agents that enhance the activity of the treatment will vary widely and may include but are not limited to e.g., agents that inhibit an inhibitor molecule. Suitable inhibitory molecules that may be targeted include but are not limited to e.g., PD1, PD-L1, CTLA4, TIM3, LAG3, VISTA, BTLA, TIGIT, LAIR1, CD160, 2B4 and TGFR beta.

Inhibiting of inhibitory molecules may be achieved by any convenient method including but not limited to e.g., the administration of a direct inhibitor of the inhibitory molecule (e.g., an antibody that binds the inhibitory molecule, a small molecule antagonist of the inhibitory molecule, etc.), administration of an agent that inhibits expression of the inhibitory molecule (e.g., an inhibitory nucleic acid, e.g., a dsRNA, e.g., an siRNA or shRNA targeting a nucleic acid encoding the inhibitory molecule), an indirect inhibitor of the inhibitory signaling, and the like. In some instances, an agent that may be administered may be an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as Yervoy (Bristol-Myers Squibb)), Tremelimumab (Pfizer, formerly known as ticilimumab, CP-675, 206)), TIM3, LAG3, or the like.

In some embodiments, methods include administering to the subject an immune checkpoint inhibitor like anti-CTLA4 or anti-PD-1 and anti-PD-1L agents. The immune system depends on multiple checkpoints to avoid over-activation of the immune system on healthy cells, and tumor cells often take advantage of these checkpoints in order to escape detection by the immune system. CTLA-4, shown to be aberrantly upregulated and present on the surface of T cells in certain cancers, and PD-1, also upregulated in certain tumors and found to inhibit T-cell function, are checkpoints that have been studied as targets for cancer therapy (Pardoll, D. M. 2012 *Nat Rev Cancer* 12(4):252-264; Sharma, et al. 2011 *Nat Rev Cancer* 11(11):805-812).

In some instances, the methods of the instant disclosure may be used without any additional conventional therapy including e.g., where the method described herein is the sole method used to treat the subject. For example, in the case of oncology, the methods described herein may, in some instances, be the sole method used to treat the subject for a cancer.

Determining when combination therapies, e.g., involving the administration of one or more agents that ameliorates one or more side effects of a therapy described herein or involving the administration of one or more agents that enhances a therapy described herein, are indicated and the specifics of the administration of such combination therapies are within the skill of the relevant medical practitioner. In some instances, dosage regimens and treatment schedules of combination therapies may be determined through clinical trials.

In some instances, a subject may be evaluated, in certain contexts, through one or more of the following diagnostics procedures: 3D CT angiography, Angiography, Anoscopy, Autofluorescence bronchoscopy/fluorescence bronchoscopy, Barium swallow or enema, Biopsy, Bone Marrow Aspiration and Biopsy, Bone Scan, Bronchoscopy, CA-125 test, CAD for mammography, CTC Test, Chest x-ray, Colonoscopy, Complete Blood Count Test, Computed Tomography Scan, CT-guided biopsy, DEXA scan, Digital Breast Tomosynthesis, Electrocardiogram, Endobronchial ultrasound, Endoscopic ultrasound, ERCP, Flow cytometry, Full-field digital mammography, Genetic testing, Large bore CT scanner/RT with simulation, Lumbar puncture, Magnetic Resonance Imaging, Mammography, Miraluma breast imaging, MRI-Guided Breast Biopsy, Multi-detector CT scanner, Multiple-gated acquisition (MUGA) scan, Navigational Bronchoscopy, Nuclear Medicine Imaging, Oncotype DX Test, Pap test, Pelvic exam, PET Scan, PET-CT Scan, Radiofrequency ablation, Sentinel lymph node biopsy, Spiral CT, Tumor marker testing, Tumor molecular profiling, Ultrasound, Video Capsule Endoscopy, X-ray, and the like.

Diagnostic procedures may be performed for a variety of reasons including but not limited to e.g., to screen for cancer or precancerous conditions before a person has any symptoms of disease; to help diagnose cancer; to provide information about the stage of a cancer; to provide information about the malignancy of a tumor; to provide information about the size and/or extent of a primary tumor; to provide information about whether or not a tumor has metastasized; to plan treatment; to monitor a patient's general health during treatment; to check for potential side effects of the treatment; to determine whether a cancer is responding to treatment; to find out whether a cancer has recurred; etc.

Methods for Preparing Conjugate Compounds

As summarized above, aspects of the present disclosure include methods for preparing the subject conjugate compounds. In practicing methods according to certain embodiments, methods include contacting an anti-cancer agent with a linker precursor to produce an activated anti-cancer agent and contacting the activated anti-cancer agent with a protein, peptide or pepetidomimetic that binds selectively to a neurotrophin receptor. In embodiments, the linker precursor may be a zero-length crosslinker precursor, homobifunctional linker precursor, heterobifunctional linker precursor or a trifunctional crosslinker precursor. In certain embodiments, the anti-cancer agent is contacted with a bifunctional linker precursor to produce the activated anti-cancer agent, such as a homobifunctional or heterobifunctional linker precursor. In some embodiments, the bifunctional linker precursor includes a succimide, such as where the bifunctional linker precursor is N,N'-disuccinimidyl carbonate.

The linker precursor is contacted with the active agent and with a reactive moiety of anti-cancer agent. The reactive group may be a nucleophilic or electrophilic reactive group, depending on the reactive group of the linker precursor. In some instances, the anti-cancer agent includes a nucleophilic reactive group, such as a hydroxyl group. In certain instances, the anti-cancer agent includes a primary hydroxyl group. Methods according to certain embodiments include functionalizing the anti-cancer agent to include a reactive group, such as a nucleophilic reactive group (e.g., hydroxyl group) for reacting with the linker precursor component.

Coupling of the linker precursor with the anti-cancer agent produces an activated anti-cancer agent. The anti-cancer agent is contacted with the binding moiety that selectively binds to the nerve cell (e.g., neurotrophin receptor) to produce and endocytose the conjugate compounds.

In embodiments, contacting the binding moiety includes reacting a functional group on the binding moiety with a linker precursor of the activated anti-cancer agent. In some embodiments, the functional group on the binding moiety is an hydroxyl group, an amine group or a sulfhydryl group. For example, the functional group of the binding moiety may be a side chain of an amino acids, such as a lysine side chain, a cysteine side chain or serine side chain.

General Synthetic Procedures for Anti-Cancer Agent Conjugates

A representative synthesis for compounds as described herein is shown in the following schemes. The term "RG" refers to a reactive group (e.g., hydroxyl, amine, sulfhydryl) and "LG" refers to a leaving group (e.g., a succimide group). The term "X" refers to the linker moiety (e.g., carbonate, carbamate, etc.)

SCHEME 1

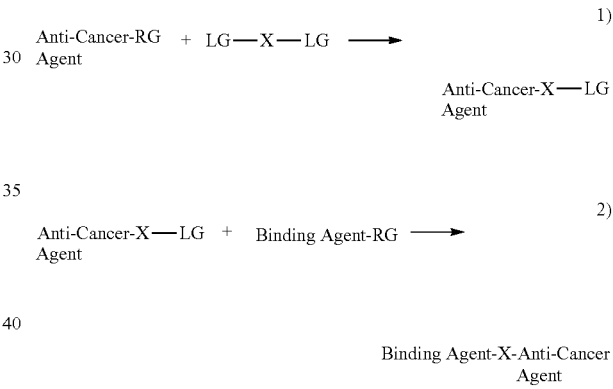

In Scheme 1, an anti-cancer agent having a nucleophilic reactive group, such as a hydroxyl group (e.g., a primary hydroxyl group) is contacted with a bifunctional linker precursor compound having an electrophilic reactive moiety and a leaving group (e.g., a succimide) to produce an activated anti-cancer agent compound. Contacting of the activated anti-cancer agent with a binding agent (e.g., a peptide) having a reactive group such as an hydroxyl, amine, or sulfhydryl group forms a conjugate a described herein.

Scheme 2 depicts an example synthesis of an mTOR inhibitor (everolimus) with brain-derived neutrophic factor (BDNF). Everolimus includes a primary hydroxyl functional group which is reactive with bifunctional linker precursor N,N'-disuccinimidyl carbonate (DSC) to produce activated everolimus. Contacting activated everolimus with brain-derived neutrophic factor provides for reaction between an amine side chain in BDNF and the reactive moiety of activated everolimus to produce a BDNF—everolimus conjugate. Two equivalents of N-hydroxysuccinimide are formed as by-products.

SCHEME 2
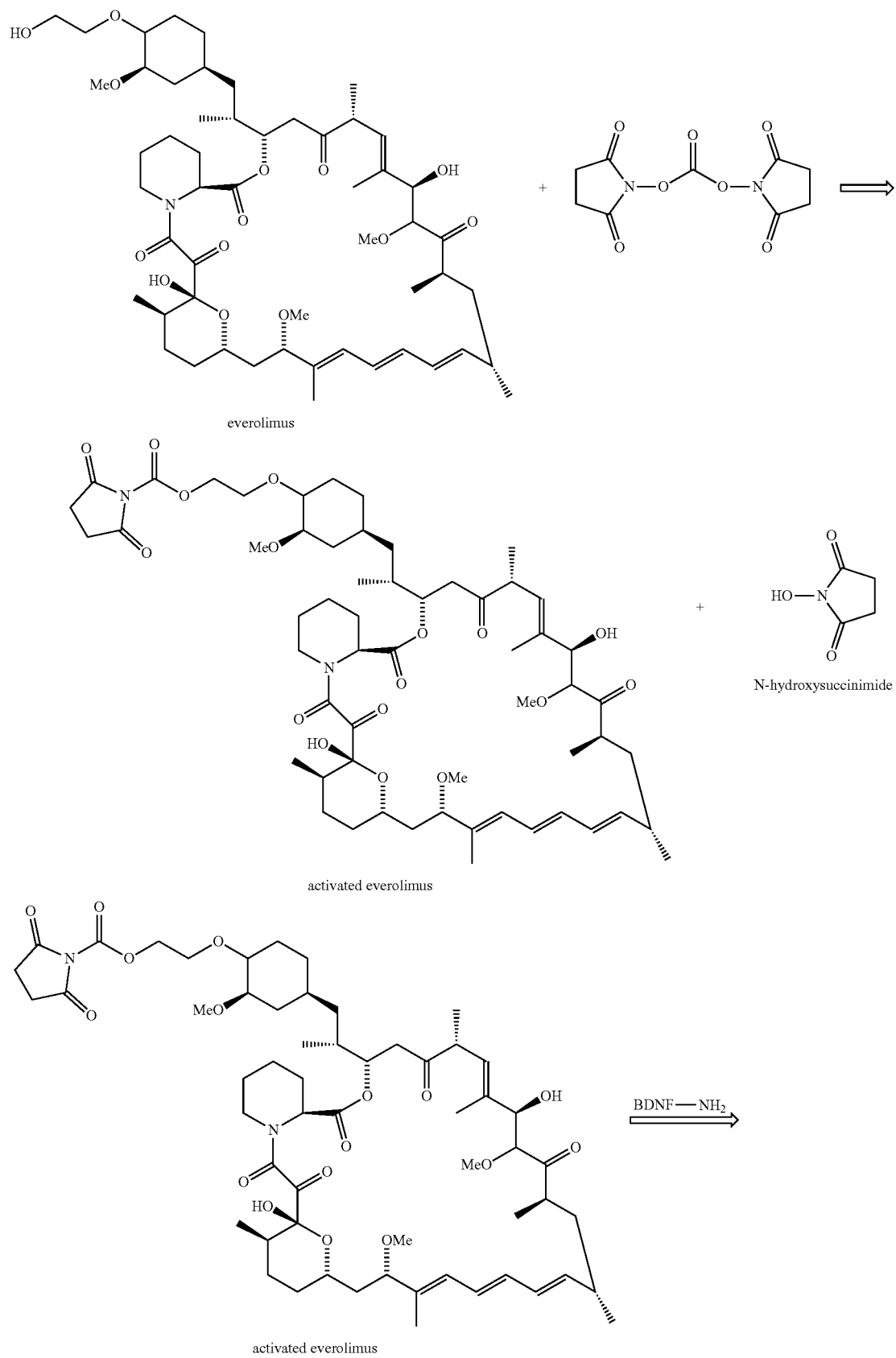

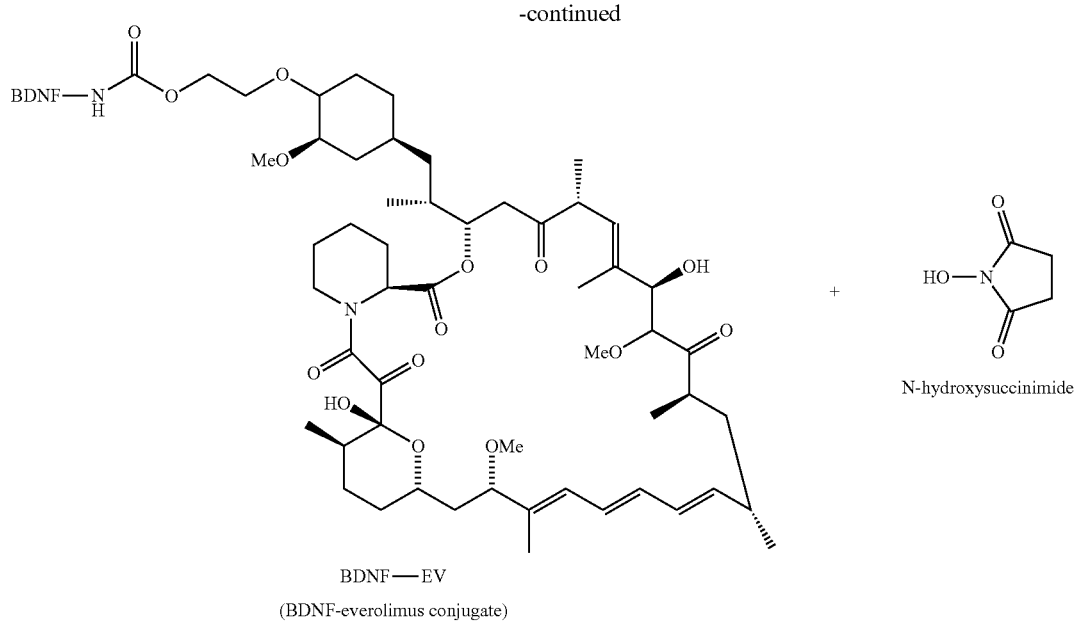

BDNF—EV
(BDNF-everolimus conjugate)

Scheme 3 depicts an example synthesis of an MEK kinase inhibitor inhibitor (selumetinib) with brain-derived neutrophic factor (BDNF). Selumetinib includes a primary hydroxyl functional group which is reactive with bifunctional linker precursor N,N'-disuccinimidyl carbonate (DSC) to produce activated selumetinib. Contacting activated everolimus with brain-derived neutrophic factor provides for reaction between an amine side chain in BDNF and the reactive moiety of activated selumetinib to produce a BDNF—selumetinib conjugate. Two equivalents of N-hydroxysuccinimide are formed as by-products.

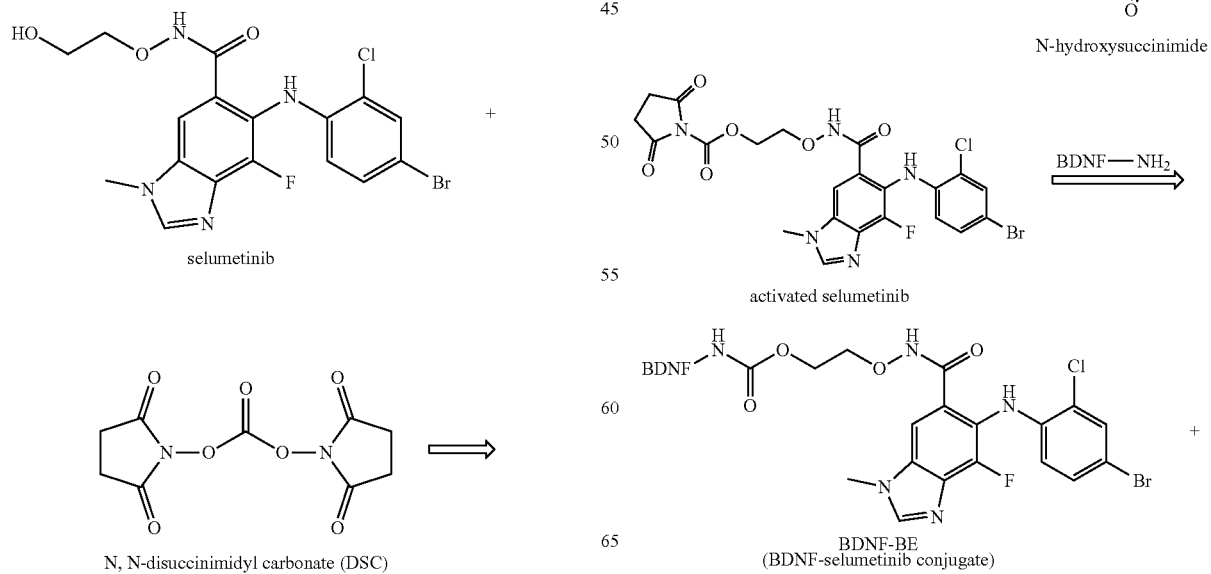

-continued

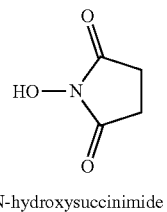

N-hydroxysuccinimide

Kits

Aspects of the present further include kits, where kits include one or more of the subject compounds or compositions having a conjugate compound as described above and a pharmaceutically acceptable carrier and one or more components for administering the compound/composition to a subject. In certain embodiments, kits include a syringe with or without a need, such as for administering the composition. In certain instances, kits include a needle and syringe for intracisternal or intrathecal injection of the compound/composition. In some instances, the kits can include one or more additional components (e.g., buffers, water, injection site cleaning components etc.). In some instances, the kits may further include a sample collection device, e.g., blood collection device such as an evacuated blood collection tube, needle, syringe, pipette, tourniquet, etc. as desired.

The various assay components of the kits may be present in separate containers, or some or all of them may be pre-combined. For example, in some instances, one or more components of the kit, are present in a sealed pouch, e.g., a sterile foil pouch or envelope.

In addition to the above components, the subject kits may further include (in certain embodiments) instructions for practicing the methods for administering the compositions as described herein. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

Aspects, including embodiments, of the subject matter described herein may be beneficial alone or in combination, with one or more other aspects or embodiments. Without limiting the description, certain non-limiting aspects of the disclosure are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Compounds

1. A compound of formula I:

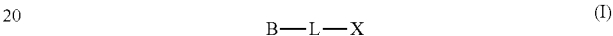

wherein:
B is a protein, peptide or pepetidomimetic that binds selectively to a neurotrophin receptor;
L is a linker; and
X is an anti-cancer agent.

2. The compound according to 1, wherein the anti-cancer agent is configured to be internalized into a cancer cell.

3. The compound according to 2, wherein the cancer is glioma.

4. The compound according to 3, wherein the cancer is optic pathway glioma.

5. The compound according to any one of 1-4, wherein the anti-cancer agent is a mammalian target of rapamycin (mTOR) inhibitor or mitogen-activated protein kinase (MEK) inhibitor.

6. The compound according to 5, wherein the mTOR inhibitor is a compound selected from the group consisting of sirolimus, temsiorolimus, everolimus, and ridaforolimus.

7. The compound according to 6, wherein the anti-cancer agent is everolimus.

8. The compound according to 6, wherein the compound is of Formula IA1:

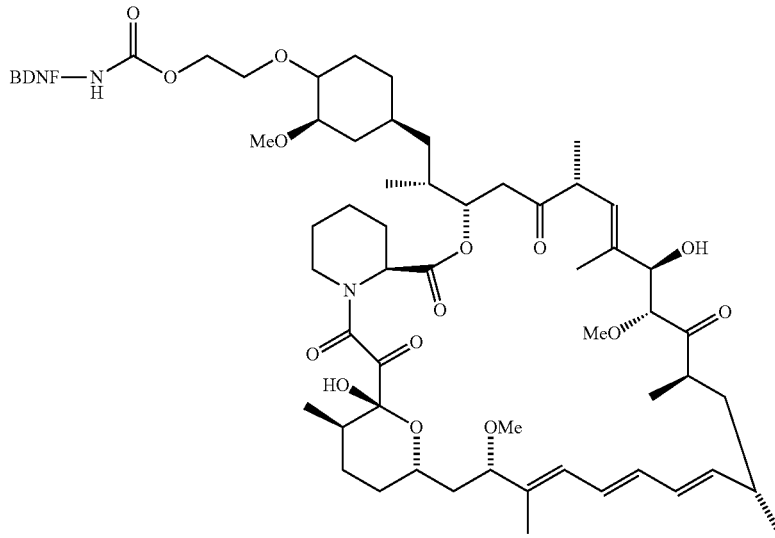

9. The compound according to 6, wherein the compound is of Formula IA2:

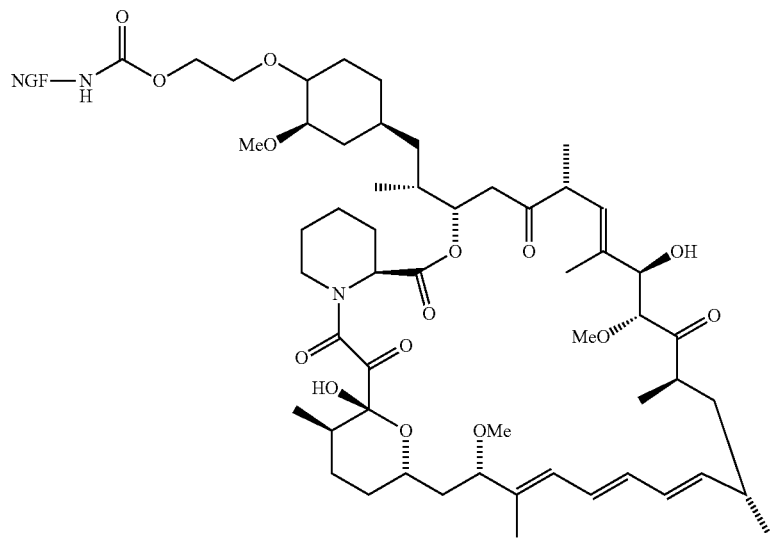

10. The compound according to 5, wherein the MEK inhibitor is a compound selected from the group consisting of trametinib, dabrafenib, cobimetinib, vemurafenib, binimetinib, and selumetinib.

11. The compound according to 10, wherein the anti-cancer agent is selumetinib.

12. The compound according to 11, wherein the compound is of Formula IB1:

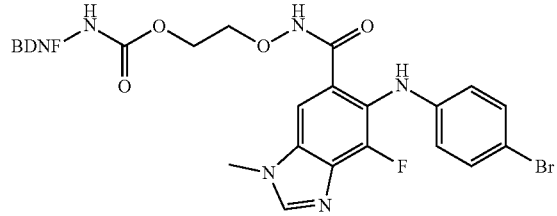

13. The compound according to 11, wherein the compound is of Formula IB2:

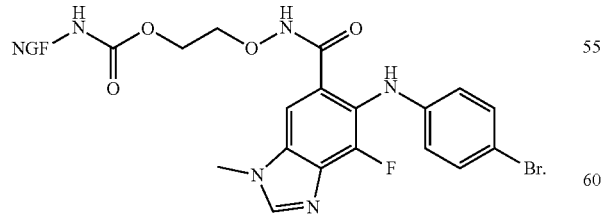

14. The compound according to 1, wherein the cancer comprises perineural invasion.

15. The compound according to 14, wherein the anti-cancer agent is a heat shock protein 90 (hsp90) inhibitor.

16. The compound according to 15, wherein the hsp90 inhibitor is a compound selected from the group consisting of:

a) alvespinomycin:

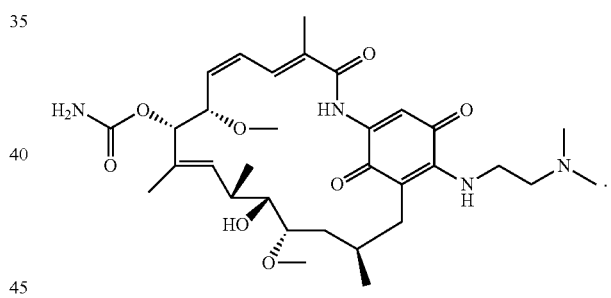

b) 17-N-Allylamino-17-demethoxygeldanamycin (17AAG):

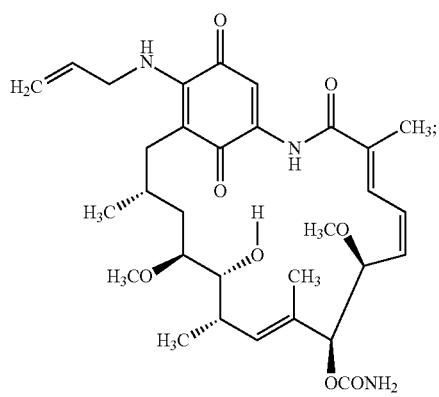

c) luminespib (AUY-922, NVP-AUY922):
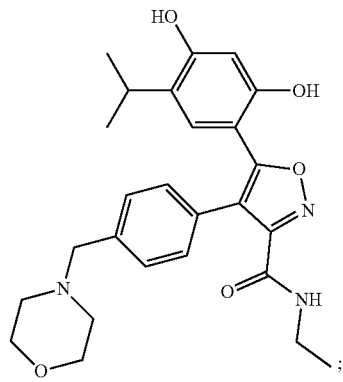 [SMILES: CCNC(=O)c1noc(-c2cc(C(C)C)c(O)cc2O)c1-c1ccc(CN2CCOCC2)cc1]
d) ganetespib (STA-9090):
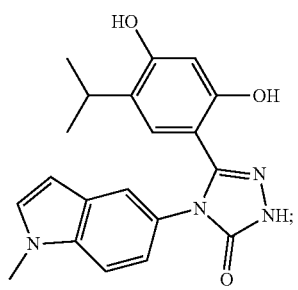 [SMILES: CC(C)c1cc(-c2n[nH]c(=O)n2-c2ccc3c(ccn3C)c2)c(O)cc1O]
e) onalespib (AT13387):
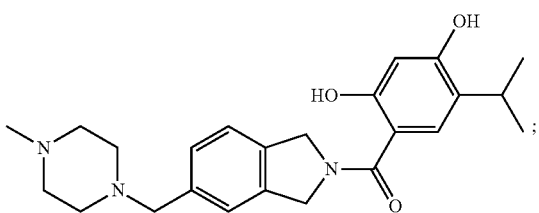 [SMILES: CC(C)c1cc(C(=O)N2Cc3ccc(CN4CCN(C)CC4)cc3C2)c(O)cc1O]
f) NCP-BEP800:
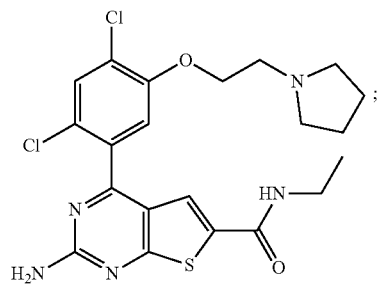 [SMILES: CCNC(=O)c1cc2c(-c3cc(OCCN4CCCC4)c(Cl)cc3Cl)nc(N)nc2s1]
g) BIIB021:
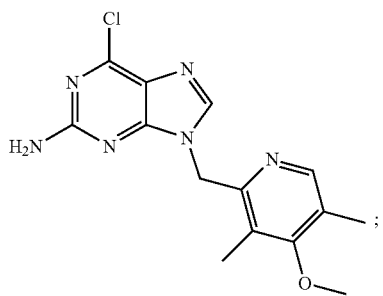 [SMILES: COc1c(C)cnc(Cn2cnc3c(Cl)nc(N)nc32)c1C]
h) PF-04929113 (SNX-5422):
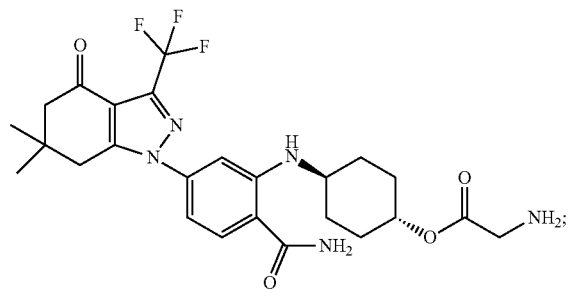 [SMILES: CC1(C)CC(=O)c2c(C(F)(F)F)nn(-c3ccc(C(N)=O)c(N[C@H]4CC[C@H](OC(=O)CN)CC4)c3)c2C1]
i) SNX-2112 (PF-04928473):
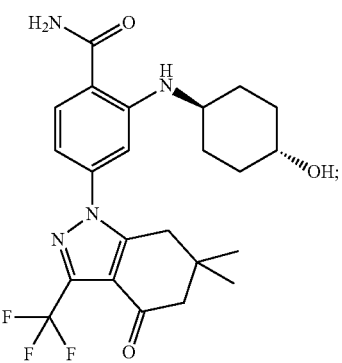 [SMILES: CC1(C)CC(=O)c2c(C(F)(F)F)nn(-c3ccc(C(N)=O)c(N[C@H]4CC[C@H](O)CC4)c3)c2C1]
j) KW-2478:
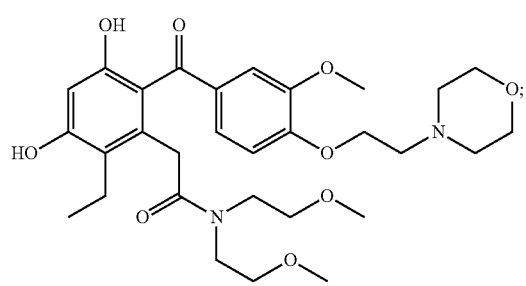 [SMILES: CCc1c(O)cc(O)c(C(=O)c2ccc(OCCN3CCOCC3)c(OC)c2)c1CC(=O)N(CCOC)CCOC]

k) XL888:
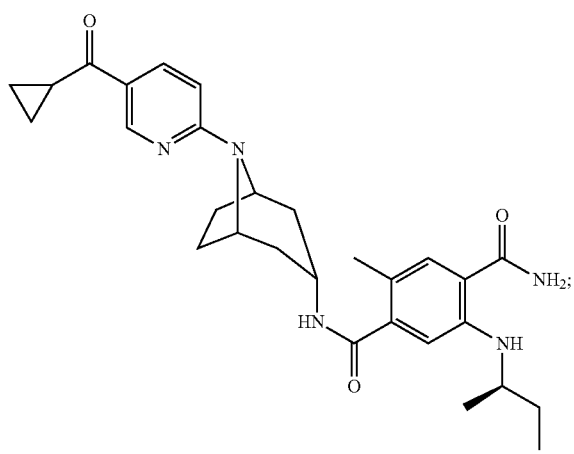 [SMILES: CC[C@@H](C)Nc1cc(C(=O)NC2CC3CCC(C2)N3c2ccc(C(=O)C3CC3)cn2)c(C)cc1C(N)=O]
l) NMS-E973:
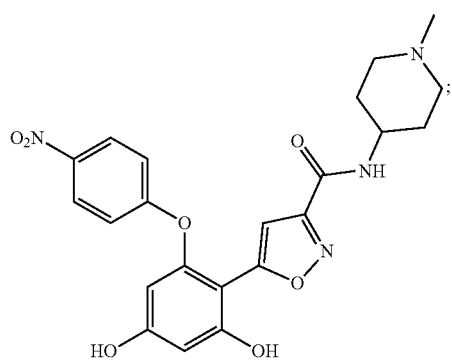 [SMILES: CN1CCC(NC(=O)c2cc(-c3c(O)cc(O)cc3Oc3ccc([N+](=O)[O-])cc3)on2)CC1]
m) PU-H7:
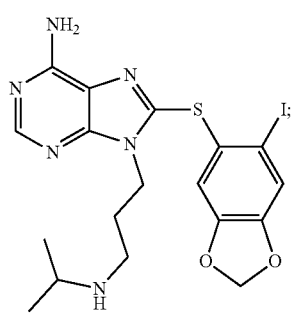 [SMILES: CC(C)NCCCn1c(Sc2cc3c(cc2I)OCO3)nc2c(N)ncnc21]
n) VER-49009:
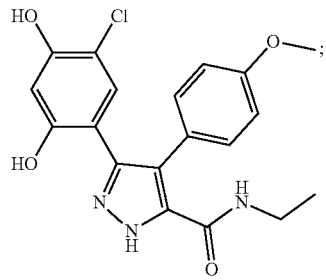 [SMILES: CCNC(=O)c1[nH]nc(-c2cc(Cl)c(O)cc2O)c1-c1ccc(OC)cc1]
o) CH5138303:
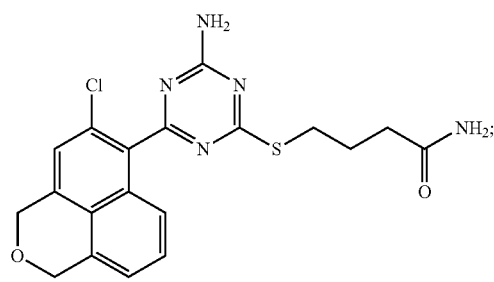 [SMILES: NC(=O)CCCSc1nc(N)nc(-c2c(Cl)cc3c4c(cccc24)COC3)n1]
p) VER-50589:
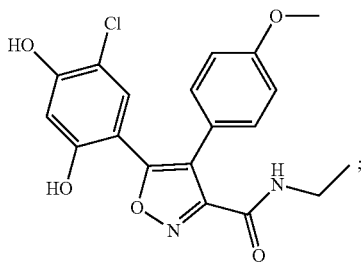 [SMILES: CCNC(=O)c1noc(-c2cc(Cl)c(O)cc2O)c1-c1ccc(OC)cc1]
q) VER155008:
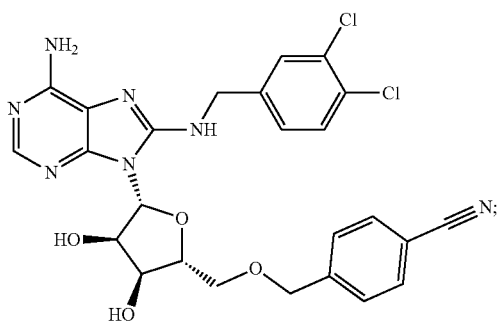 [SMILES: N#Cc1ccc(COC[C@H]2O[C@@H](n3c(NCc4ccc(Cl)c(Cl)c4)nc4c(N)ncnc43)[C@H](O)[C@@H]2O)cc1]

and
r) geldanamycin:

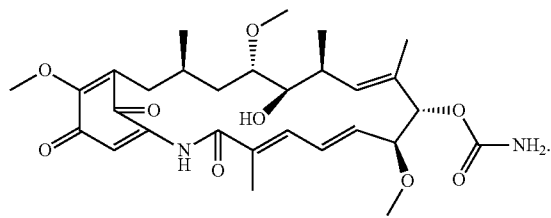 [SMILES: COC1=C2C[C@@H](C)C[C@H](OC)[C@H](O)[C@@H](C)/C=C(\C)[C@H](OC(N)=O)[C@@H](OC)/C=C/C=C(\C)C(=O)NC(=CC1=O)C2=O]

17. The compound according to 16, wherein the hsp90 inhibitor is alvespinomycin:

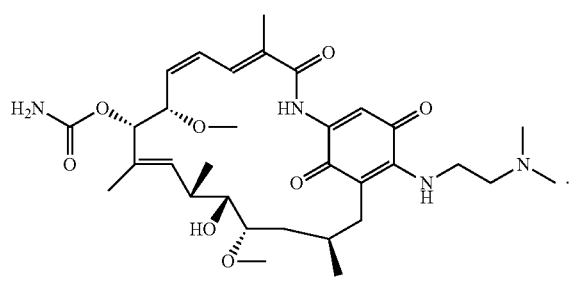 [SMILES: CO[C@H]1/C=C\C=C(/C)C(=O)NC2=CC(=O)C(NCCN(C)C)=C(C[C@@H](C)C[C@H](OC)[C@H](O)[C@@H](C)/C=C(\C)[C@@H]1OC(N)=O)C2=O]

18. The compound according to 17, wherein the compound is of Formula HSP-IA1:

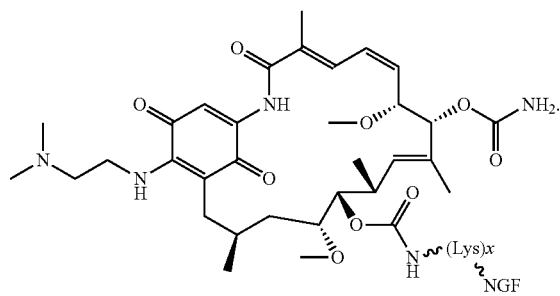

19. The compound according to 17, wherein the compound is of Formula HSP-IA2:

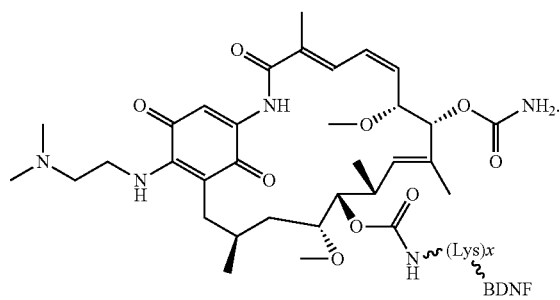

20. The compound according to 8, wherein the anti-cancer agent is a checkpoint inhibitor.
21. The compound according to claim 20, wherein the checkpoint inhibitor is an inhibitory compound that targets one or more of PD-1, PD-L1, CTLA4, TIM3, LAG3, VISTA, BTLA, TIGIT, LAIR1, CD160, 2B4 and TGFRβ.
22. The compound according to 21, wherein the checkpoint inhibitor is an inhibitory compound that targets PD-1.
23. The compound according to 22, wherein the checkpoint inhibitor is a compound selected from the group consisting of:
a) S7911:

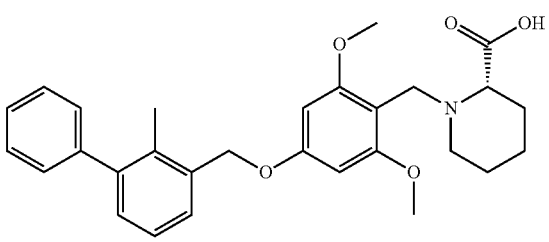 [SMILES: COc1cc(OCc2cccc(-c3ccccc3)c2C)cc(OC)c1CN1CCCC[C@H]1C(=O)O]

b) BMS202:

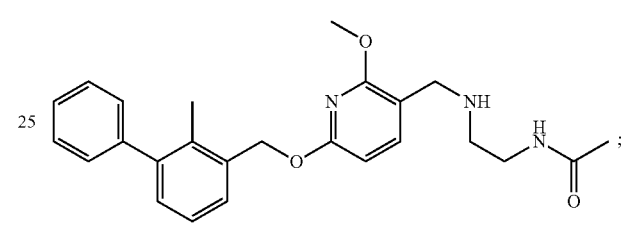

and
c) S8158:

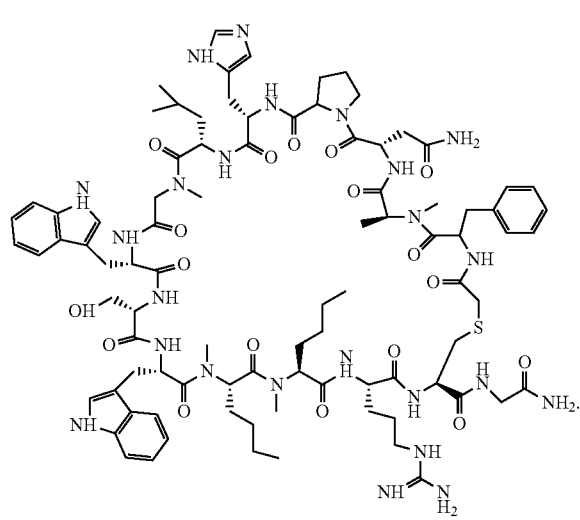 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)NC(Cc2ccccc2)C(=O)N(C)[C@@H](C)C(=O)N[C@@H](CC(N)=O)C(=O)N2CCCC2C(=O)N[C@@H](Cc2cnc[nH]2)C(=O)N[C@@H](CC(C)C)C(=O)N(C)CC(=O)N[C@@H](Cc2c[nH]c3ccccc23)C(=O)N[C@@H](CO)C(=O)N[C@@H](Cc2c[nH]c3ccccc23)C(=O)N1C]

24. The compound according to 23, wherein the checkpoint inhibitor is S7911:

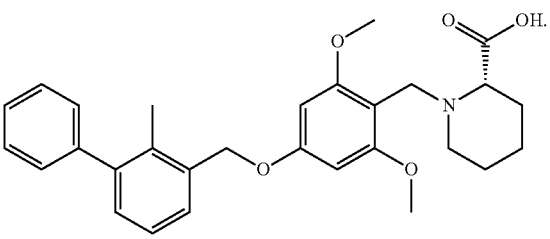 [SMILES: COc1cc(OCc2cccc(-c3ccccc3)c2C)cc(OC)c1CN1CCCC[C@H]1C(=O)O]

25. The compound according to 24, wherein the compound is of Formula CP-IA1

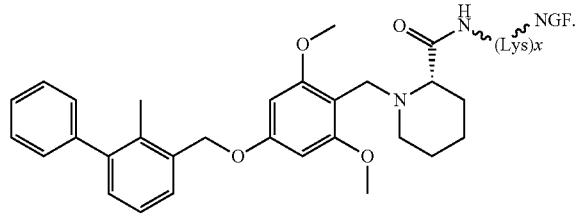

26. The compound according to claim 24, wherein the compound is of Formula CP-IA2

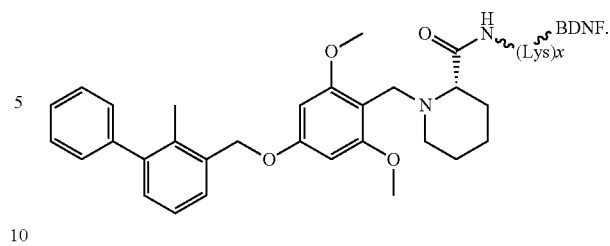

27. The compound according to 8, wherein the anti-cancer agent is a chemokine 4/chemokine ligand 12 (CX4/CXCL12) inhibitor.

28. The compound according to 27, wherein the CX4/CXCL12 inhibitor is a compound selected from the group consisting of:

a) burixafor:

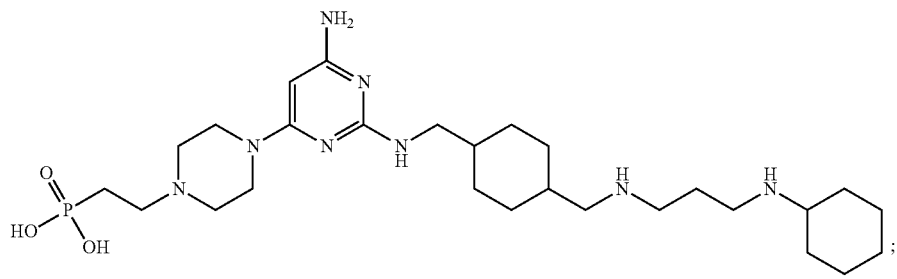 [SMILES: Nc1cc(N2CCN(CCP(=O)(O)O)CC2)nc(NCC2CCC(CNCCCNC3CCCCC3)CC2)n1]

b) LY2510924:

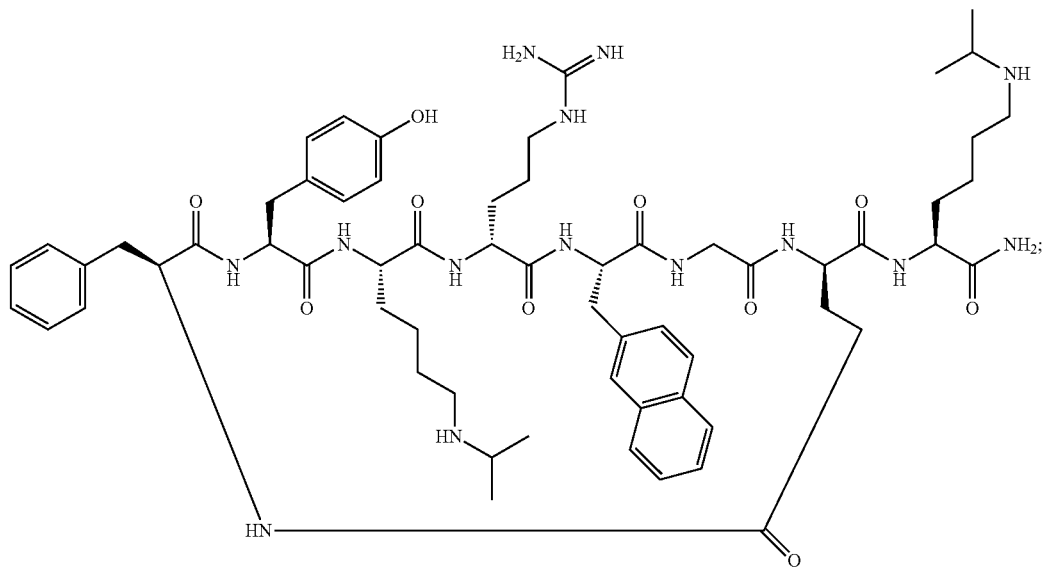 [SMILES: CC(C)NCCCC[C@H](NC(=O)[C@H]1CCC(=O)N[C@@H](Cc2ccccc2)C(=O)N[C@@H](Cc2ccc(O)cc2)C(=O)N[C@@H](CCCCNC(C)C)C(=O)N[C@H](CCCNC(=N)N)C(=O)N[C@@H](Cc2ccc3ccccc3c2)C(=O)NCC(=O)N1)C(N)=O]

c) AMD3100:
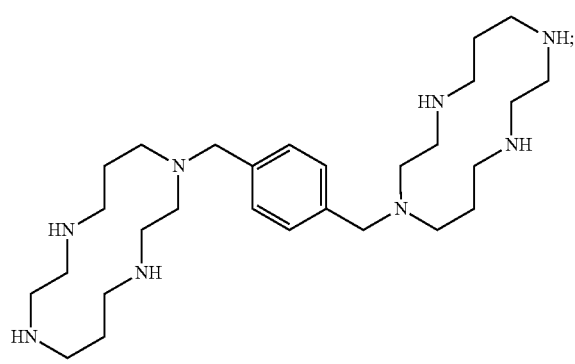 [SMILES: c1cc(CN2CCCNCCNCCCNCC2)ccc1CN1CCCNCCNCCCNCC1]
and
d) AMD3465:
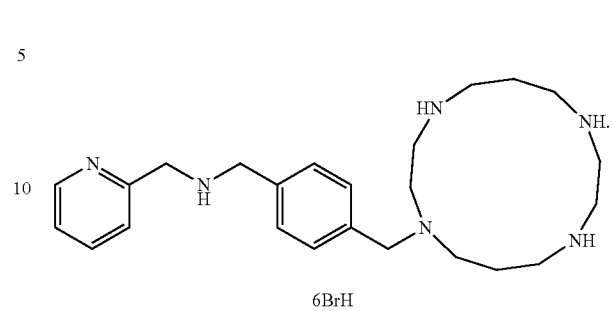
29. The compound according to 28, wherein the CX4/CXCL12 inhibitor is LY2510924:
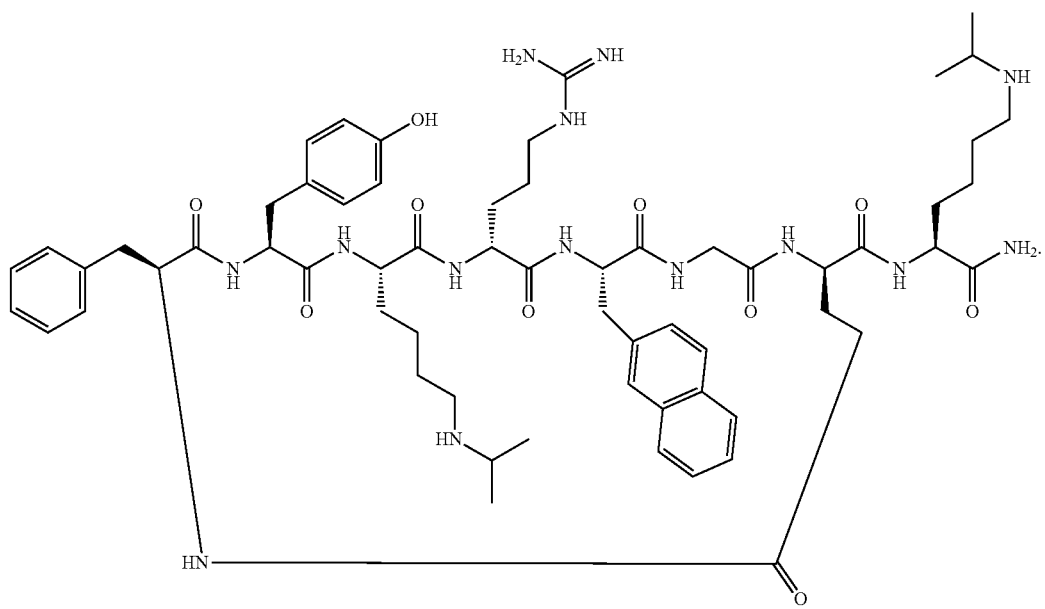 [SMILES: CC(C)NCCCC[C@H](NC(=O)[C@H]1CCC(=O)N[C@@H](Cc2ccccc2)C(=O)N[C@@H](Cc2ccc(O)cc2)C(=O)N[C@@H](CCCCNC(C)C)C(=O)N[C@H](CCCNC(=N)N)C(=O)N[C@@H](Cc2ccc3ccccc3c2)C(=O)NCC(=O)N1)C(N)=O]
30. The compound according to 28, wherein the CX4/CXCL12 inhibitor is burixafor:
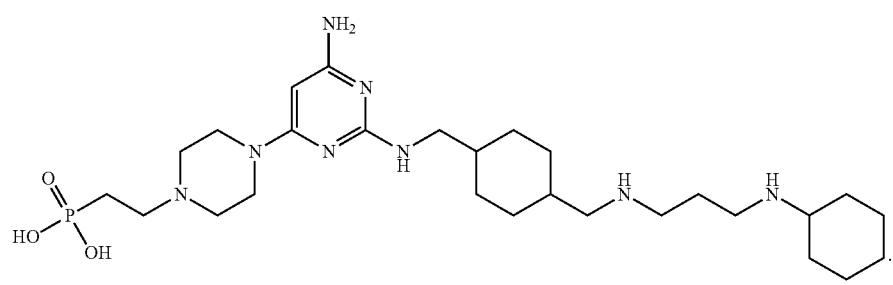

31. The compound according to 30, wherein the compound is of Formula CX-IA1:

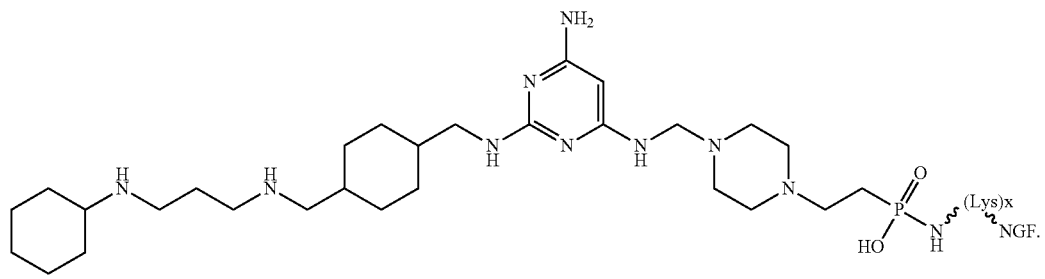

32. The compound according to 30, wherein the compound is of Formula CX-IA2:

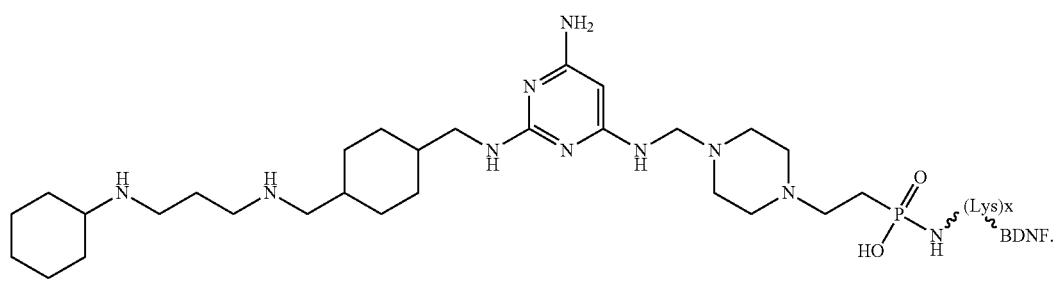

24. The compound according to 8, wherein the compound is an imidazoquinolone amine.
25. The compound according to 24, wherein the compound is imiquimod:

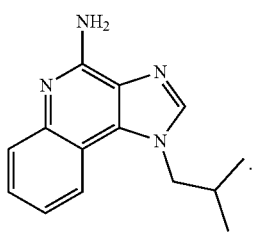

26. The compound according to 1, wherein the cancer is skin cancer.
27. The compound according to 26, wherein the anti-cancer agent is an imidazoquinolone amine.
25. The compound according to 27, wherein the compound is imiquimod:

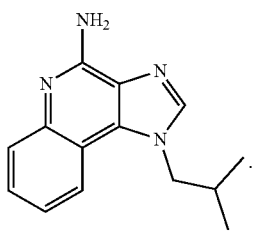

26. The compound according to any one of 1-25, wherein the linker is a cleavable linker.

27. The compound according to 26, wherein the linker is an acid-cleavable linker, a base-cleavable linker, a photo-cleavable linker or an enzyme-cleavable linker.
28. The compound according to any one of 1-27, wherein the linker is non-cleavable.
29. The compound according to any one of 1-28, wherein the linker comprises a carbamate.
30. The compound according to any one of 1-29, wherein B is a brain-derived neurotrophic factor (BDNF) or fragment thereof.
31. The compound according to any one of 1-29, wherein B is a nerve growth factor (NGF) or fragment thereof.
32. The compound according to any one of 30-32, wherein B is a BDNF or fragment thereof that binds to tropomyosin receptor kinase B (trkB) or an NGF or fragment thereof that binds to tropomyosin receptor kinase A (trkA).
33. The compound according to any one of 30-32, wherein binding of BDNF or fragment thereof to trkB or binding of NGF or fragment thereof to trkA triggers internalization of the compound into a cancer cell.
34. The compound according to any one of 32-34, wherein the cancer is glioma.
35. The compound according to 34, wherein the cancer is optic pathway glioma.
36. The compound according to any one of 32-33, wherein the cancer comprises perineural invasion.
37. The compound according to any one of 32-33, wherein the cancer is skin cancer.
38. The compound according to 1, wherein B is a BDNF or fragment thereof or NGF or fragment thereof that binds to p75 neurotrophin receptor.
39. The compound according to 38, wherein binding of the BDNF or fragment thereof or the NGF or fragment thereof to p75 triggers internalization of the compound into a cancer cell.
40. The compound according to any one of 38-39, wherein the cancer is glioma.

41. The compound according to 40, wherein the cancer is optic pathway glioma.
42. The compound according to any one of 38-40, wherein the cancer comprises perineural invasion.
43. The compound according to any one of 38-40, wherein the cancer is skin cancer.
44. The compound according to any one of 1-31, wherein B is a ciliary neurotrophic factor (CNTF) or fragment thereof.
45. The compound according to any one of 1-31, wherein B is a neurotrophic factor 3 (NT-3) or fragment thereof.
46. The compound according to any one of 1-31, wherein B is a glial-cell derived neurotrophic factor (GDNF).

Compositions

1. A composition comprising:
    a pharmaceutically acceptable carrier; and
    a compound of formula I:

$$B—L—X \quad (I)$$

wherein:
    B is a protein, peptide or pepetidomimetic that binds selectively to a neurotrophin receptor;
    L is a linker; and
    X is an anti-cancer agent.
2. The composition according to 1, wherein the composition is formulated as an injection.
3. The composition according to 1, wherein the composition is formulated for intracisternal administration.
4. The composition according to 1, wherein the composition is formulated for intrathecal administration.
5. The composition according to 1, wherein the anti-cancer agent is configured to be internalized into a cancer cell.
6. The composition according to 5, wherein the cancer is glioma.
7. The composition according to 6, wherein the cancer is optic pathway glioma.
8. The composition according to any one of 1-7, wherein the anti-cancer agent is a mammalian target of rapamycin (mTOR) inhibitor or mitogen-activated protein kinase (MEK) inhibitor.
9. The composition according to 8, wherein the mTOR inhibitor is a compound selected from the group consisting of sirolimus, temsiorolimus, everolimus and ridaforolimus.
10. The composition according to 9, wherein the anti-cancer agent is everolimus.
11. The composition according to 9, wherein the compound is of Formula IA1:

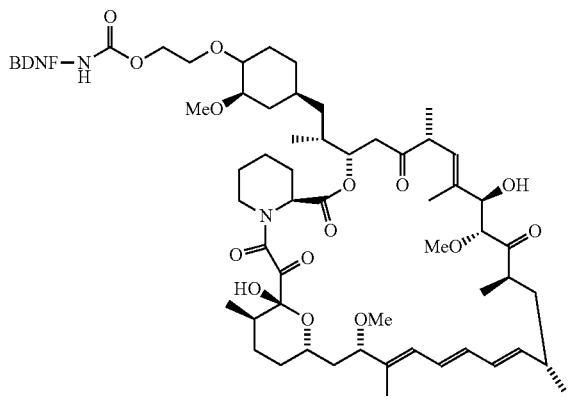

12. The composition according to 9, wherein the compound is of Formula IA2:

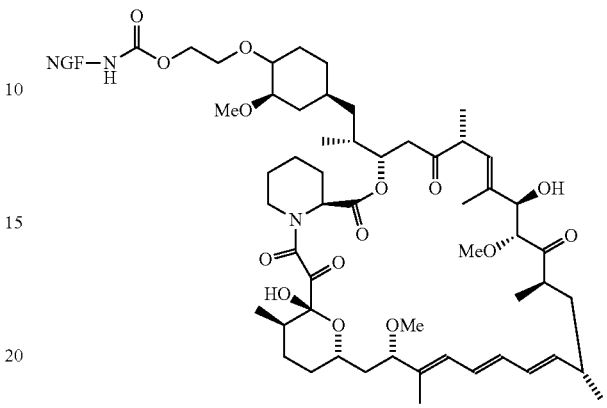

13. The composition according to 8, wherein the MEK inhibitor is a compound selected from the group consisting of trametinib, dabrafenib, cobimetinib, vemurafenib, binimetinib, and selumetinib.
14. The composition according to 13, wherein the anti-cancer agent is selumetinib.
15. The composition according to 13, wherein the compound is of Formula IB1:

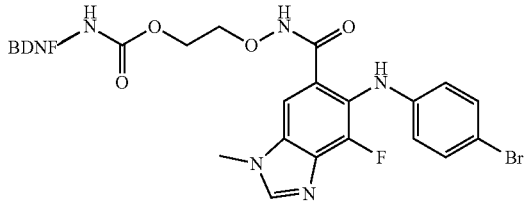

16. The composition according to 13, wherein the compound is of Formula IB2:

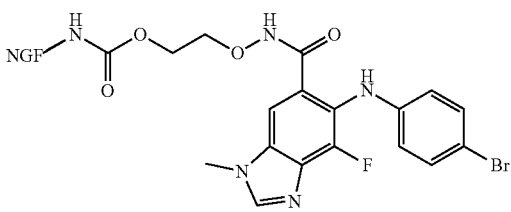

17. The composition according to 1, wherein the cancer comprises perineural invasion.
18. The composition according to 17, wherein the anti-cancer agent is a heat shock protein 90 (hsp90) inhibitor.
19. The composition according to 18, wherein the hsp90 inhibitor is a compound selected from the group consisting of:

a) alvespinomycin:
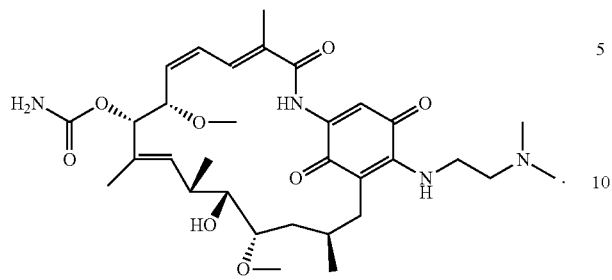
b) 17-N-Allylamino-17-demethoxygeldanamycin (17AAG):
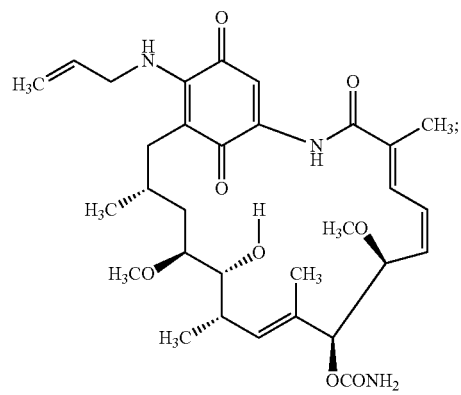
c) luminespib (AUY-922, NVP-AUY922):
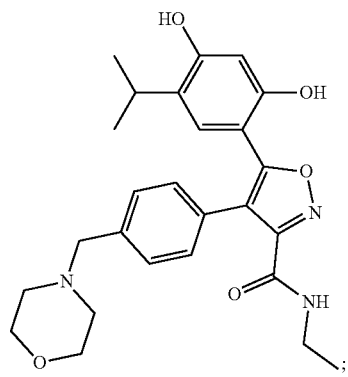 [SMILES: CCNC(=O)c1noc(-c2cc(C(C)C)c(O)cc2O)c1-c1ccc(CN2CCOCC2)cc1]
d) ganetespib (STA-9090):
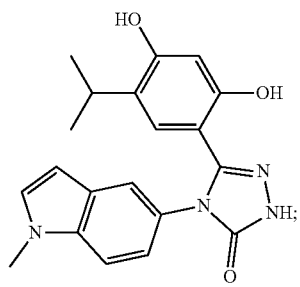 [SMILES: CC(C)c1cc(-c2n[nH]c(=O)n2-c2ccc3c(ccn3C)c2)c(O)cc1O]
e) onalespib (AT13387):
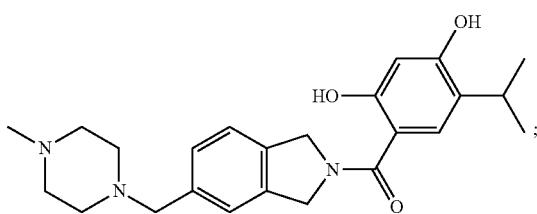 [SMILES: CC(C)c1cc(C(=O)N2Cc3ccc(CN4CCN(C)CC4)cc3C2)c(O)cc1O]
f) NVP-BEP800:
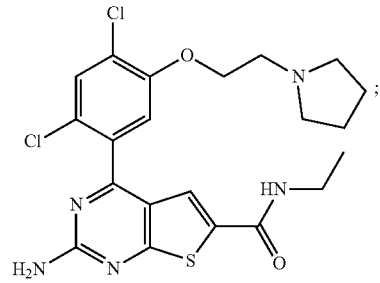 [SMILES: CCNC(=O)c1cc2c(-c3cc(OCCN4CCCC4)c(Cl)cc3Cl)nc(N)nc2s1]
g) BIIB021:
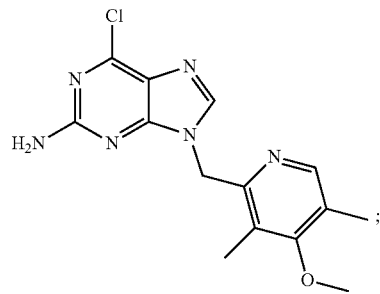 [SMILES: COc1c(C)cnc(Cn2cnc3c(Cl)nc(N)nc32)c1C]
h) PF-04929113 (SNX-5422):
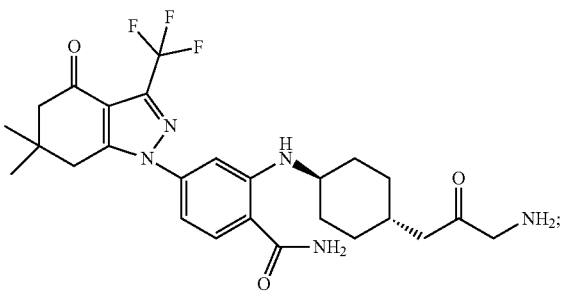 [SMILES: CC1(C)CC(=O)c2c(C(F)(F)F)nn(-c3ccc(C(N)=O)c(N[C@H]4CC[C@H](CC(=O)CN)CC4)c3)c2C1]

i) SNX-2112 (PF-04928473):
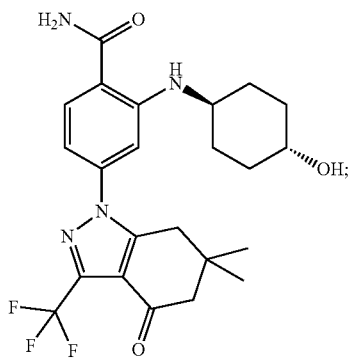 [SMILES: CC1(C)CC(=O)c2c(C(F)(F)F)nn(-c3ccc(C(N)=O)c(N[C@H]4CC[C@H](O)CC4)c3)c2C1]
j) KW-2478:
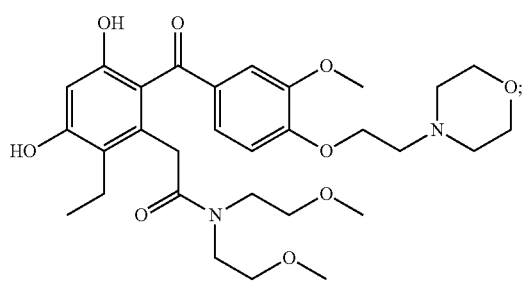 [SMILES: CCc1c(O)cc(O)c(C(=O)c2ccc(OCCN3CCOCC3)c(OC)c2)c1CC(=O)N(CCOC)CCOC]
k) XL888:
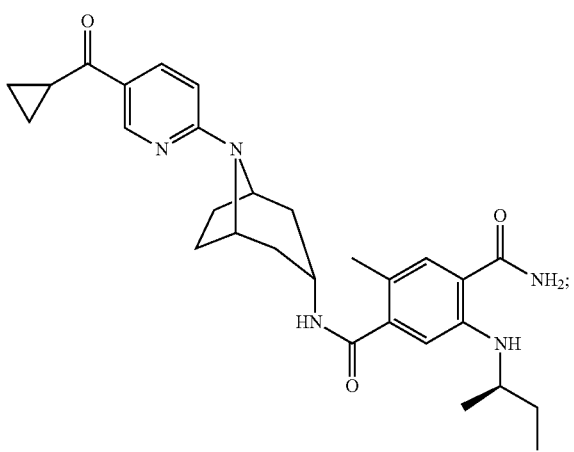 [SMILES: CC[C@@H](C)Nc1cc(C(=O)NC2CC3CCC(C2)N3c2ccc(C(=O)C3CC3)cn2)c(C)cc1C(N)=O]
l) NMS-E973:
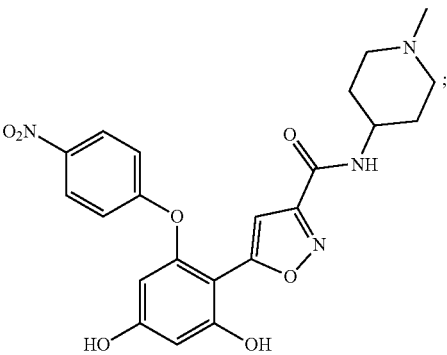 [SMILES: CN1CCC(NC(=O)c2cc(-c3c(O)cc(O)cc3Oc3ccc([N+](=O)[O-])cc3)on2)CC1]
m) PU-H71:
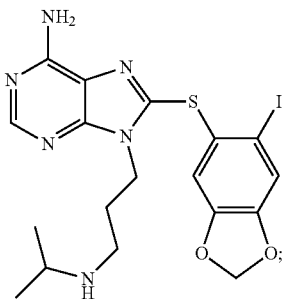 [SMILES: CC(C)NCCCn1c(Sc2cc3c(cc2I)OCO3)nc2c(N)ncnc21]
n) VER-49009:
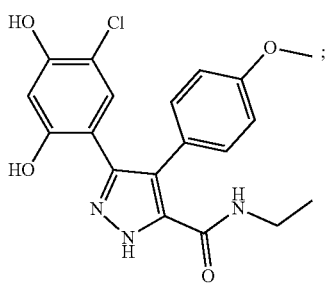 [SMILES: CCNC(=O)c1[nH]nc(-c2cc(Cl)c(O)cc2O)c1-c1ccc(OC)cc1]
o) CH5138303:
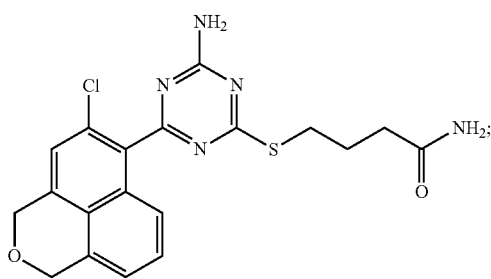 [SMILES: NC(=O)CCCSc1nc(N)nc(-c2c(Cl)cc3c4c(cccc24)COC3)n1]

p) VER-50589:

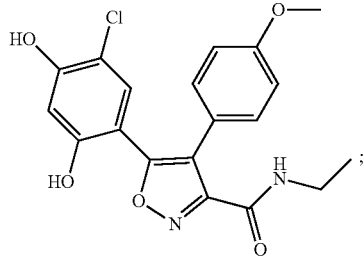 [SMILES: CCNC(=O)c1noc(-c2cc(Cl)c(O)cc2O)c1-c1ccc(OC)cc1]

q) VER155008:

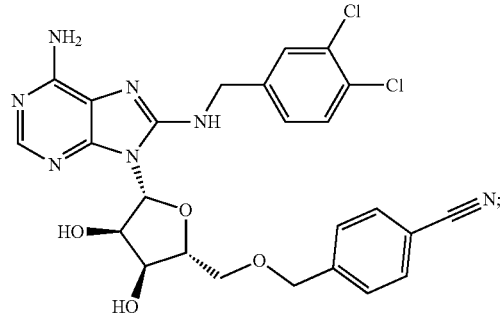 [SMILES: N#Cc1ccc(COC[C@H]2O[C@@H](n3c(NCc4ccc(Cl)c(Cl)c4)nc4c(N)ncnc43)[C@H](O)[C@@H]2O)cc1]

and r) geldanamycin:

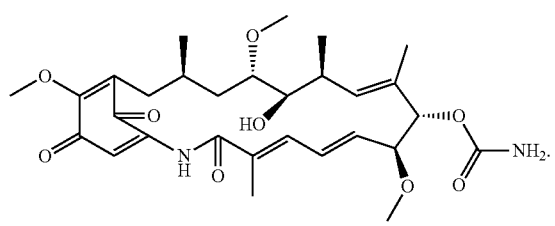 [SMILES: COC1=C2C[C@@H](C)C[C@H](OC)[C@H](O)[C@@H](C)/C=C(\C)[C@H](OC(N)=O)[C@@H](OC)/C=C/C=C(\C)C(=O)NC(=CC1=O)C2=O]

20. The composition according to 19, wherein the hsp90 inhibitor is alvespinomycin:

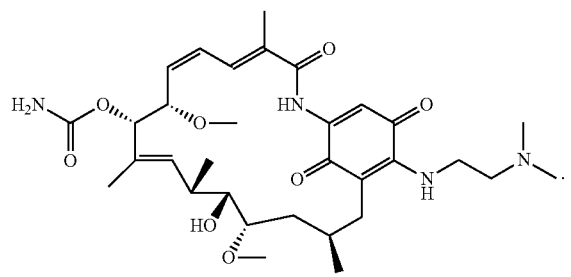

21. The composition according to 20, wherein the compound is of Formula HSP-IA1:

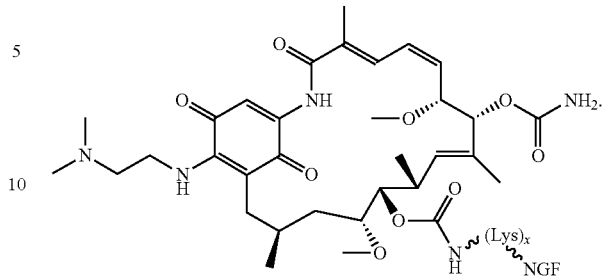

22. The composition according to 20, wherein the compound is of Formula HSP-IA2:

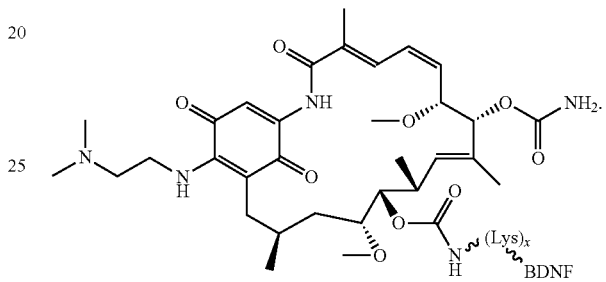

23. The composition according to 17, wherein the anti-cancer agent is a checkpoint inhibitor.

24. The composition according to 23, wherein the checkpoint inhibitor is an inhibitory compound that targets one or more of PD-1, PD-L1, CTLA4, TIM3, LAG3, VISTA, BTLA, TIGIT, LAIR1, CD160, 2B4 and TGFRβ.

25. The composition according to 24, wherein the checkpoint inhibitor is an inhibitory compound that targets PD-1.

26. The composition according to 25, wherein the checkpoint inhibitor is a compound selected from the group consisting of:

a) S7911:

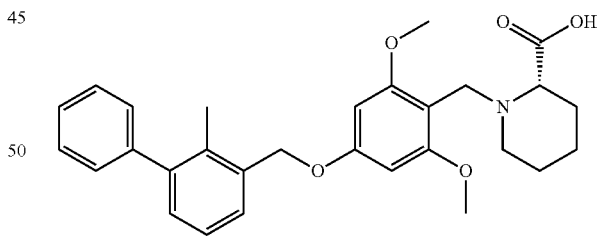

b) BMS202:

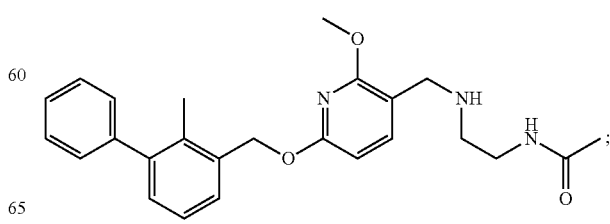

and c) S8158:

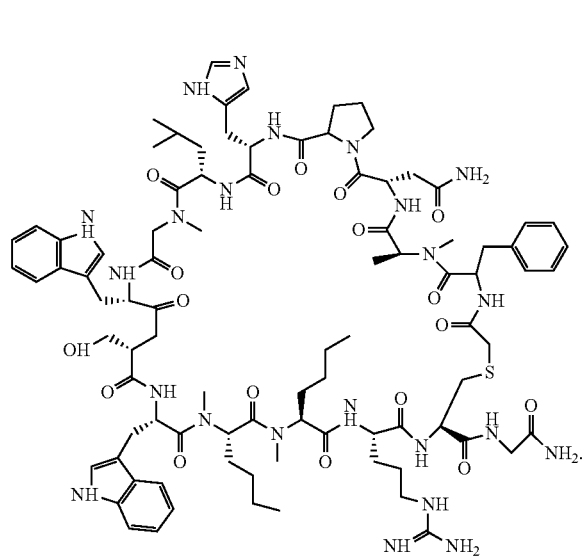 [SMILES: CCCC[C@H]1C(=O)N(C)[C@@H](CCCC)C(=O)N[C@@H](CCCNC(=N)N)C(=O)N[C@H](C(=O)NCC(N)=O)CSCC(=O)NC(Cc2ccccc2)C(=O)N(C)[C@@H](C)C(=O)N[C@@H](CC(N)=O)C(=O)N2CCCC2C(=O)N[C@@H](Cc2cnc[nH]2)C(=O)N[C@@H](CC(C)C)C(=O)N(C)CC(=O)N[C@@H](Cc2c[nH]c3ccccc23)C(=O)C[C@@H](CO)C(=O)N[C@@H](Cc2c[nH]c3ccccc23)C(=O)N1C]

27. The composition according to 26, wherein the checkpoint inhibitor is S7911:

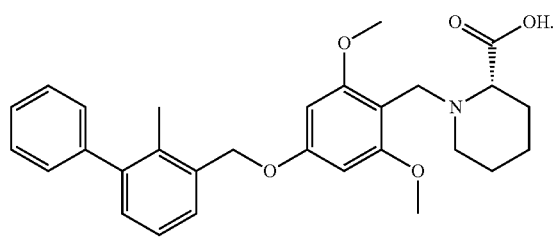 [SMILES: COc1cc(OCc2cccc(-c3ccccc3)c2C)cc(OC)c1CN1CCCC[C@H]1C(=O)O]

28. The composition according to 27, wherein the compound is of Formula CP-IA1:

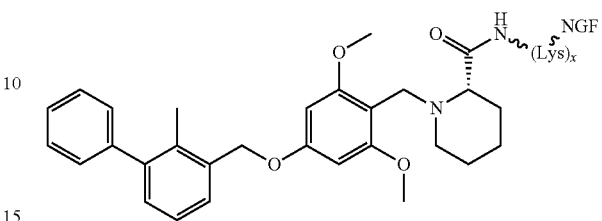

29. The composition according to 27, wherein the compound is of Formula CP-IA2:

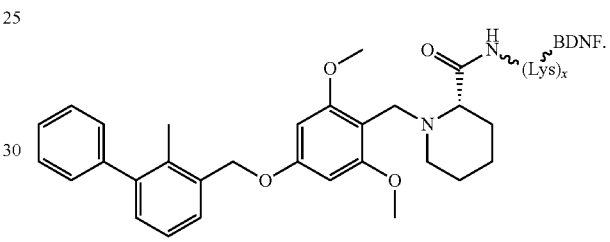

30. The composition according to 17, wherein the anti-cancer agent is a chemokine 4/chemokine ligand 12 (CX4/CXCL12) inhibitor.

31. The composition according to 30, wherein the CX4/CXCL12 inhibitor is a compound selected from the group consisting of:

a) burixafor:

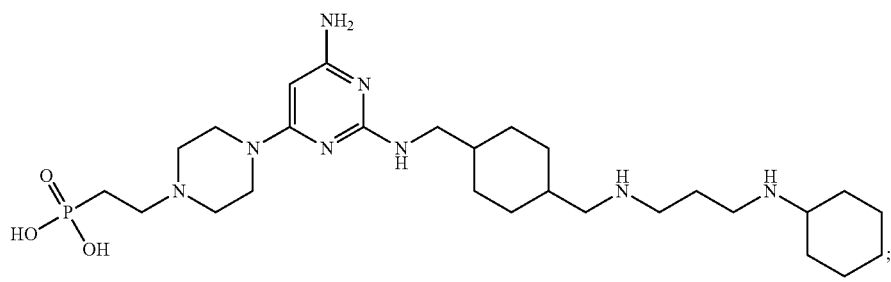

b) LY2510924:
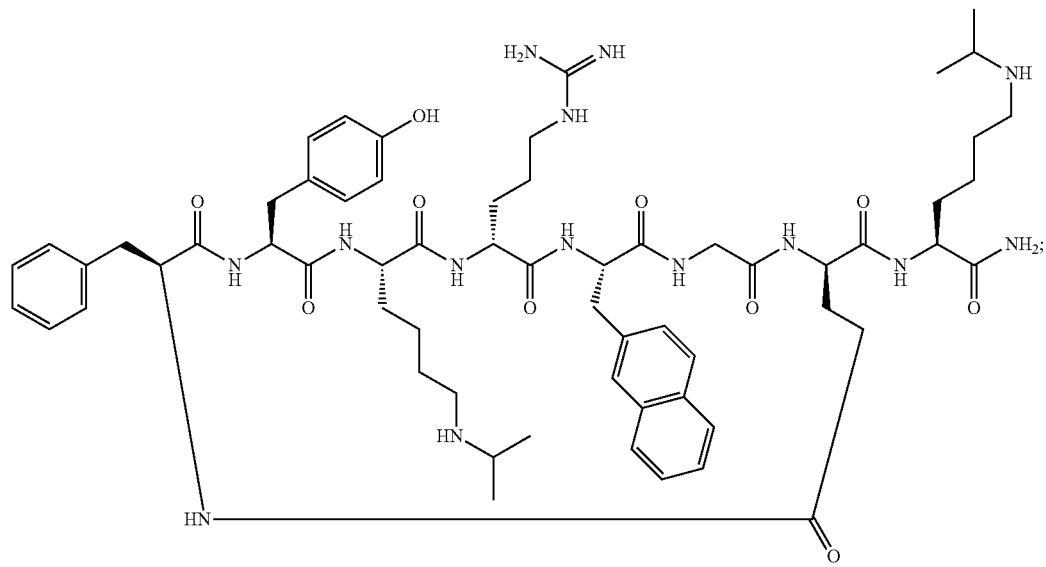 [SMILES: CC(C)NCCCC[C@H](NC(=O)[C@H]1CCC(=O)N[C@@H](Cc2ccccc2)C(=O)N[C@@H](Cc2ccc(O)cc2)C(=O)N[C@@H](CCCCNC(C)C)C(=O)N[C@H](CCCNC(=N)N)C(=O)N[C@@H](Cc2ccc3ccccc3c2)C(=O)NCC(=O)N1)C(N)=O]
c) AMD3.100: and
d) AMD3465:
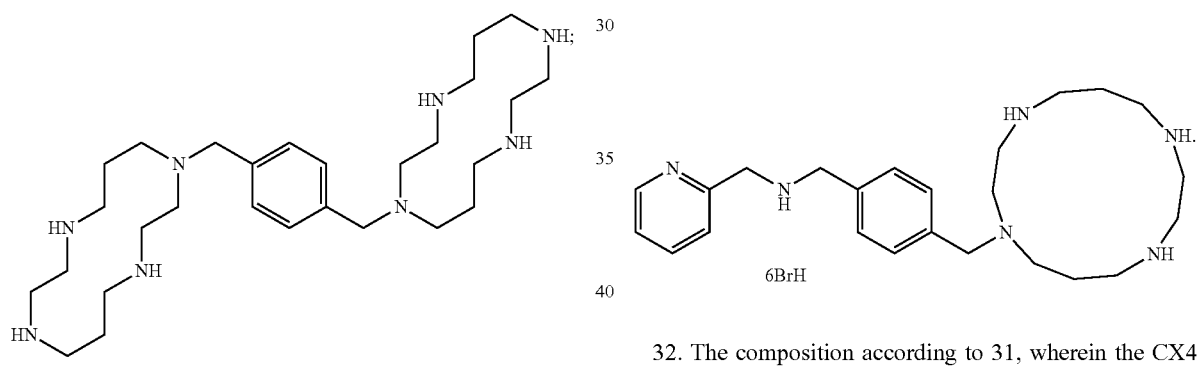
32. The composition according to 31, wherein the CX4/CXCL12 inhibitor is LY2510924:
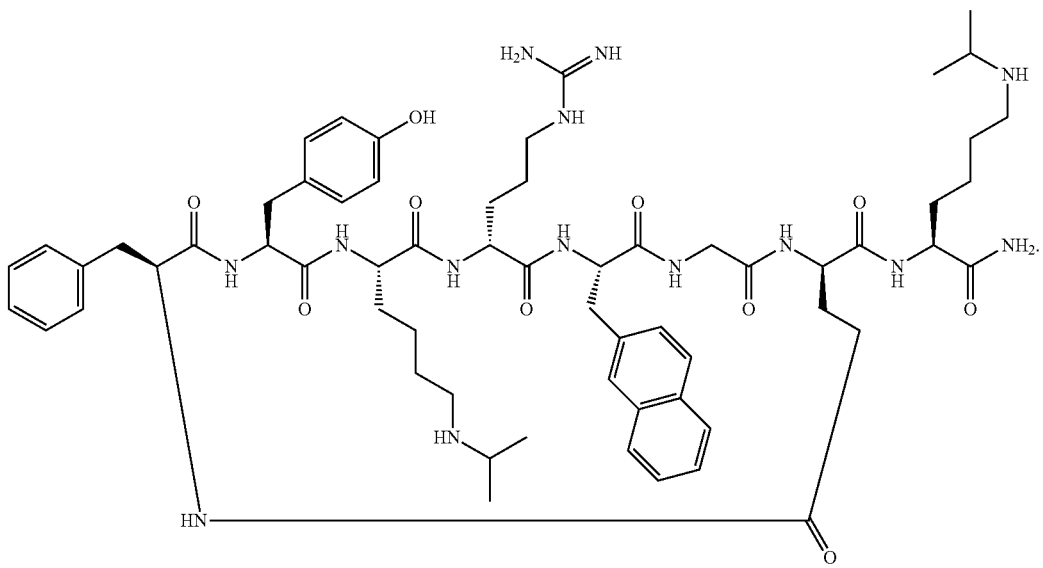 [SMILES: CC(C)NCCCC[C@H](NC(=O)[C@H]1CCC(=O)N[C@@H](Cc2ccccc2)C(=O)N[C@@H](Cc2ccc(O)cc2)C(=O)N[C@@H](CCCCNC(C)C)C(=O)N[C@H](CCCNC(=N)N)C(=O)N[C@@H](Cc2ccc3ccccc3c2)C(=O)NCC(=O)N1)C(N)=O]

33. The composition according to 31, wherein the CX4/CXCL12 inhibitor is burixafor:

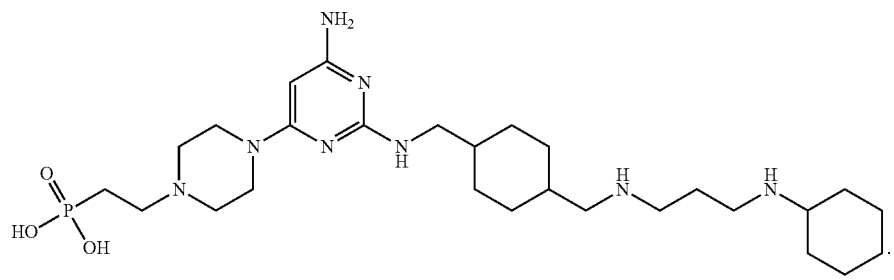

34. The composition according to 33, wherein the compound is of Formula CX-IA1:

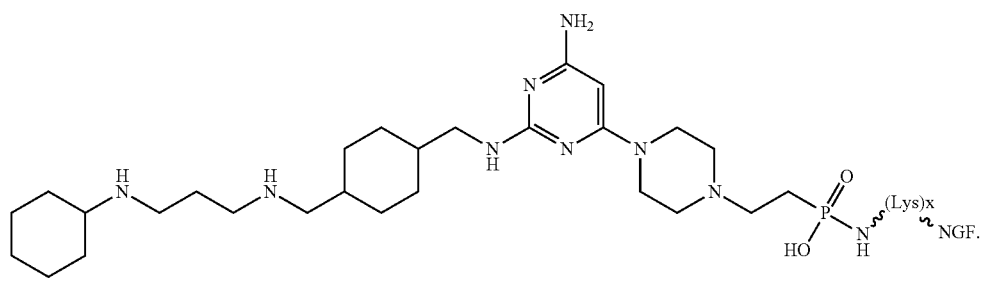

35. The composition according to 33, wherein the compound is of Formula CX-IA2:

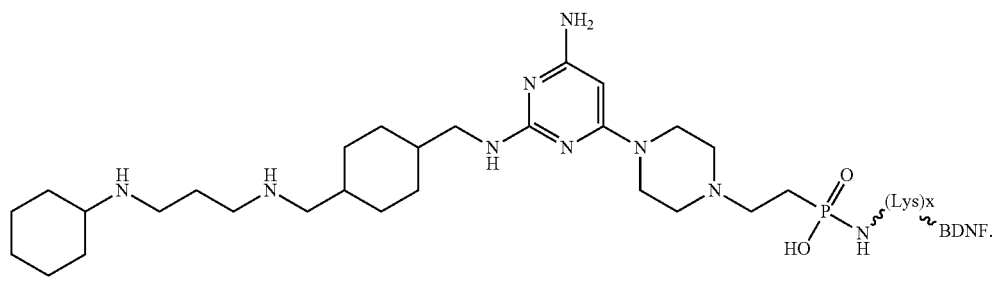

36. The composition according to 17, wherein the compound is an imidazoquinolone amine.

37. The composition according to 24, wherein the compound is imiquimod;

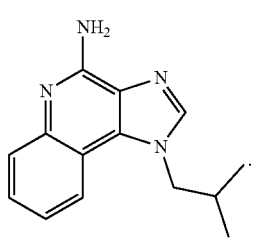 [SMILES: CC(C)Cn1cnc2c(N)nc3ccccc3c21]

38. The composition according to 1, wherein the cancer is skin cancer.

39. The composition according to 38, wherein the anticancer agent is an imidazoquinolone amine.

40. The composition according to 39, wherein the compound is imiquimod:

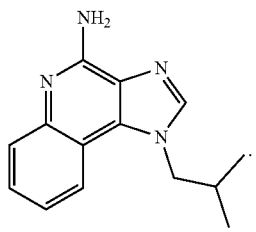 [SMILES: CC(C)Cn1cnc2c(N)nc3ccccc3c21]

41. The composition according to any one of 1-42, wherein the linker is a cleavable linker.

42. The composition according to 40, wherein the linker is an acid-cleavable linker, a base-cleavable linker, a photo-cleavable linker or an enzyme-cleavable linker.

43. The composition according to any one of 1-42, wherein the linker is non-cleavable.

44. The composition according to any one of 1-42, wherein the linker comprises a carbamate.
45. The composition according to any one of 1-44, wherein B is a brain-derived neurotrophic factor (BDNF) or fragment thereof.
46. The composition according to any one of 1-44, wherein B is a nerve growth factor (NGF) or fragment thereof.
47. The composition according to any one of 43-46, wherein B is a BDNF or fragment thereof that binds to tropomyosin receptor kinase B (trkB) or an NGF or fragment thereof that binds to tropomyosin receptor kinase A (trkA).
48. The composition according any one of 43-46, wherein binding of BDNF or fragment thereof to trkB or binding of NGF or fragment thereof to trkA triggers internalization of the compound into a cancer cell.
49. The composition according to any one of 47-48, wherein the cancer is glioma.
50. The composition according to 48, wherein the cancer is optic pathway glioma.
51. The composition according to any one of 43-48, wherein the cancer comprises perineural invasion.
52. The composition according to any one of 43-48, wherein the cancer is skin cancer.
53. The composition according to any one of 1-48, wherein B is a BDNF or fragment thereof or NGF or fragment thereof that binds to p75 neurotrophin receptor.
54. The composition according to 53 wherein binding of the BDNF or fragment thereof or NGF or fragment thereof to p75 triggers internalization of the compound into a cancer cell.
55. The composition according to any one of 53-54, wherein the cancer is glioma.
56. The composition according to 55, wherein the cancer is optic pathway glioma.
57. The composition according to any one of 53-54, wherein the cancer comprises perineural invasion.
58. The composition according to any one of 53-54, wherein the cancer is skin cancer.
61. The composition according to any one of 1-46, wherein B is a ciliary neurotrophic factor (CNTF) or fragment thereof.
62. The composition according to any one of 1-46, wherein B is a neurotrophic factor 3 (NT-3) or fragment thereof.
63. The composition according to any one of 1-46, wherein B is a glial-cell derived neurotrophic factor (GDNF).

Methods of Use
1. A method for delivering an anti-cancer agent selectively into nerve cells, the method comprising:
    administering a compound of formula I:

B—L—X    (I)

wherein:
    B is a protein, peptide or pepetidomimetic that binds selectively to a neurotrophin receptor;
    L is a linker; and
    X is an anti-cancer agent.
2. The method according to 1, wherein the anti-cancer agent is internalized by a cancer cell in response to binding of B to a nerve cell receptor.
3. The method according to 2, wherein the nerve cell receptor is a neurotrophin receptor.
4. The method according to claim 2, wherein the anti-cancer agent is internalized by a cancer cell in response to binding of B to tropomyosin receptor kinase A (trkA) or tropomyosin receptor kinase B (trkB).
5. The method according to 2, wherein the anti-cancer agent is internalized by a cancer cell in response to binding of B to p75 neurotrophin receptor.
6. The method according to any one of 1-5, wherein the compound is administered intracisternally to a subject.
7. The method according to any one of 1-5, wherein the compound is administered intrathecally to a subject.
8. The method according to any one of 1-7, wherein the method further comprises diagnosing a subject as having cancer.
9. The method according to 8, wherein the cancer is a glioma.
10. The method according to 9, wherein the cancer is optic pathway glioma.
11. The method according to any one of 1-10, wherein the anti-cancer agent is a mammalian target of rapamycin (mTOR) inhibitor or mitogen-activated protein kinase (MEK) inhibitor.
12. The method according to 11, wherein the mTOR inhibitor is a compound selected from the group consisting of sirolimus, temsiorolimus, everolimus and ridaforolimus.
13. The method according to 12, wherein the anti-cancer agent is everolimus.
14. The method according to 12, wherein the compound is of Formula IA1:

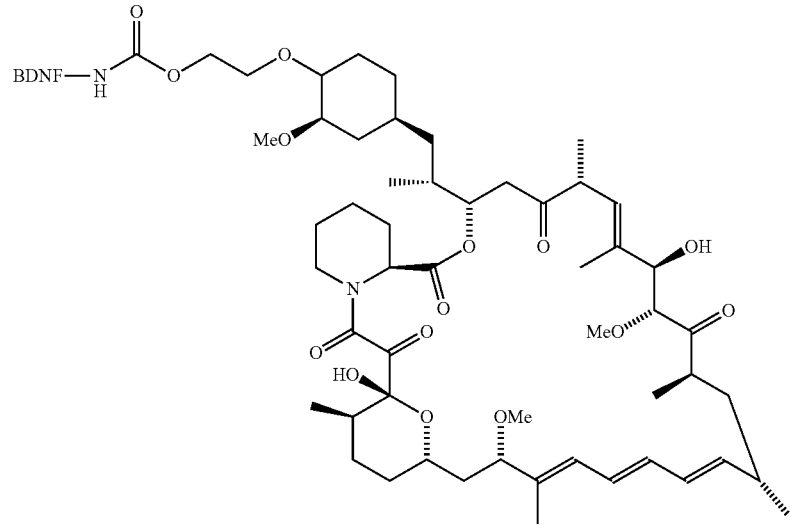

15. The method according to 12, wherein the compound is of Formula IA2:

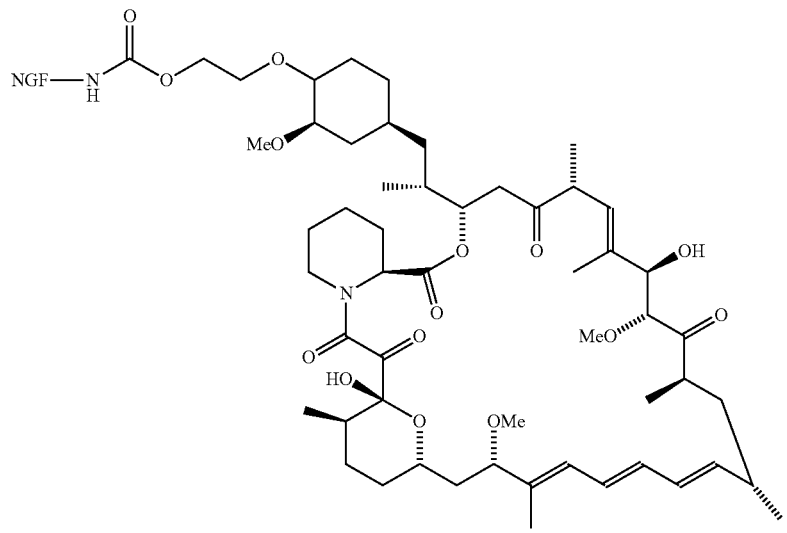

16. The method according to 11, wherein the MEK inhibitor is a compound selected from the group consisting of trametinib, dabrafenib, cobimetinib, vemurafenib, binimetinib, selumetinib.

17. The method according to 16, wherein the anti-cancer agent is selumetinib.

18. The method according to 17, wherein the compound is of Formula IB1:

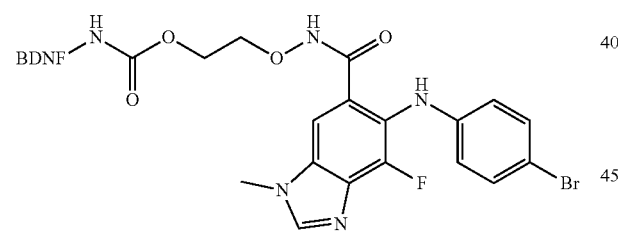

19. The method according to 17, wherein the compound is of Formula IB2:

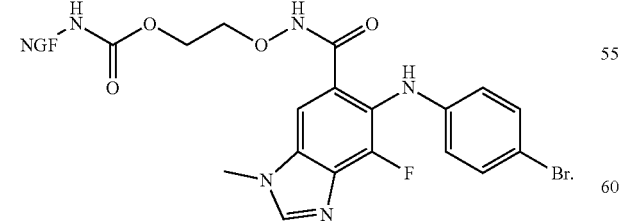

20. The method according to 8, wherein the cancer comprises perineural invasion.

21. The method according to 20, wherein the anti-cancer agent is a heat shock protein 90 (hsp90) inhibitor.

22. The method according to any one of 1-10, wherein the hsp90 inhibitor is a compound selected from the group consisting of:

a) alvespinomycin:

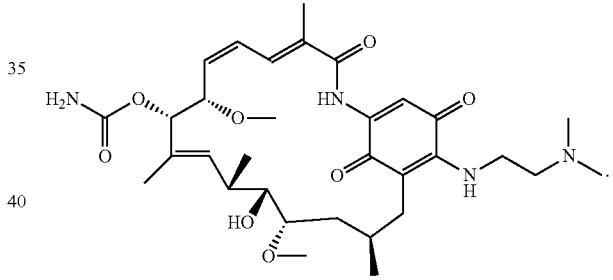

b) 17-N-Allylamino-17-demethoxygeldanamycin (17AAG):

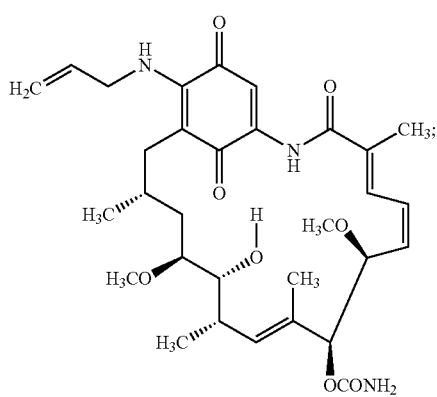

c) luminespib (AUY-922, NVP-AUY922):
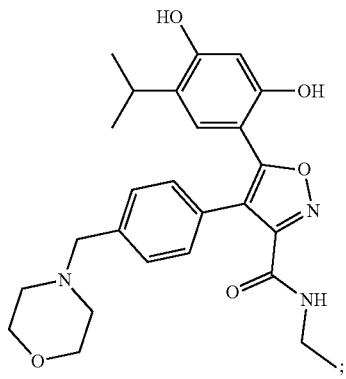 [SMILES: CCNC(=O)c1noc(-c2cc(C(C)C)c(O)cc2O)c1-c1ccc(CN2CCOCC2)cc1]
d) ganetespib (STA-9090):
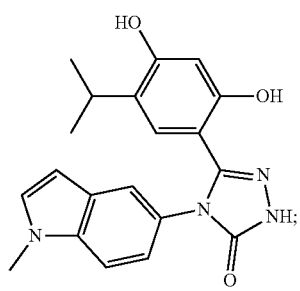 [SMILES: CC(C)c1cc(-c2n[nH]c(=O)n2-c2ccc3c(ccn3C)c2)c(O)cc1O]
e) onalespib (AT13387):
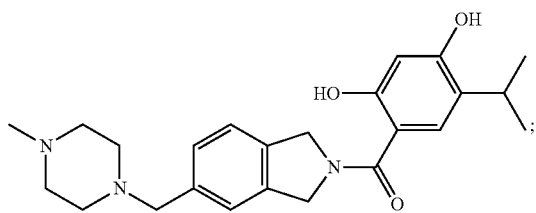 [SMILES: CC(C)c1cc(C(=O)N2Cc3ccc(CN4CCN(C)CC4)cc3C2)c(O)cc1O]
f) NVP-BEP800:
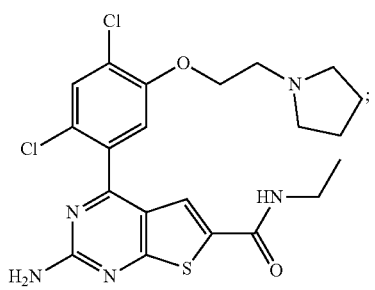 [SMILES: CCNC(=O)c1cc2c(-c3cc(OCCN4CCCC4)c(Cl)cc3Cl)nc(N)nc2s1]
g) BIIB021:
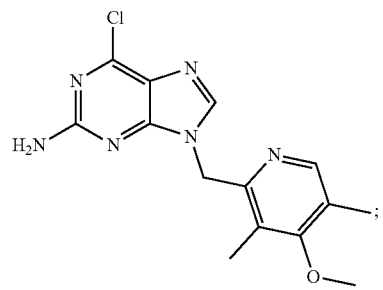 [SMILES: COc1c(C)cnc(Cn2cnc3c(Cl)nc(N)nc32)c1C]
h) PF-04929113 (SNX-5422):
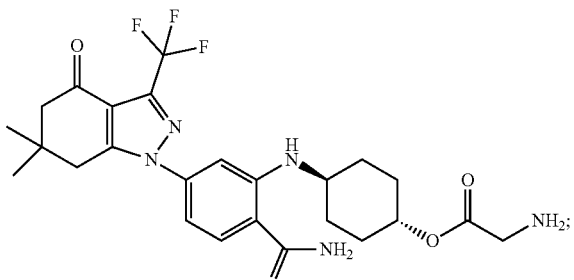
i) SNX-2112 (PF-04928473):
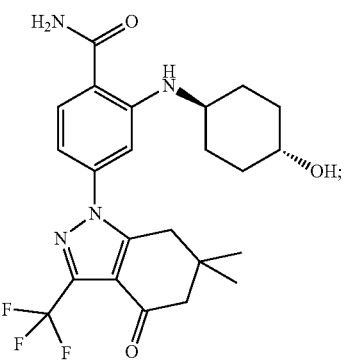 [SMILES: CC1(C)CC(=O)c2c(C(F)(F)F)nn(-c3ccc(C(N)=O)c(N[C@H]4CC[C@H](O)CC4)c3)c2C1]
j) KW-2478:
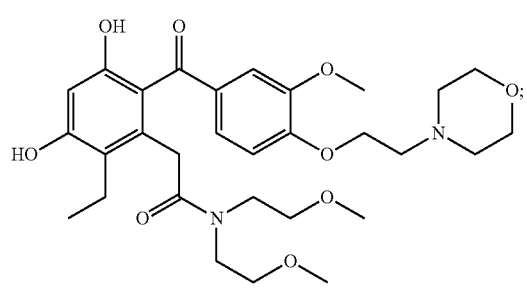 [SMILES: CCc1c(O)cc(O)c(C(=O)c2ccc(OCCN3CCOCC3)c(OC)c2)c1CC(=O)N(CCOC)CCOC]

k) XL888:
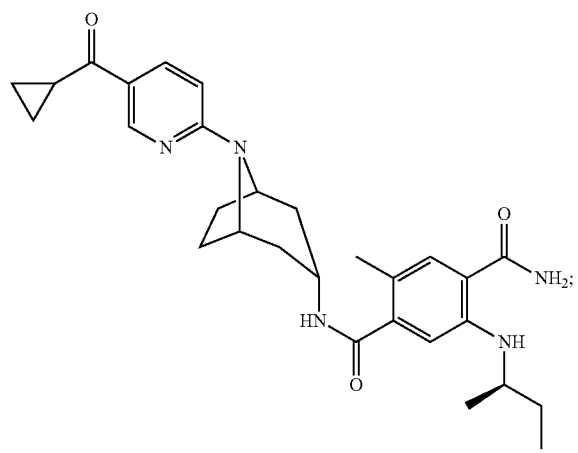 [SMILES: CC[C@@H](C)Nc1cc(C(=O)NC2CC3CCC(C2)N3c2ccc(C(=O)C3CC3)cn2)c(C)cc1C(N)=O]
l) NMS-E973:
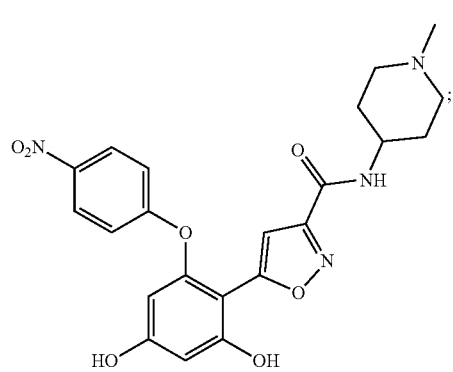 [SMILES: CN1CCC(NC(=O)c2cc(-c3c(O)cc(O)cc3Oc3ccc([N+](=O)[O-])cc3)on2)CC1]
m) PU-H71:
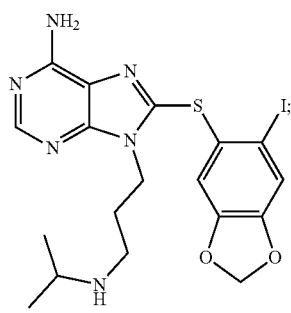 [SMILES: CC(C)NCCCn1c(Sc2cc3c(cc2I)OCO3)nc2c(N)ncnc21]
n) VER-49009:
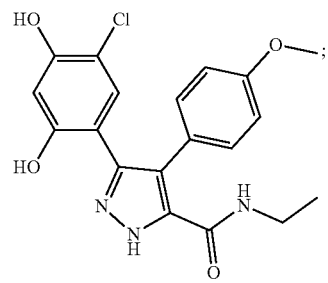 [SMILES: CCNC(=O)c1[nH]nc(-c2cc(Cl)c(O)cc2O)c1-c1ccc(OC)cc1]
o) CH5138303:
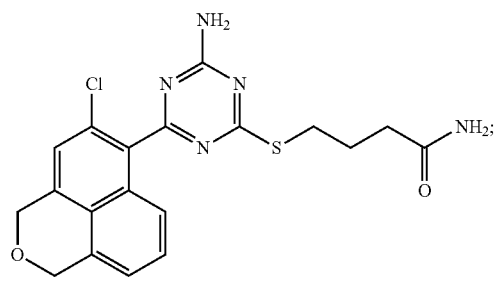 [SMILES: NC(=O)CCCSc1nc(N)nc(-c2c(Cl)cc3c4c(cccc24)COC3)n1]
p) VER-50589:
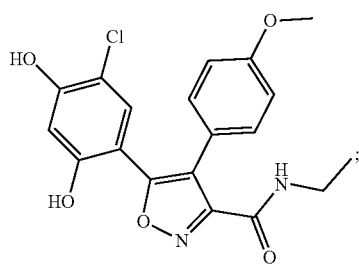 [SMILES: CCNC(=O)c1noc(-c2cc(Cl)c(O)cc2O)c1-c1ccc(OC)cc1]
q) VER155008:
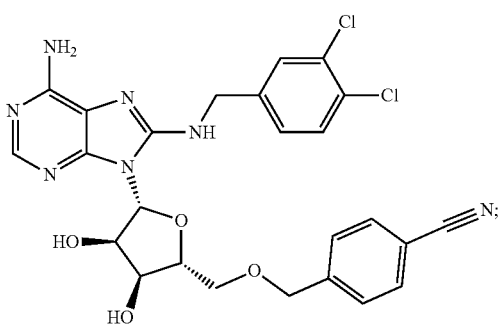

and
r) geldanamycin:

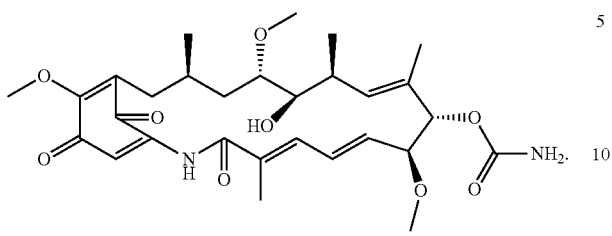

23. The method according to 22, wherein the hsp90 inhibitor is alvespinomycin:

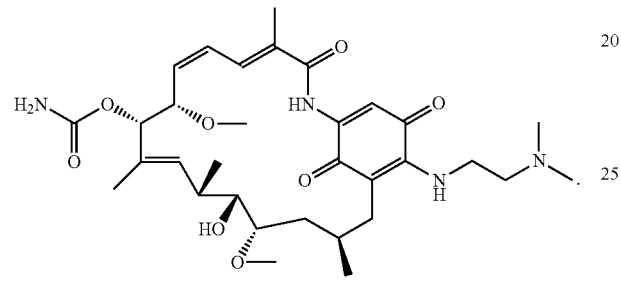

24. The method according to 23, wherein the compound is of Formula HSP-IA1:

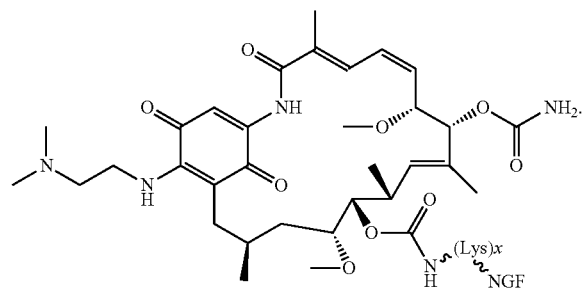

25. The method according to 23, wherein the compound is of Formula HSP-IA2:

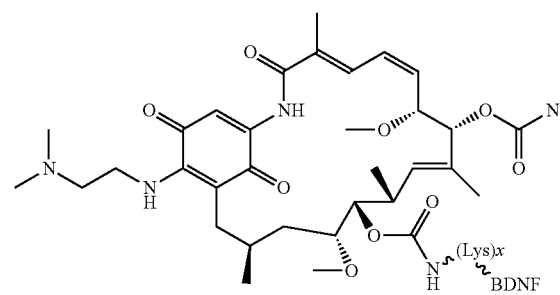

26. The method according to any one of 1-10, wherein the anti-cancer agent is a checkpoint inhibitor.
27. The method according to 26, wherein the checkpoint inhibitor is an inhibitory compound that targets one or more of PD-1, PD-L1, CTLA4, TIM3, LAG3, VISTA, BTLA, TIGIT, LAIR1, CD160, 2B4 and TGFRβ.
28. The method according to 27, wherein the checkpoint inhibitor is an inhibitory compound that targets PD-1.
29. The method according to 27, wherein the checkpoint inhibitor is a compound selected from the group consisting of:
    a) S7911;

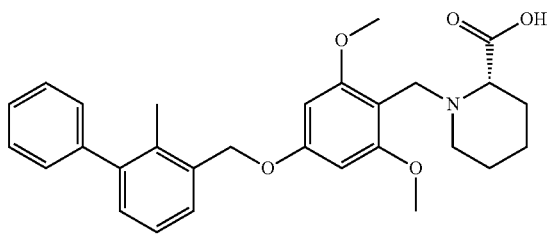 [SMILES: COc1cc(OCc2cccc(-c3ccccc3)c2C)cc(OC)c1CN1CCCC[C@H]1C(=O)O]

b) BMS202:

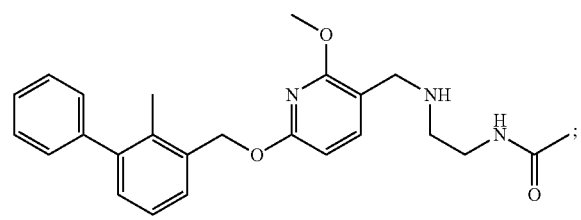 [SMILES: COc1nc(OCc2cccc(-c3ccccc3)c2C)ccc1CNCCNC(C)=O]

and
c) S8158:

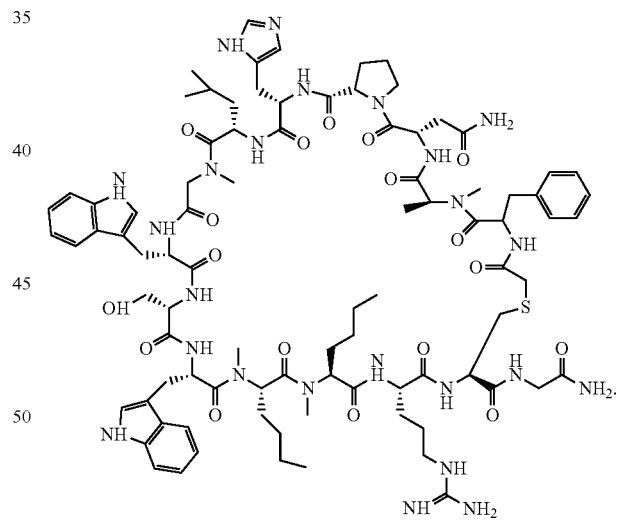

30. The method according to 27, wherein the checkpoint inhibitor is S7911:

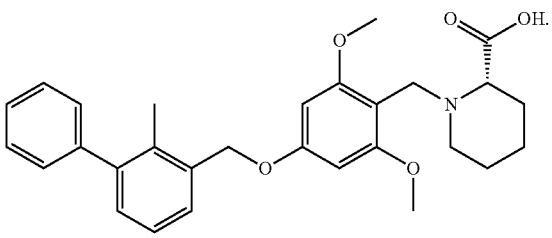 [SMILES: COc1cc(OCc2cccc(-c3ccccc3)c2C)cc(OC)c1CN1CCCC[C@H]1C(=O)O]

31. The method according to 29, wherein the compound is of Formula CP-IA1

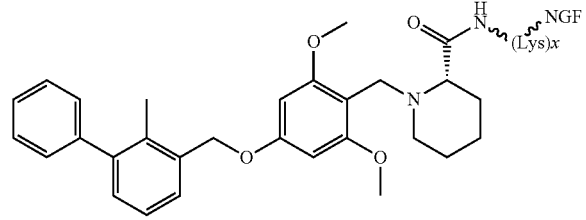

32. The method according to 29, wherein the compound is of Formula CP-IA2

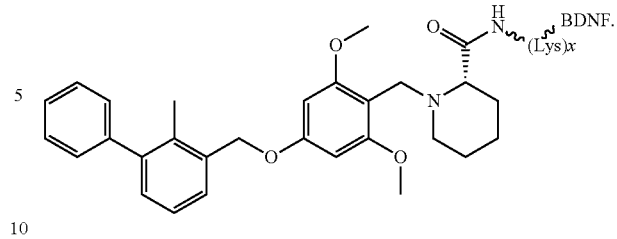

33. The method according to any one of 1-10, wherein the anti-cancer agent is a chemokine 4/chemokine ligand 12 (CX4/CXCL12) inhibitor.

34. The method according to 33, wherein the CX4/CXCL12 inhibitor is a compound selected from the group consisting of:

a) burixafor:

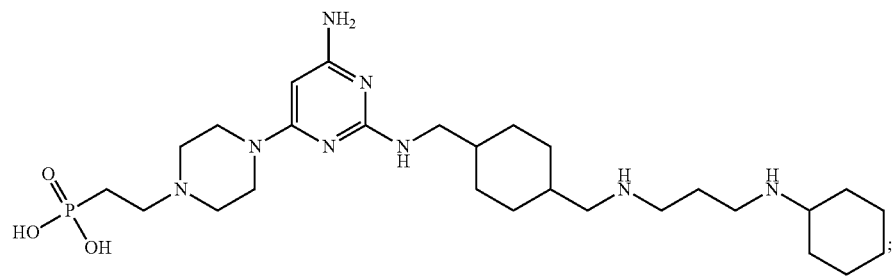 [SMILES: Nc1cc(N2CCN(CCP(=O)(O)O)CC2)nc(NCC2CCC(CNCCCNC3CCCCC3)CC2)n1]

b) LY2510924:

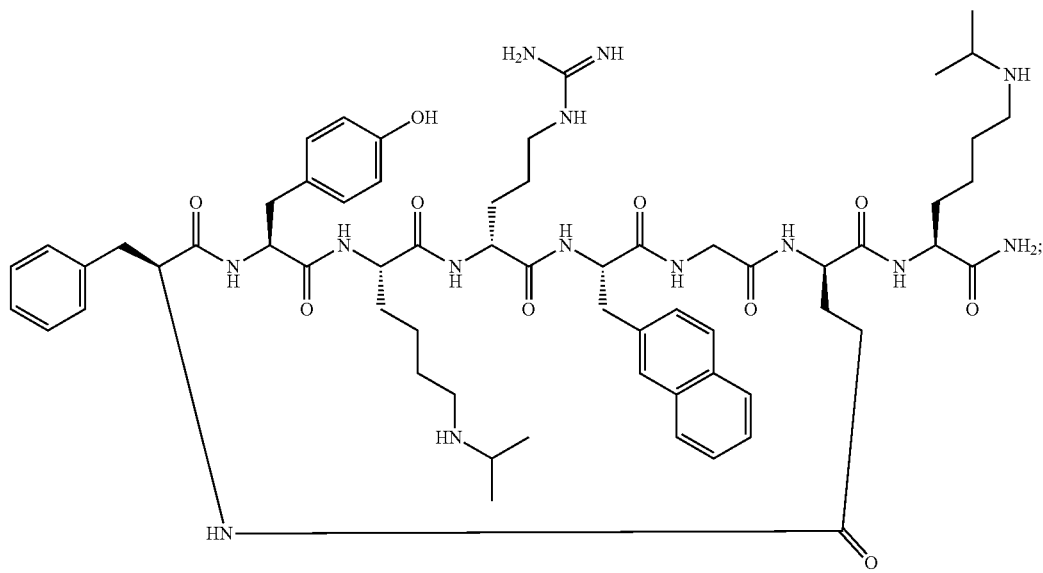 [SMILES: CC(C)NCCCC[C@H](NC(=O)[C@H]1CCC(=O)N[C@@H](Cc2ccccc2)C(=O)N[C@@H](Cc2ccc(O)cc2)C(=O)N[C@@H](CCCCNC(C)C)C(=O)N[C@H](CCCNC(=N)N)C(=O)N[C@@H](Cc2ccc3ccccc3c2)C(=O)NCC(=O)N1)C(N)=O]

c) AMD3100:
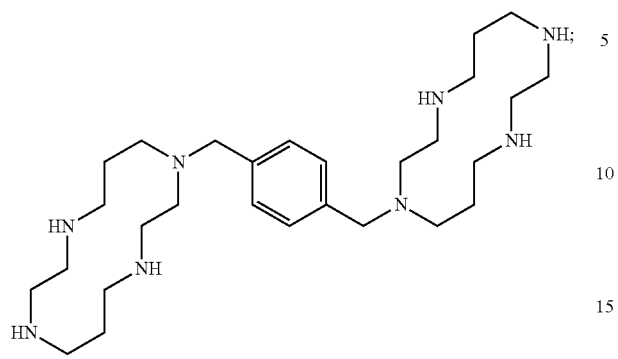
and
d) AMD3465:
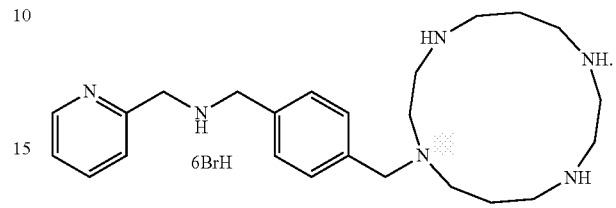
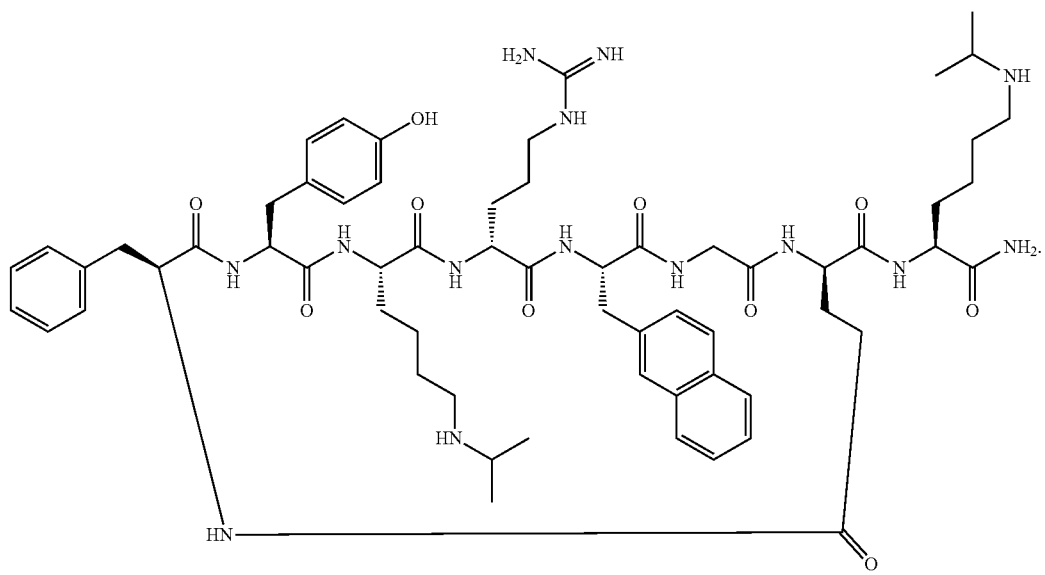 [SMILES: CC(C)NCCCC[C@H](NC(=O)[C@H]1CCC(=O)N[C@@H](Cc2ccccc2)C(=O)N[C@@H](Cc2ccc(O)cc2)C(=O)N[C@@H](CCCCNC(C)C)C(=O)N[C@H](CCCNC(=N)N)C(=O)N[C@@H](Cc2ccc3ccccc3c2)C(=O)NCC(=O)N1)C(N)=O]
36. The method according to 34, wherein the CX4/CXCL12 inhibitor is burixafor:
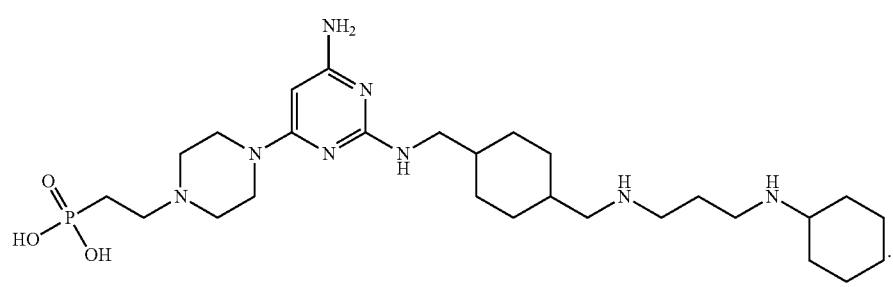

37. The method according to 34, wherein the compound is of Formula CX-IA1:

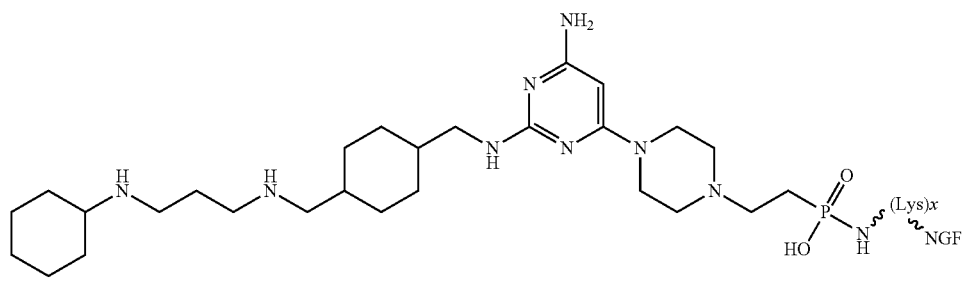

38. The method according to 34, wherein the compound is of Formula CX-IA2:

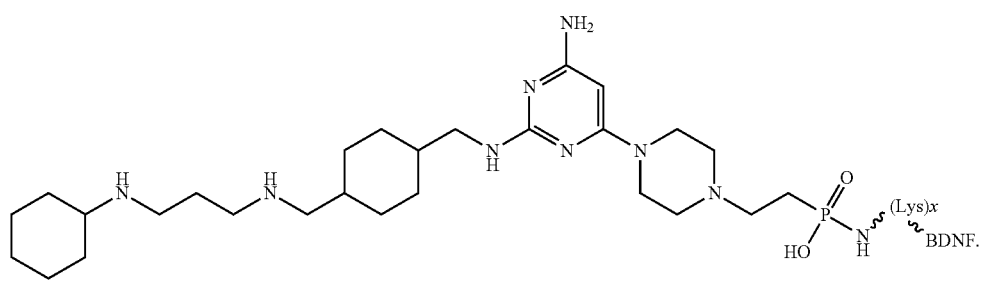

39. The method according to any one of 1-10, wherein the compound is an imidazoquinolone amine.

40. The method according to 39, wherein the compound is imiquimod:

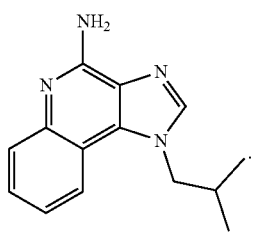 [SMILES: CC(C)Cn1cnc2c(N)nc3ccccc3c21]

41. The method according to 1, wherein the cancer is skin cancer.

42. The method according to 41, wherein the anti-cancer agent is an imidazoquinolone amine.

43. The method according to 42, wherein the compound is imiquimod:

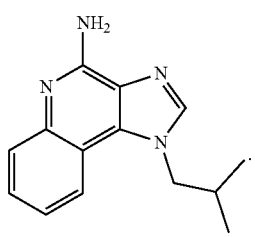 [SMILES: CC(C)Cn1cnc2c(N)nc3ccccc3c21]

44. The method according to any one of 1-13, wherein the linker is a cleavable linker.

45. The method according to 44, wherein the linker is an acid-cleavable linker, abase-cleavable linker, a photo-cleavable linker or an enzyme-cleavable linker.

46. The method according to any one of 1-13, wherein the linker is non-cleavable.

47. The method according to any one of 1-16, wherein the linker comprises a carbamate.

48. The method according to any one of 1-47, wherein B is a brain-derived neurotrophic factor (BDNF) or fragment thereof.

49. The method according to any one of 1-47, wherein B is a nerve growth factor (NGF) or fragment thereof.

50. The method according to any one of 1-47, wherein B is a ciliary neurotrophic factor (CNTF) or fragment thereof.

51. The method according to any one of 1-47, wherein B is a neurotrophic factor 3 (NT-3) or fragment thereof.

52. The method according to any one of 1-47, wherein B is a glial-cell derived neurotrophic factor (GDNF).

Methods of Preparing a Compound of Formula I

1. A method comprising:
   contacting an anti-cancer agent with a bifunctional linker precursor to produce an activated anti-cancer agent; and
   contacting the activated anti-cancer agent with a protein, peptide or pepetidomimetic that binds selectively to a neurotrophin receptor to produce a compound having the formula:

B—L—X (I)

wherein:
B is a protein, peptide or pepetidomimetic that binds selectively to a neurotrophin receptor;
L is a linker; and
X is an anti-cancer agent.

2. The method according to 1, wherein the bifunctional linker precursor is a homobifunctional linker.

3. The method according to 2, wherein the bifunctional linker precursor comprises succinimide.

4. The method according to 2, wherein the bifunctional linker precursor is N,N'-disuccinimidyl carbonate.

5. The method according to any one of 1-4, wherein the anti-cancer agent comprises a hydroxyl group and contacting the bifunctional linker precursor comprises reacting the bifunctional linker precursor with the hydroxyl group of the anti-cancer agent.

6. The method according to 5, wherein the hydroxyl group is a primary hydroxyl group.

7. The method according to any one of 5-6, wherein the method further comprises functionalizing the anti-cancer agent with a hydroxyl group.

8. The method according to any one of 1-7, wherein the activated anti-cancer agent reacts with an amine or sulfhydryl group of the protein, peptide or pepetidomimetic.

9. The method according to 8, wherein the activated anti-cancer agent reacts with an amine group of the protein, peptide or pepetidomimetic.

10. The method according to 8, wherein the activated anti-cancer agent reacts with a lysine side chain of the protein, peptide or pepetidomimetic.

11. The method according to 8, wherein the activated anti-cancer agent reacts with a sulfhydryl group of the protein, peptide or pepetidomimetic.

12. The method according to 11, wherein the anti-cancer agent reacts with a cysteine side chain of the protein, peptide or pepetidomimetic.

13. The method according to any one of 1-12, wherein the protein, peptide or pepetidomimetic binds to tropomyosin receptor kinase A (trkA) or tropomyosin receptor kinase B (trkB).

14. The method according to any one of 1-13, wherein the anti-cancer agent is internalized by a cancer cell in response to binding of B to a nerve cell receptor.

15. The method according to 14, wherein the nerve cell receptor is a neurotrophin receptor.

16. The method according to 14, wherein the anti-cancer agent is internalized by a cancer cell in response to binding of B to tropomyosin receptor kinase A (trkA) or tropomyosin receptor kinase B (trkB).

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 1—Intracisternal Delivery of Conjugates of Brain-Derived Neurotrophic Factor The neurotrophic factor BDNF is selective for the high-affinity receptor tropomyosin kinase B (TrkB). BDNF is a member of the family of neurotrophins that includes Nerve Growth Factor (NGF), NT-3, and NT-4. The Trk receptors are encoded by Trk genes TrkA, TrkB, and TrkC and the low-affinity p75 receptor. Exogenously administered BDNF binds selectively to TrkB, which triggers internalization of BDNF/TrkB complexes in signaling endosomes that are retrogradely transported by dynein motors along axonal microtubules to the neuronal cell body; anterograde transport also occurs. BDNF and TrkB are highly homologous in mammals and humans. Studies in rats of exogenous neurotrophins recapitulate patterns of clinical absorption. TrkB receptors are distributed throughout the CNS, including in the cisterna magna, at the distal ends of the optic nerve.

Methods

A Dyomics Near InfraRed (NIR) dye 800 was conjugated to rhBDNF (800-rhBDNF) as set forth above. The molecular weight (MW) of dye 800 is 1050.15 g/mol, making 800-rhBDNF comparable to a small molecule conjugate compound. Using HPLC, 800-rhBDNF was characterized and subsequently bioassayed in RGC cultures to confirm that TrkB receptor binding remains intact following synthesis. In preliminary studies in naïve rats, 800-rhBDNF given intracisternally transports 800 dye away from the site of injection, via the optic chiasm, to the optic nerve head. Three single doses of 800-rhBDNF were injected midline intracisternally in naïve rats (n=4; n=3 800-rhBDNF, n=1 control, unmodified dye 800 carboxylic acid form). Three test doses of 800-rhBDNF were selected: lowest (5 µL for syringe, at 0.20 concentration=1 µg study article), mid-, and highest (30 µL; upper volume constraint is 50 µL). Images at three timepoints were collected, just prior to treatment, 15 min, and 6 h using two imaging modalities in both eyes (left eye, oculus sinister, OS; right eye, oculus dexter, OD). Imaging and histopathology methods were used to detect 800-rhBDNF in the optic chiasm or optic nerve head.

Two seetings were selected on the Heidelberg Spectralis®. Infrared autofluorescence IRAF; or ICG, to detect indocyanine green, an NIR dye uses a diode laser with a wavelength of 790 nm in the NIR spectrum. A barrier filter at 830 nm separates excitation and fluorescence light and thus, IRAF/ICG detects near IR fluorescence in 800-rhBDNF. Infrared reflectance (IR) excites at 820 nm wavelength, but because it does not separate excitation and fluorescence light, IR does not capture fluorescence and shows NIR 800 dye in vitreous as a "shadow." Histopathology after euthanasia at 6 h. After dissection, tissues were cryostatted to preserve NIR 800. Two directly contiguous sets of slides were produced from two sections of optic nerve, optic chiasm from brain tissue, and optic nerve head from eyes. HE stain.

Hematoxylin and eosin (HE) stain was applied to one slide set to reveal nerve tissue. NIR microscopy. Using an Olympus IX73 inverted 2-deck microscope with motorized filter cube turret; objective turret; Proscan XYZ stage; a 75 W Xenon burner; and DP80 Dual CCD 12.7 MP camera, NIR images are acquired in two channels at 4× in the FITC channel (detects auto-fluorescence) and ICG channel. The morphology of HE stained slides to those with FITC+NIR images was compared to confirm that NIR 800 had localized to in nerve tissue.

Results

Near InfraRed 800 in live animals was detected with both IRAF and IR settings on the Spectralis® at baseline, 15 min, and 6 h; No localized irritation in the retinas was observed. Midline injection was distributed bilaterally. Comparing the morphology of NIR microscopy to HE stain, the control was more diffuse than the 800-BDNF conjugate, which localizes the 800 dye and moves the 800 dye away from the injection site via optic chiasm to optic nerve head.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:
1. A compound of selected from the group consisting of:
a. a compound of Formula IA1:

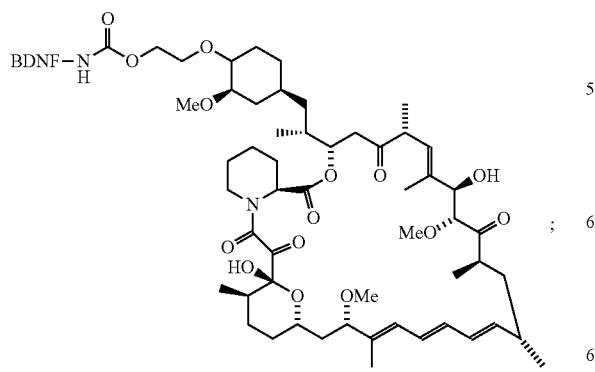

b. a compound of Formula IA2:

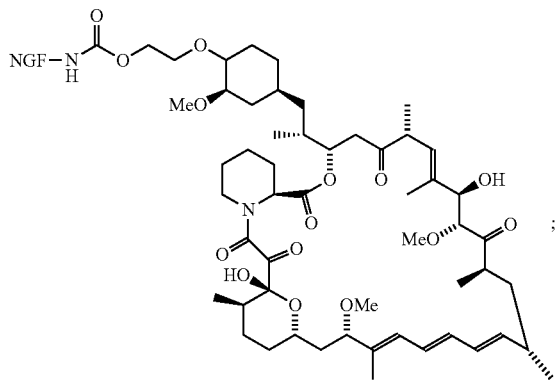

c. a compound of Formula IB1:

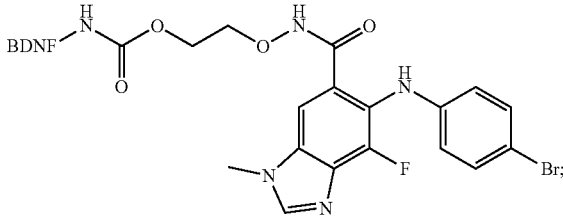

d. a compound of Formula IB2:

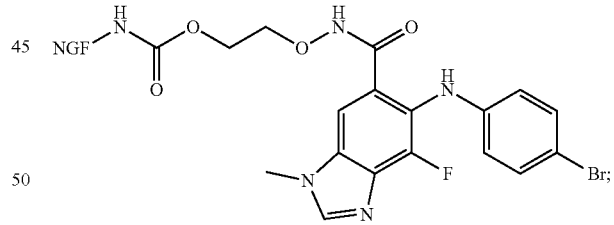

e. a BDNF-selumetinib conjugate of Formula BDNF-SE:

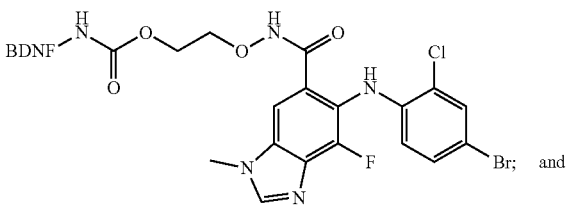

and f. an NGF-selumetinib conjugate of Formula NGF-SE:

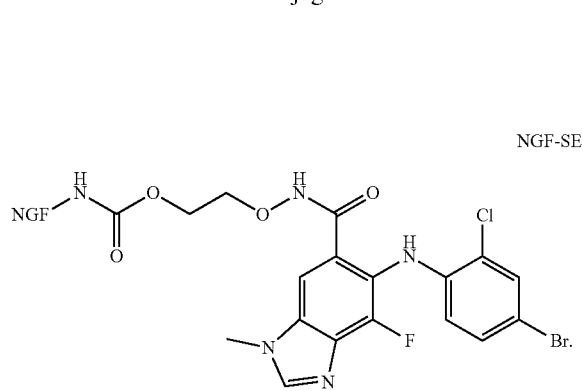

NGF-SE

2. The compound according to claim 1, wherein the compound is of Formula IA1:

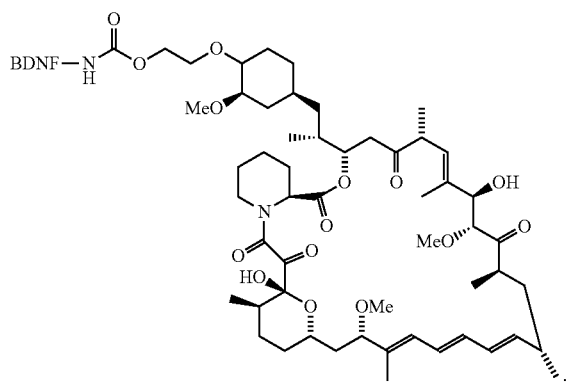

3. The compound according to claim 1, wherein the compound is of Formula IA2:

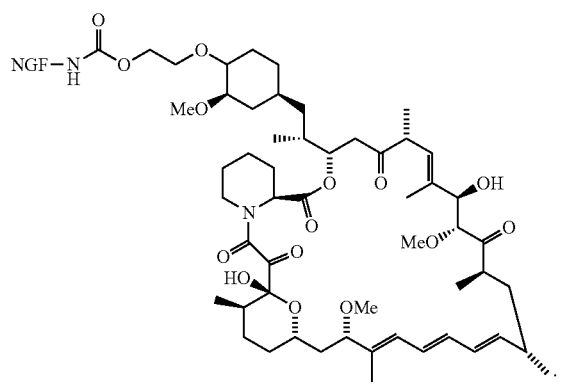

4. The compound according to claim 1, wherein the compound is of Formula IB1:

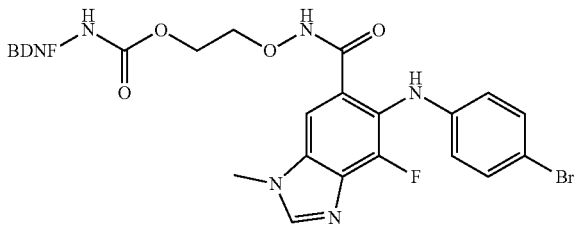

5. The compound according to claim 1, wherein the compound is of Formula IB2:

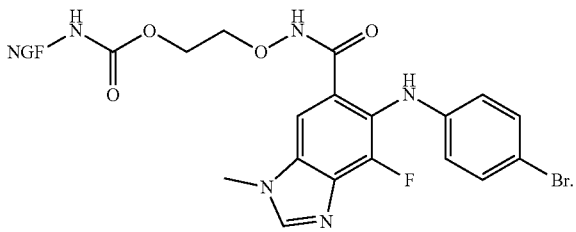

6. The compound according to claim 1, wherein the anti-cancer agent is a compound for the treatment of a glioma, a skin cancer or perineural invasion.

7. A composition comprising:
   a compound of claim 1 and a pharmaceutically acceptable carrier.

8. A method for delivering an anti-cancer agent selectively into nerve cells, the method comprising administering to a subject a compound of claim 1.

9. The compound according to claim 1, wherein the compound is the BDNF-selumetinib conjugate:

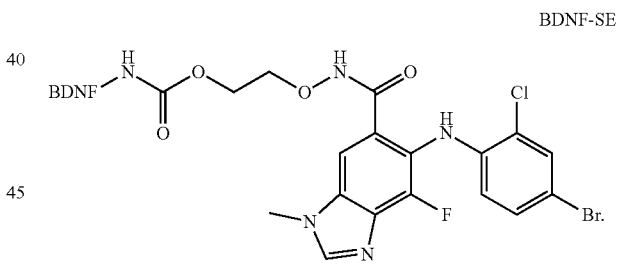

BDNF-SE

10. The compound according to claim 1, wherein the compound is the NGF-selumetinib conjugate:

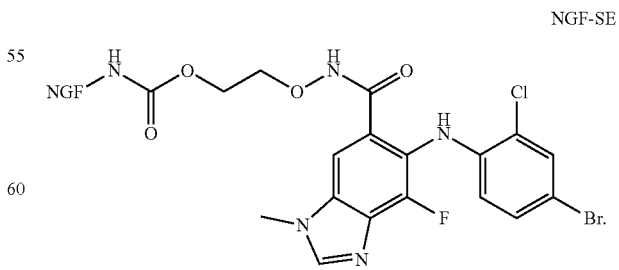

NGF-SE

* * * * *